(12) United States Patent
Wright et al.

(10) Patent No.: US 8,734,833 B2
(45) Date of Patent: *May 27, 2014

(54) THERAPEUTIC FOAM

(71) Applicant: BTG International Ltd., London (GB)

(72) Inventors: David Dakin Iorwerth Wright, Henley on Thames (GB); Anthony David Harman, Henley on Thames (GB); Nikki Robinson, Newmachar (GB); Garry Hodges, Welwyn (GB); Adil Kadar, London (GB); Geoffrey D. Moggridge, Cambridge (GB); Hugh Van Liew, Barnstable, MA (US)

(73) Assignee: BTG International Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/667,296

(22) Filed: Nov. 2, 2012

(65) Prior Publication Data

US 2013/0059923 A1    Mar. 7, 2013

Related U.S. Application Data

(63) Continuation of application No. 12/765,980, filed on Apr. 23, 2010, now Pat. No. 8,323,677, which is a continuation of application No. 10/522,527, filed as application No. PCT/GB2004/004848 on Nov. 17, 2004, now Pat. No. 7,731,986.

(60) Provisional application No. 60/542,867, filed on Feb. 10, 2004, provisional application No. 60/542,866, filed on Feb. 10, 2004.

(30) Foreign Application Priority Data

Nov. 17, 2003  (GB) .................................. 0326768.9
Oct. 7, 2004   (GB) .................................. 0422307.9

(51) Int. Cl.
*A61K 9/08*    (2006.01)

(52) U.S. Cl.
USPC .......................................................... 424/423

(58) Field of Classification Search
USPC .......................................................... 424/423
See application file for complete search history.

(56) References Cited

U.S. PATENT DOCUMENTS

| | | | |
|---|---|---|---|
| 7,357,336 B2 * | 4/2008 | Osman et al. | 239/337 |
| 7,731,986 B2 * | 6/2010 | Wright et al. | 424/423 |
| 7,763,269 B2 * | 7/2010 | Wright et al. | 424/423 |
| 8,323,677 B2 * | 12/2012 | Wright et al. | 424/423 |

FOREIGN PATENT DOCUMENTS

WO    WO-00/72821 A1 * 12/2000

* cited by examiner

*Primary Examiner* — Ali Soroush
(74) *Attorney, Agent, or Firm* — Finnegan, Henderson, Farabow, Garrett & Dunner, LLP

(57) ABSTRACT

A therapeutic foam for the treatment of, inter alia, varicose veins comprises a sclerosing solution foamed with a physiological gas such as carbon dioxide, oxygen or a mixture thereof. The foam has a nitrogen content of less than 0.8%. It may be generated using a pressurized canister system incorporating a fine mesh of micron dimensions through which the gas and sclerosing liquid are passed to make the foam. Alternatively, the foam may be generated by passing gas and solution between two syringes through a fine mesh. Techniques are described for minimizing the amount of nitrogen in a canister or syringe based product. A technique for generating and delivering foam simultaneously using a syringe based device is also disclosed.

42 Claims, 20 Drawing Sheets

THERAPEUTIC FOAM

This is a continuation of application Ser. No. 12/765,980, filed Apr. 23, 2010, which is a continuation of application Ser. No. 10/522,527, filed Jan. 26, 2005, which is the National Stage Entry of PCT/GB2004/004848, which claims priority of U.S. Provisional Application Nos. 60/542,867 and 60/542,866 filed Feb. 10, 2004. The PCT/GB2004/004848 application also claims priority of UK Patent Application Nos. 0422307.9, filed Oct. 7, 2004, and 0326768.9, filed Nov. 17, 2003. All of these applications are herein incorporated by reference.

The present invention relates to the generation of foam comprising a sclerosing material, particularly a sclerosing solution, which is suitable for use in the treatment of various medical conditions involving blood vessels, particularly varicose veins and other disorders involving venous malformation.

Sclerosis of varicose veins is based on the injection into the veins of liquid sclerosant substances which, by inter alia causing a localised inflammatory reaction, favour the elimination of these abnormal veins. Until recently, sclerotherapy was a technique selected in cases of small and medium calibre varicose veins, those with diameters equal to or greater than 7 mm being treated by surgery.

An injectable microfoam suitable for therapeutic use, on larger veins in particular, has now been developed and is described in EP-A-0656203 and U.S. Pat. No. 5,676,962 (Cabrera & Cabrera), incorporated herein by reference. These describe a low-density microfoam produced with a sclerosing substance which, when injected into a vein, displaces blood and ensures that the sclerosing agent contacts the endothelium of the vessel in a known concentration and for a controllable time, achieving sclerosis of the entire segment occupied.

Prior to the priority date of these patents it had been known for many years that injection of liquid sclerosant into varicose veins, especially smaller varicose veins, could be effective. It had also been known for many years to inject a small quantity of air into a vein prior to injecting sclerosing liquid, the objective being to displace blood from the vein to avoid the sclerosing agent being diluted too quickly. A development of this technique was to make a loose foam or froth and to inject this instead of pure air, prior to injection of the sclerosant liquid. These techniques, known as "air block"and developed by Orbach, were generally only effective for treating smaller veins.

In addition there had been disclosures of finer foams for treatment of smaller varicose veins (Fluckiger references cited below), or a combined procedure using both surgery and foam for treatment of the entire long saphenous vein: Mayer: Brucke: "*The Aetiotogy and Treatment of Varicosities of the Lower Extremities*", Chirurgische Praxis, 521-528, 1957.

All of these prior disclosures of foam/froth treatment describe the preparation of the foam/froth with air as the gaseous component. None of the documents mentions the air in the injected foam giving rise to serious problems. One reference mentions an apparently short lived air embolism: P. Fluckiger: "*Non-surgical retrograde sclerosis of varicose veins with Varsyl foam*", Schweizerische Medizinische Wochenschrift No. 48, pp 1368-1370(1956). In this article, the author indicates that he reduced the volume of foam administered to 10 ml from 15 ml as a result of a patient experiencing chest pain on standing immediately after treatment with 15 ml of foam, in a later lecture, the same author indicates that he has in fact subsequently used 15 ml foam without noting ill effects: lecture dated 1962 entitled "*A contribution to techniques for outpatient treatment of varicose veins*" delivered to the Hamburg Dermatological Society. The reference by Mayer and Brucke cited above appears to describe the use of as much as 50 ml of air foam and does not mention any problems.

However, it is known that rapid intravenous injection of a large quantity of air, as opposed to air foam, can lead to air embolism which may be fatal. In spite of this practitioners of the air block and foam techniques described above do not report that the volumes of air involved in their techniques were sufficient to cause serious problems.

The air block technique had largely fallen out of favour by the 1980s and the other foam techniques mentioned above were virtually unheard-of.

The Cabreras proposed the use of a microfoam, that is to say a microfoam with microscopically small bubbles, e.g., where the majority of the bubbles are not visible to the naked eye, for injection into varicose veins. The use of a microfoam, as opposed to larger bubbled foam or froth, gives rise to many advantages in terms of controllability and ability to displace blood in even the largest varicose veins, allowing treatment of virtually all varicose veins without recourse to surgery. As used here, the term foam encompasses foams with bubbles of all sizes including microfoams.

The first teaching that potential issues with intravenous injection of a microfoam product made with air are serious enough to warrant change is to be found in the Cabrera patent references mentioned above. These documents indicate that the prior air based techniques are "dangerous owing to the side effects of atmospheric nitrogen which is only slightly soluble in blood", though it is not mentioned exactly what the dangers are nor what volumes or rates of injection of air or nitrogen gas give rise to these dangers.

In addition to being the first to propose a microfoam as opposed to a larger bubbled foam, and to propose treatment of even the largest veins without surgery, the Cabreras also proposed that the microfoam be made with oxygen or a mixture of carbon dioxide and oxygen. In the context of this background, the Cabreras' contribution can be seen to be highly innovative in a number of respects—appreciating against the prevailing thinking at the time (i) the potential of a sclerosant microfoam, (ii) the need for soluble gases, (iii) the use of oxygen which does not degrade the microfoam yet is taken up by blood, (iv) the safety of oxygen but also (v) the possibility of incorporating a percentage of highly soluble carbon dioxide.

Since publication of the Cabreras' microfoam technique in the mid 1990s many practitioners have adopted foam both in Europe and the USA. At the recent worldwide conference of phlebologists in San Diego in August 2003, approximately one third of the two hundred and fifty or so papers which were presented concerned foam treatment.

Almost without exception, however, practitioners using sclerosing foam today make it with air. Opinion varies as to how much foam should be injected—some advocate as little as 5 ml whilst others are prepared to inject more.

The Cabreras' microfoam is prepared extemporaneously in the clinic immediately prior to use. The preparation involves beating sclerosant solution with a small brush rotated at high speed by a motor, under a cover which is connected to a source of oxygen or oxygen and carbon dioxide. Most practitioners who have followed the Cabreras use an alternative technique for extemporaneous preparation of foam which involves passing sclerosant solution and air repeatedly between two connected syringes. Another alternative is a syringe with a second plunger with holes in its face and which is independently movable in the syringe barrel to froth a liquid and gas mixture in the syringe. Both of these latter types of procedure are somewhat inconvenient and allow for variation of the foam composition depending upon the person preparing it gas content, bubble size, density and stability all require attention. These techniques require a high degree of care and knowledge that may be difficult to replicate under pressure, i.e. when time available to prepare the foam is short.

A product which aims essentially to reproduce the Cabreras' microfoam in a more convenient and easily reproducible way is currently being developed and is in clinical trials in Europe and the USA. This product is a pressurised canister system, in which the foam is produced by passing gas and sclerosant solution under pressure through a number of fine meshes. In the trials of this product the aim is to treat an entire long saphenous vein and its varicosed tributaries in a single treatment, which can mean injection of 25 ml or even 50 ml of foam.

WO 00/72821-A1 (BTG International Limited), incorporated herein by reference, describes the fundamental concepts underlying this canister product. The foam is produced by passing gas and sclerosant liquid through one or more meshes having small apertures measured in microns. Like the Cabrera patents, this document acknowledges the potential issues with air/nitrogen and seeks to reduce the levels of nitrogen in the foam. A preferred form of gas described in WO 00/72821-A1 comprises 50% vol/vol or more oxygen, the remainder being carb dioxide, or on dioxide, or carbon dioxide, nitrogen and trace gases in the proportion found in atmospheric air.

In a later patent application, WO 02/41872-A1 (BTG International Limited), incorporated herein by reference, the sclerosant liquid and an oxygen-rich physiologically acceptable blood dispersible gas are stored in separate containers until immediately prior to use, when the blood-dispersible gas is introduced into the container holding the sclerosant liquid. The mixture of blood-dispersible gas and sclerosant liquid is then released, the components of the mixture interacting upon release of the mixture to form a sclerosing foam. In the system described in this patent application, a proportion of nitrogen (25%) is deliberately introduced into the polidocanol canister. After charging of the sclerosing liquid (polidocanol) can with oxygen from the higher pressure oxygen canister, the percentage of nitrogen is reduced to about 7 or 8%. It was believed that this level of nitrogen could be tolerated.

The device disclosed in WO 02/41872-A1 gives a good uniform injectable foam, irrespective of the gases used. Use of 100% $CO_2$ as the filling gas in the polidocanol canister is preferred, as $CO_2$ is very soluble in the bloodstream, but the present inventors have observed that increasing $CO_2$ percentage in the final gas mix may cause an undesirable decrease in foam stability, resulting in a shorter half separation time. In particular, the half-life of the foam can fall short of the figure of 2.5 minutes which is indicated in WO 00/72821-A1 as being preferable.

The present inventors are continuing to research clinical aspects of the injection of sclerosing foam as well as developing the canister foam product and putting it through clinical trials in Europe and the USA. It has always been the intention to develop a safe foam product which is as well defined as possible but whose specification has achievable tolerances. There are many parameters of a foam which may be varied. These include, without limitation: the chemical, its purity and the strength of the solution; the size of bubbles, or more accurately the distribution of sizes, the density (i.e. ratio of liquid to gas), the longevity of the foam (measured in terms of "half life", or the time taken for half the foam to revert to liquid) and the gas mixture.

Nitrogen, which makes up approximately 80% of air, is difficult as a practical matter to exclude totally from a foam. This is true whether the foam is made using a canister system, in which case nitrogen tends to creep into the canister during manufacture, or using either of the syringe techniques or the Cabreras' rotating brush technique, or indeed any of a number of other less common techniques which have been developed since the Cabreras' disclosure of microfoam.

In a two syringe technique the likely method for introducing the gas component, if a foam were to be made with a gas other then air, would be to connect one syringe to a pressurised source of gas, then disconnect and reconnect it to another syringe containing sclerosant. In this sort of technique, the two syringes are pumped to create foam and then the foam-filled syringe separated. The potential for ingress of a small percentage of air/nitrogen during this process is obvious. Similarly, even with the Cabreras' technique, it may be difficult to exclude 100% of air/nitrogen from the environment in which the foam is prepared.

One of the objectives of the foam product being developed by the inventors is to treat an entire greater saphenous vein together with major varicose tributaries in a human patient with one injection. This requires up to 25 ml, 30 ml or possibly even 50 ml of foam. Currently, the most conservative users of air foam inject a maximum of 5 ml into the venous system, apparently without observing any deleterious effects. The inventors therefore reasoned that an equivalent amount of nitrogen in a relatively large dose of foam needed to treat the entire saphenous vein should also be safe. They therefore used this as a starting point: 5 ml of air with 80% nitrogen will contain 4 ml nitrogen; a corresponding proportion of nitrogen in, say, 50 ml of low nitrogen foam would be around 8%.

Until recently, its has been believed by the inventors that a foam with approximately 8% nitrogen would be acceptable from a safety standpoint and that this percentage represented an easily achievable tolerance for nitrogen levels in the foam specification. Accepting this level of nitrogen also has the advantage that a small quantity of nitrogen could be introduced deliberately into the polidocanol canister to reduce the adverse effects of the highly soluble carbon dioxide on the foam stability (as discussed above). This foam and a system for making it is described in WO 02/41872-A1, referred to above.

As discussed above, apart from the above mentioned patent publications, the published art on foam treatment of varicose veins mentions little if any danger from injecting air foam up to 15 ml. The only event noted by Fluckiger was temporary chest pain. The above mentioned patent publications which mention dangers with nitrogen are silent regarding the amount of nitrogen which would be dangerous and what damaging effects it may cause. A great many practitioners are currently using air based foam, though some restrict the quantity injected to 5 ml. The inventors have been involved in a 650 patient multi-centre European phase III clinical trial of the canister product described above which contains 7-8% nitrogen; no serious adverse events associated with the gas component of the foam were noted.

Now, further research in connection with the clinical trials of the canister system described above has revealed the presence of large numbers of bubbles in the heart, some of which endure for a significant period of time. Ultrasound monitoring of the heart during treatment of patients in this trial has revealed many bubbles on the right side of the heart and in associated blood vessels. Since foam is injected into the venous circulation, i.e. that connected to the right side of the heart, it was expected that some bubbles on the right side of the heart would be observed. However, the number and persistence of the bubbles was surprising.

Furthermore, bubbles have been observed on the left side of the heart in a patient who was subsequently shown to have a minor septal defect, or patent foramen ovate ("PFO"), i.e. a hole in the heart. The patent reported experiencing a transient visual disturbance. This is significant because, once on the left side of the circulation, the bubbles can progress to the brain, where they may cause microinfarcts.

At present it is believed that screening all patients for even the most minor PFO is not really feasible for an elective procedure such as varicose vein treatment and may not even be possible. The techniques required would be fairly sophisticated and possibly quite invasive. Furthermore this would increase the time required for the procedure and preclude treatment of patients having such PFOs, of which it is believed there are significant numbers.

In the light of these unexpected findings, considerable further fundamental research has been carried out by the inventors.

Experiments using animal models have been carried out by the inventors and internationally recognised experts in their field have been commissioned to carry out detailed mathematical modelling of the behaviour of oxygen, carbon dioxide and nitrogen bubbles in blood. In vitro work to measure the absorption of gases in fresh human venous blood has also been carried out by the inventors. As a result it has become clear that, contrary to previous thinking by the inventors, and in stark contrast to the thinking of almost every practitioner currently preparing extemporaneous foam for use in varicose vein treatment, even the smallest volume of nitrogen may be significant in causing persistent bubbles.

Furthermore, recent studies have been published further confirming that air foams previously suggested in the art are causing some complications for certain patient groups. For example, Dr. Philip Kritzinger, MD has presented case studies where foams for sclerotherapy of veins that were made using air as the gas phase may lead to seizures and myocardial infarction in some geriatrics or patients at high risk of coronary problems.

The inventors have now determined that in order to produce a product suitable for administration to patients without the need for lengthy PFO screening methodology it may be required to reduce the amount of nitrogen to upper limits that were previously unrecognised.

Further developments of the canister system described in WO00/72821-A1 and WO02/41872-A1 have been devised, specifically raising the percentage of carbon dioxide in the foam and reducing the nitrogen present in the foam to near zero. To compensate for the deleterious effects of the highly soluble carbon dioxide, the size of the apertures in the mesh has been reduced to 5 microns from 20 microns. Canisters of this design have been made in reasonably large numbers for testing. Initially, double canister systems as described above were prepared by flushing the canisters with the desired gas before sealing and pressurising them. This product generated a foam with between 1% and 2% nitrogen. Further research has led the inventors to believe, however, that even this level may be too high.

Recognising that there will always be impurity no matter what technique is adopted for making the foam, the inventors believe that a sclerosing foam having a percentage by volume of nitrogen gas within the range 0.01% and 0.8% is both clinically safe and consistently reproducible, it may be possible routinely to produce canisters with as little as 0.0001% nitrogen gas. Examples presented below illustrate the manufacture/preparation and also the clinical effects of such a foam.

The inventors also recognise that techniques such as those described above using syringes, together with a variety of other techniques for extemporaneous preparation of sclerosing foam which have been developed since the Cabreras disclosure, may have their place in the field of foam sclitopathy. These techniques may well provide a less expensive option than a canister product. The inventors believe that it is possible to prepare foams having a very low percentage of nitrogen, as set out above, using these types of technique as well as using a canister system.

According to the present invention, a foam comprising a liquid phase and a gas phase wherein the liquid phase comprises at least one sclerosing agent and the gas phase consisting essentially of gaseous nitrogen present in an amount ranging from 0.0001% to 0.8% by volume and at least one physiologically acceptable gas. In a further embodiment, the gas phase may further comprise other gases such as trace gases as defined below, which may also effect at least one of at least one of the density, half life, viscosity, and bubble size of the resulting foam. As used herein, consisting essentially of means that one or more additional component may be added, such as gas, that would not substantially effect at least one of the density, half life, viscosity, and bubble size of the resulting foam.

"Physiologically acceptable gas" means gases which are relatively readily absorbed by the blood or which can pass rapidly across the pulmonary gas exchange membranes. Specifically, oxygen, carbon dioxide, nitrous oxide and helium are contemplated. Other gases, which may or may not fall within the terms of the definition of physiologically acceptable gases, may be used at least in small quantities, e.g. xenon, argon, neon or others. As used herein, a gas phase that is "substantially" a specific gas, such as "substantially O2", refers to a gas phase that is O2 with the impurities normally found in commercial medical grade O2 gas. Gases which are found only at trace concentrations in the atmosphere (such as those just mentioned) may be useful to incorporate in the formulation, e.g. at relatively low concentrations of between about 0.1% and 5%, in order to facilitate the detection of leaks.

In another embodiment, the said other gas consists essentially of oxygen. Another possibility is for the other gas to consist essentially of oxygen and a minor proportion, preferably 40% or less of carbon dioxide, still more preferably 30% or less of carbon dioxide. For example, the gas phase may comprise at least 50% O2, such as for example, as 70%, 80%, 90% and 99% O2 in another embodiment, it may also comprise a major portion of CO2, such great than 50% CO2, such as 70%, 80%, 90% and 99% CO2. In these cases, between 0.1% and 5% of the other gas may be constituted by gases which are only found at trace levels in the atmosphere, e.g. argon, helium, xenon, neon. Alternatively the gas may be substantially 100% nitrous oxide or a mixture of at least two of oxygen, nitrous oxide and carbon dioxide.

For the purpose of this application various other terms have the following definitions: A sclerosant liquid is a liquid that is capable of sclerosing blood vessels when injected into the vessel lumen and includes without limitation solutions of polidocanol, tetradecyl sulphate, ethanolamine oleate, sodium morrhuate, hypertonic glucosated or glucosaline solutions, chromated glycerol, iodated solutions. Sclerothpathy or sclerotherapy relates to the treatment of blood vessels to eliminate them. An aerosol is a dispersion of liquid in gas. A major proportion of a gas is over 50% volume/volume. A minor proportion of a gas is under 60% volume/volume. A minor amount of one liquid in another liquid is under 50% of the total volume. Atmospheric pressure and bar are 1000 mbar gauge. Half-life of a foam is the time taken for half the liquid in the foam to revert to unfoamed liquid phase.

As suggested by Cabrera and discussed above, one could use oxygen or mixtures of oxygen and carbon dioxide as the gas component. Carbon dioxide is very soluble in water (and hence blood) and oxygen is not very soluble in water but is taken up relatively rapidly by hemoglobin in blood. The present inventors have also done studies that have shown that CO2 and O2 are taken up in blood much faster than N2 or air. However, foams made solely with carbon dioxide, or other highly water-soluble gases, tend to be very unstable and do not last long enough to be usable. Because CO2 foams have a very short half life, foams with a high concentration of CO2 have not been used in the past to prepare foams for sclerotherapy.

For example, a predominantly insoluble gas mix such as air will yield a stable, stiff foam with a half separation time of 150-200 seconds using the Cabrera method. However, highly soluble gas atmospheres such as 100% CO2 yield foams with much shorter half separation times. It is thought that the rapid dissolution and transport of CO2 in the lamellar cell walls of the foam is responsible for the reduced stability of some CO2 foams. This allows the smaller, high pressure bubbles of the foam to rapidly transfer all their gas content to adjacent larger low pressure bubbles, which then rise through the foam to burst or accumulate at a surface. This process is called Ostwalt ripening, and with all-CO2 foams the liquid cell wall is no longer a significant barrier to diffusion between adjacent bubbles at different Laplace pressures. Drainage and separation of foam into gas and liquid components is also influenced by the viscosity of the liquid component.

Oxygen foams do not have this problem, but the injection of oxygen gas has been reported to be dangerous and, in fact, has been said to be almost as dangerous as air when injected into the venous system. See, for example, Moore & Braselton "*Injections of Air and carbon Dioxide into a Pulmonary Vein*", Annals of Surgery, Vol 112, 1940, pp 212-218. While another study suggests that for some high risk patient groups high concentrations of O2 in foams used for sclerotherapy may increase the risk of side effects.

Recent studies have also suggested that foams for sclerotherapy made with high concentrations of N2 or O2 may lead to potential side effects in certain patient groups. More specifically, one study suggests that high concentrations of nitrogen may lead to a higher risk of arterial embolism in certain patient populations.

The present inventors, however, have discovered that it is possible to make an effective foam for use in sclerotherapy using high concentrations of CO2 as the gas phase and the addition of a viscosity enhancing agent to the liquid phase. The addition of a viscosity enhancing agent, however, while increasing the half life of a CO2 foam, also increases the density of the foam. Too high a density can hinder a foams ability to displace blood and therefore be an effective foam for sclerotherapy. It was discovered that a balance of density and half life enables the production of an effective foam. In one embodiment, this balance of density and half life is achieved by increasing the viscosity enhancing agent to at least 20% wt/wt and using various methods as described herein to produce the foam.

Viscosity enhancing agents include any agent that will increase the viscosity of the liquid phase, such as PVP and glycerol. In one embodiment, at least 20% wt/wt viscosity enhancing agent is present in the liquid phase, such as for example 25%, 30%, 35%, 40%.

Viscosity of the liquid phase before production of the foam may also be a factor in the half life of the foam. For example, increasing viscosity of the liquid phase will increase half life of the foam. However, a higher viscosity may raise the density of the resulting foam in some systems.

Thus, in a further embodiment, the foam of the invention comprises a liquid phase and a gas phase wherein the liquid phase comprises at least one sclerosing agent and is at least 20% wt/wt of at least one viscosity enhancing agent; and the gas phase comprises at least 50% CO2; and wherein the foam has a density less than 0.25 g/ml and half life of greater than 100 secs. The gas phase may, for example be at least 75% CO2, such as at least 90% CO2, such as at least 99% CO2. In one embodiment, the gas phase consists essentially of CO2.

The foam, for example, may have a half life of at least 90 second, such as at least 100, such as at least 110, such as at least 120 seconds, such as at least 130 seconds, such as at least 140 seconds, such as at least 150 seconds, such as at least 160 seconds, such as at least 170 seconds, such as at least 180 seconds, and such as at least 3.5 minutes. The density of the foam may range from 0.07 to 0.22 g/ml, such as 0.07 to 0.19 g/ml, 0.07 to 0.16 g/ml, such as 0.08 to 0.14 g/ml, also such as 0.8 to 0.15 g/ml, such as 0.9 to 0.13 g/ml and such as 0.10 to 0.14 g/ml. The gas phase may further comprises another physiologically acceptable gas that is dispersible in blood, such as O2. The viscosity of the liquid phase may range from 2.0 to 10 cP, such 2.0 to 7.0 cP, such as 2.0 to 5.0 cP, such as 2.0 to 3.5 cP, such as from 2.0 to 3.0 cP, such as 2.0 to 2.5 cP.

FIGURES

Figure 16:
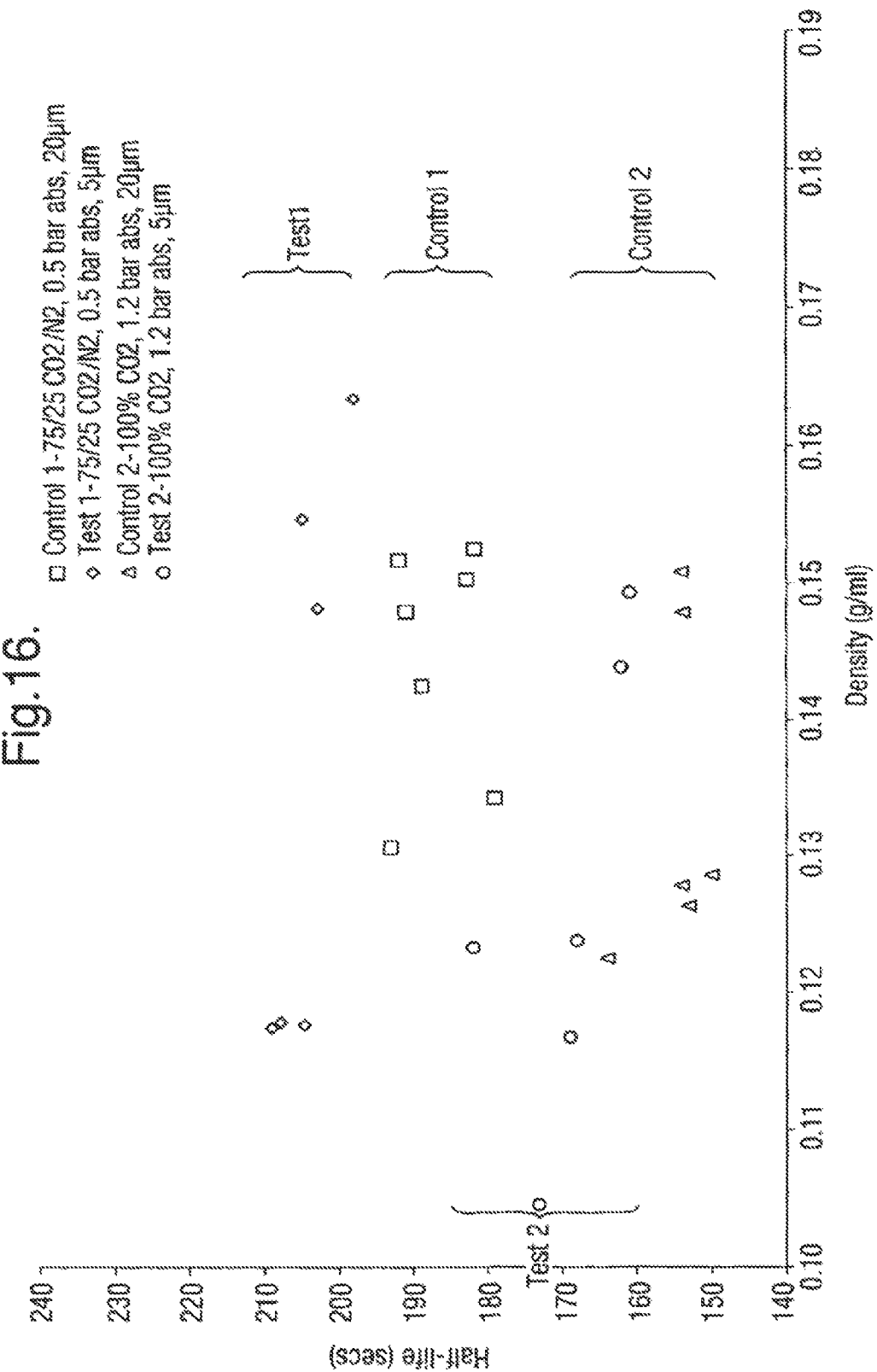

FIG. 16 shows a graph to compare the results from the four bi-can conditions tested in Example 3 below, showing the effect of gas mix, gas pressure and shuttle mesh on foam density and half-life. Control 1 uses a 75% CO2/25% N2 gas mixture in a 0.5 bar canister with a 5 µm mesh; Test 1 uses the same gas mixture with a 5 µm mesh; Control 2 uses 100% CO2 in a 1.2 bar canister with the 20 µm mesh; Test 2 uses the same gas with a 5 µm mesh.

Figure 17:
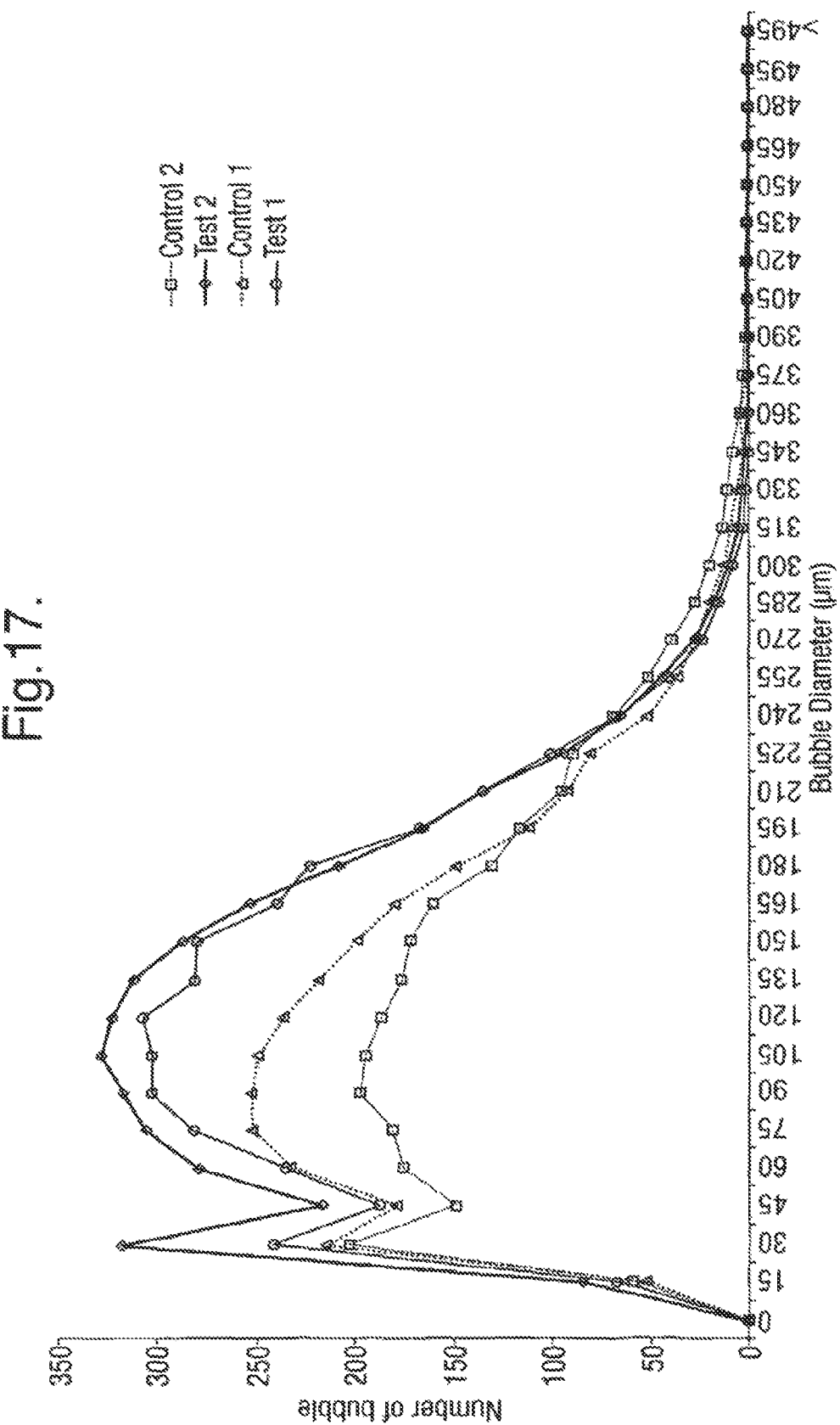

FIG. 17 shows a graph of the average number of bubbles by diameter from the four bi-can conditions tested below.

Figure 18:
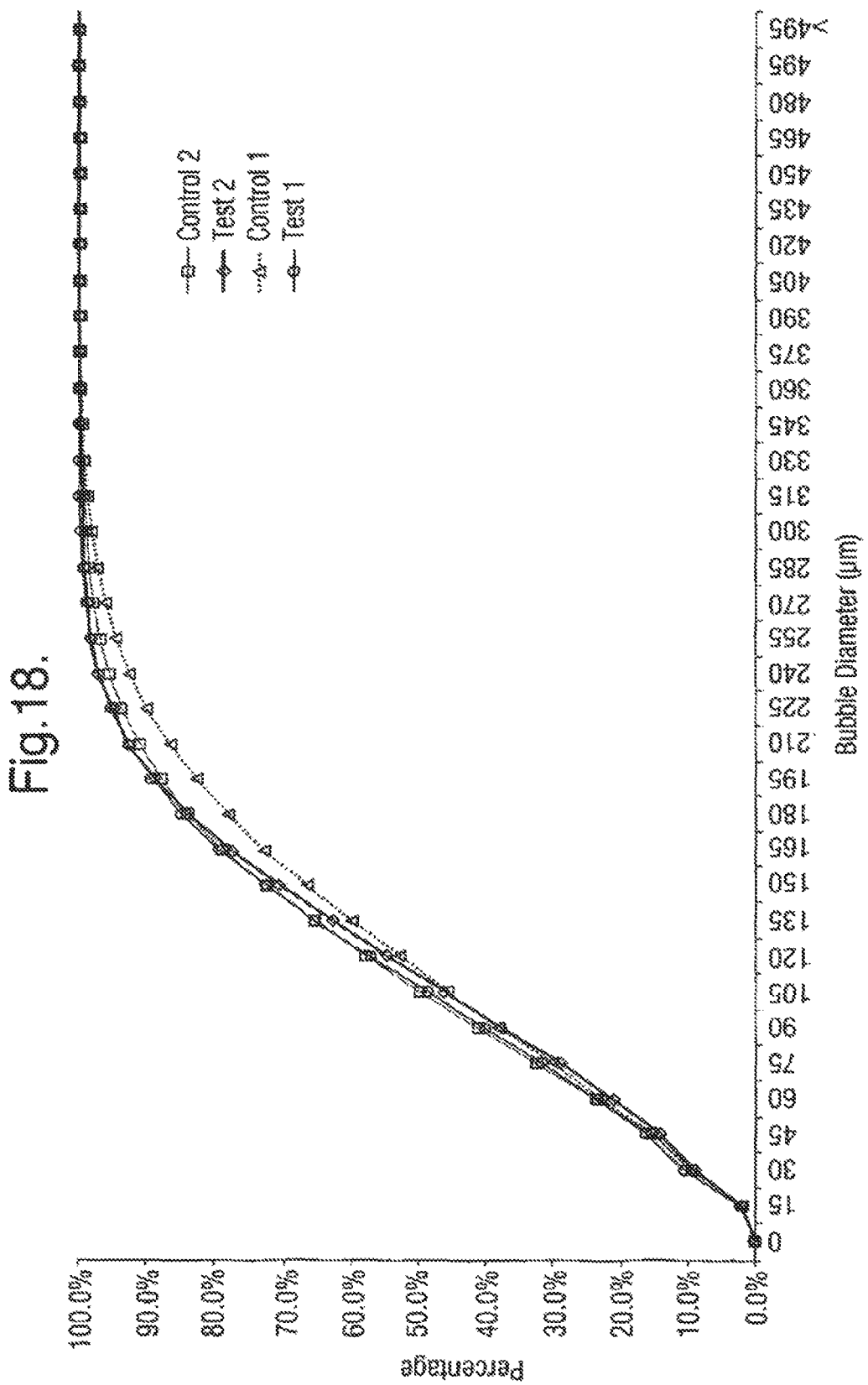

FIG. 18 shows a graph of the proportion of bubbles by diameter from the four bi-can conditions tested in below.

Figure 19:
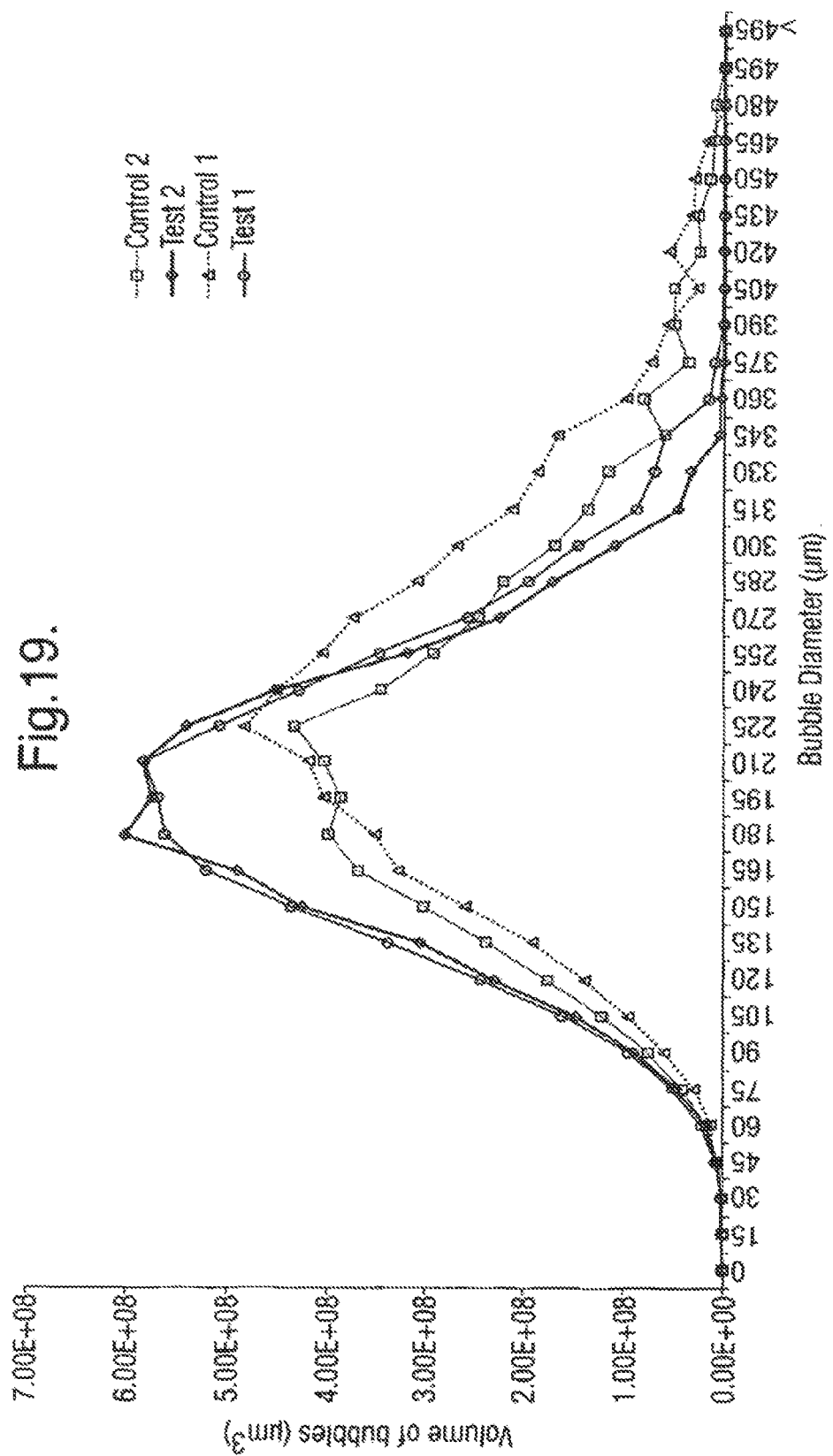

FIG. 19 shows a graph of the average volume of bubbles by diameter from the four bi-can conditions tested in below.

Figure 20:
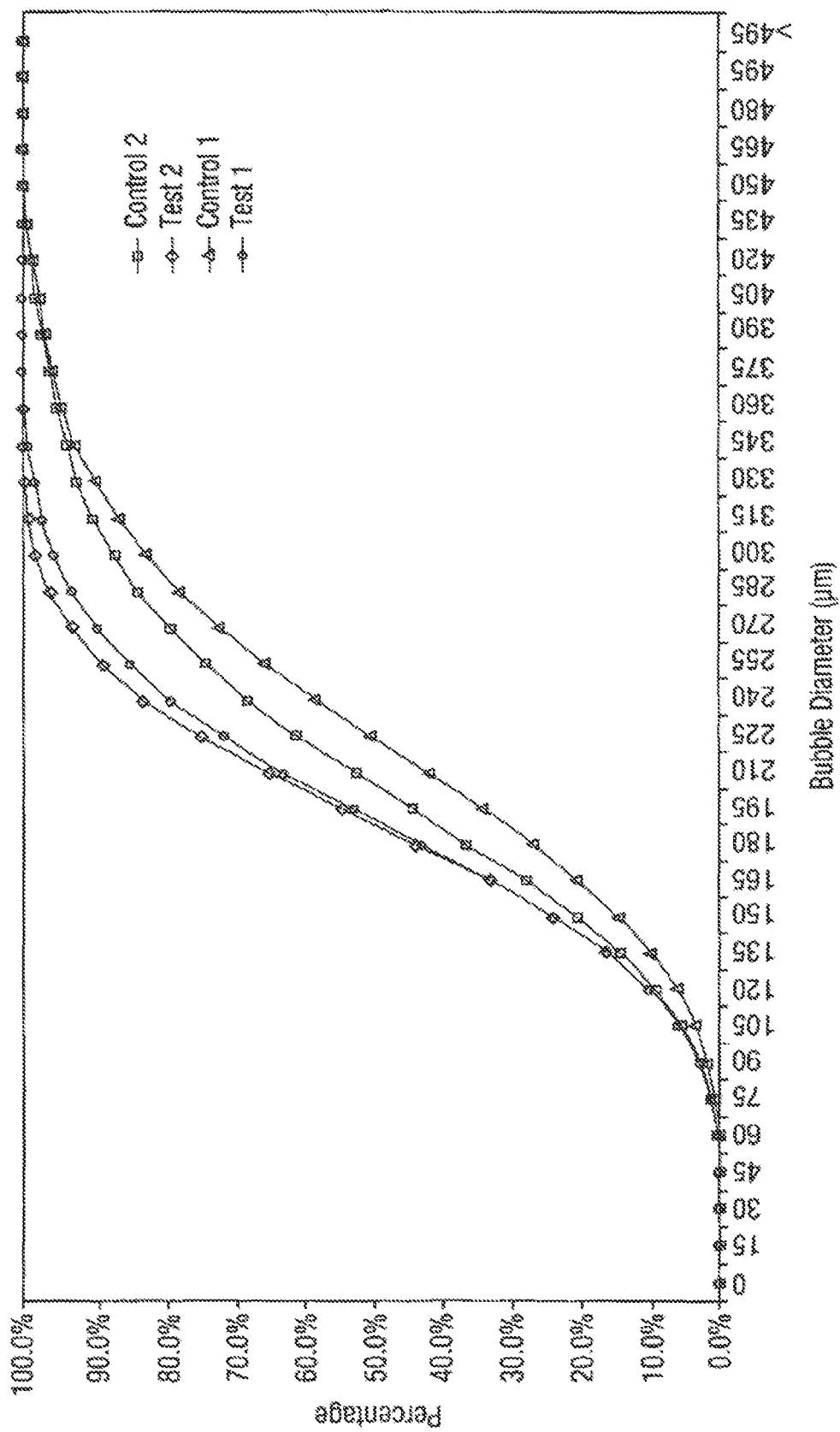

FIG. 20 shows a graph of the proportion of bubbles by diameter from the four bi-can conditions tested in below.

Figure 21:
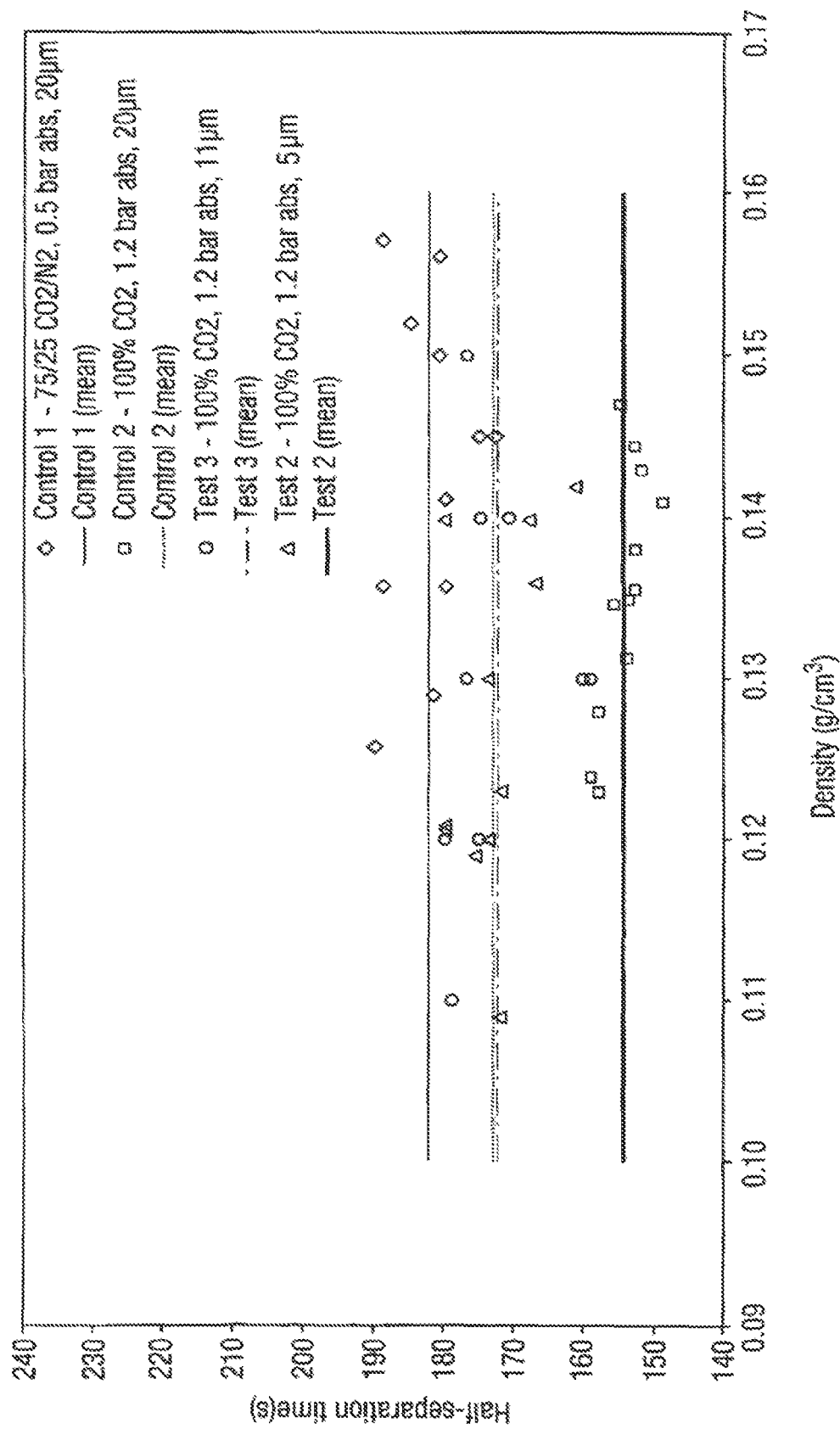

FIG. 21 shows a graph to compare the results from the four bi-can conditions tested below, showing the effect of shuttle mesh size on half-separation time and density.

Figure 22A:
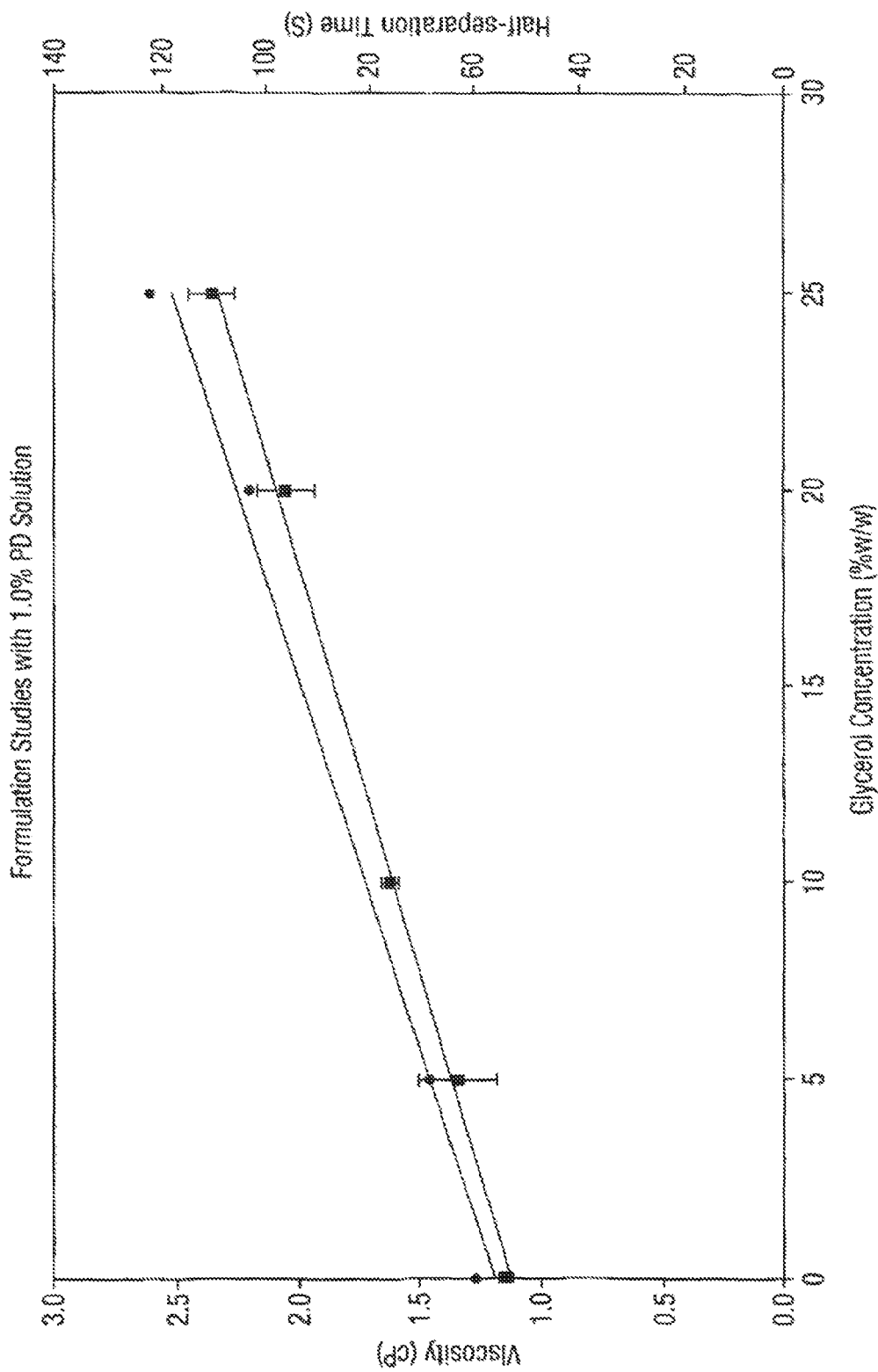
Figure 22B:
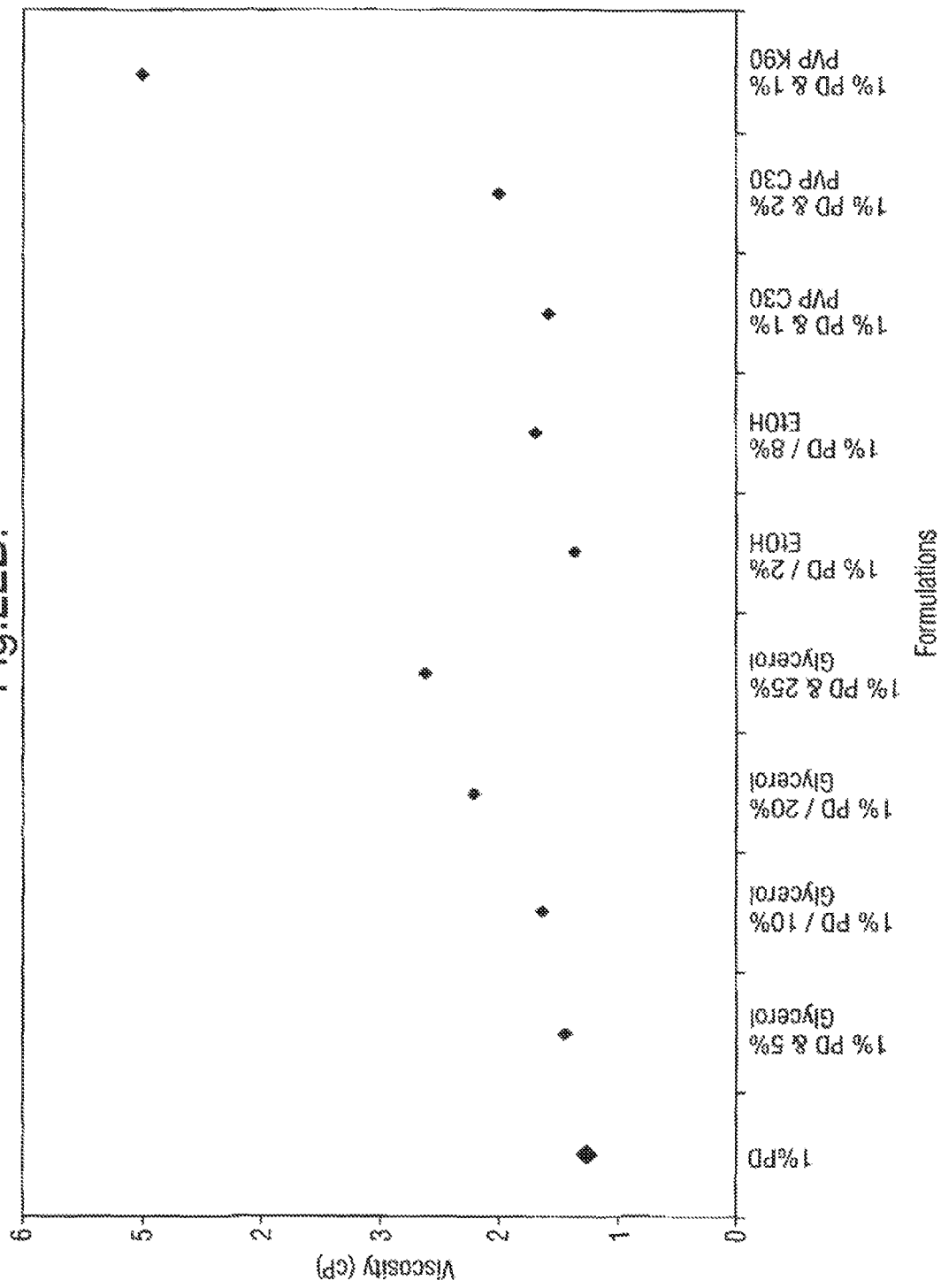

FIG. 22 shows the effects of (a) glycerol concentration on viscosity of the liquid phase before mixing with the gas phase to form a foam and (b) the effects of various viscosity enhancing agents on viscosity of the liquid phase.

Figure 23A:
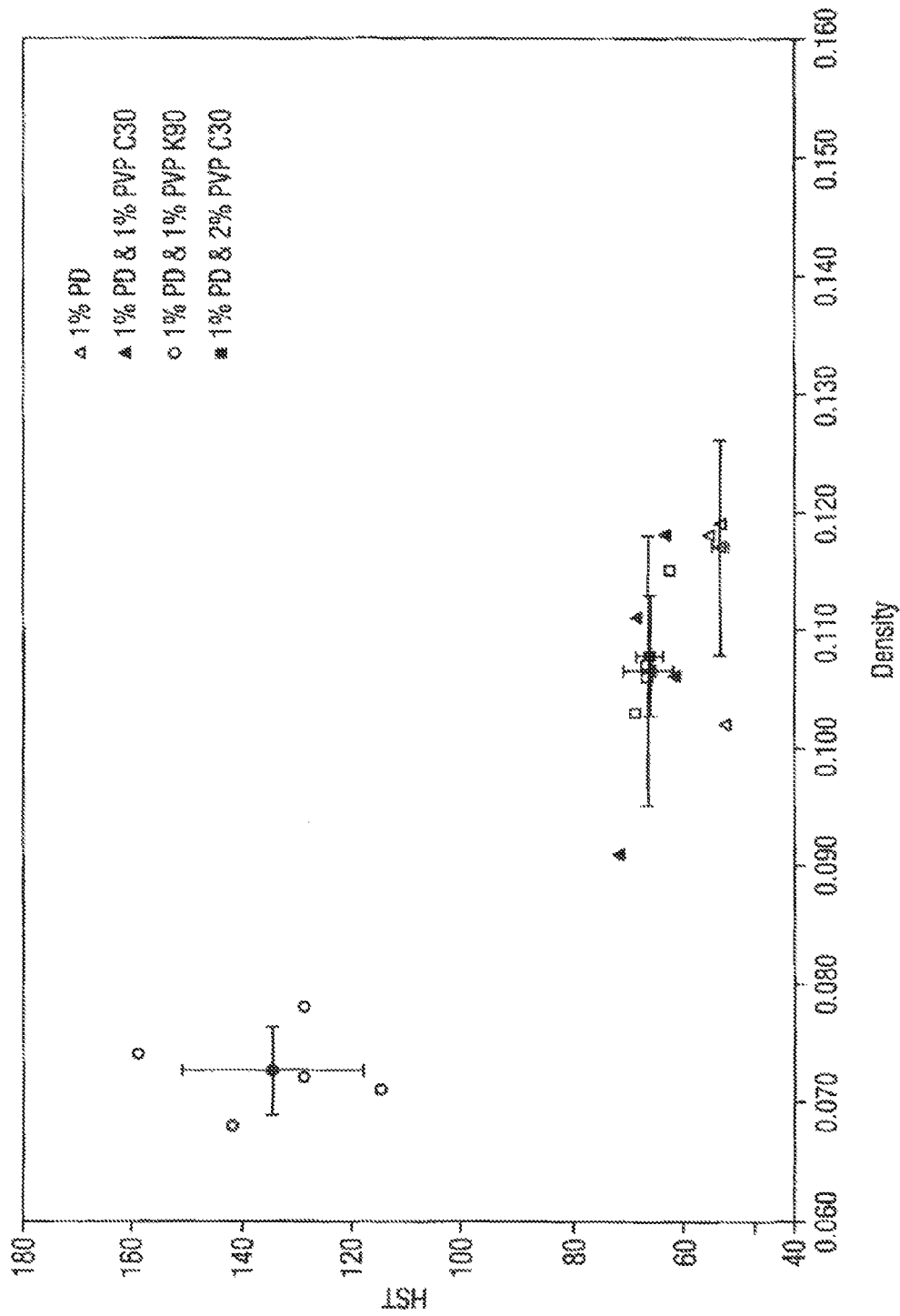
Figure 23B:
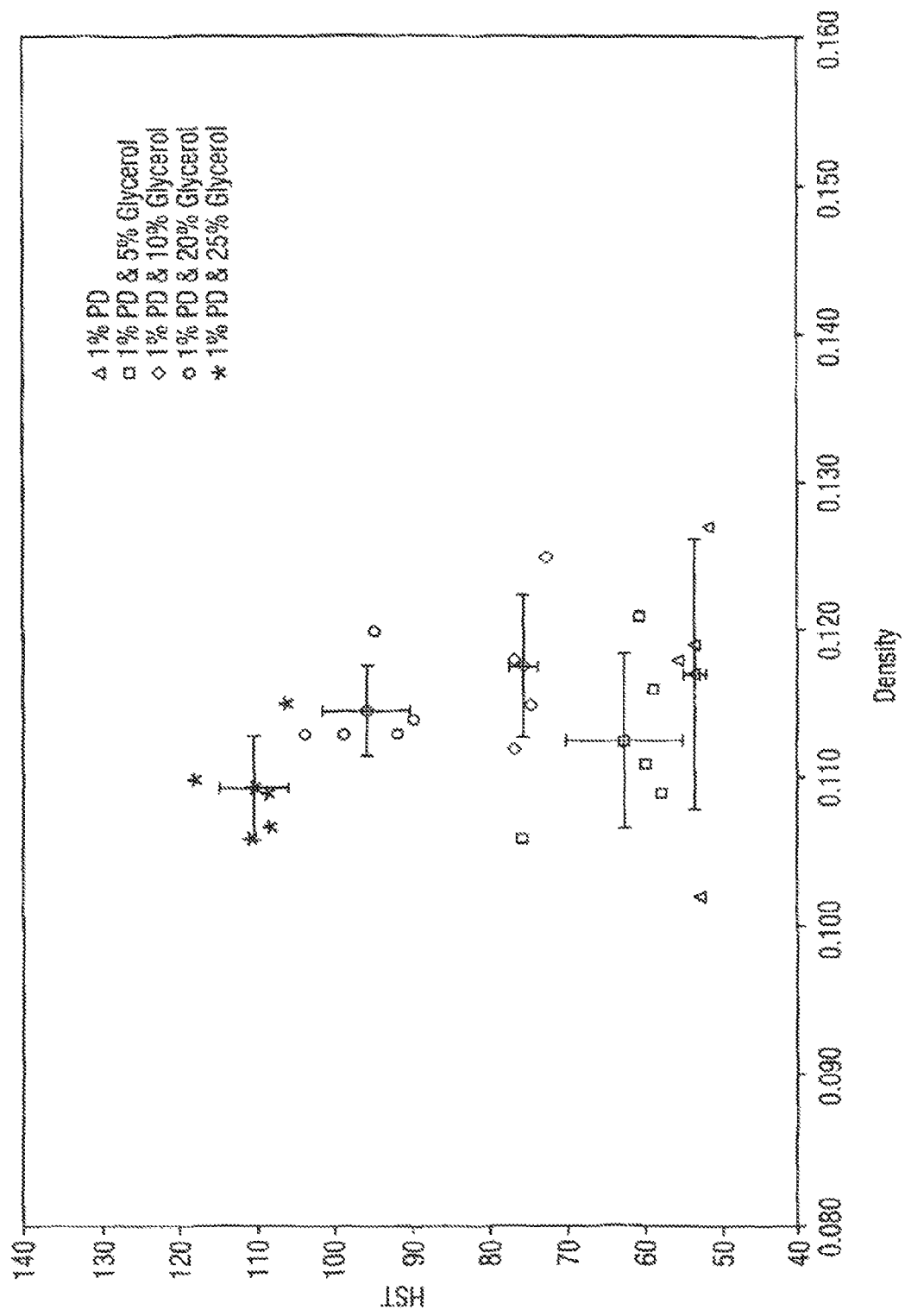
Figure 23C:
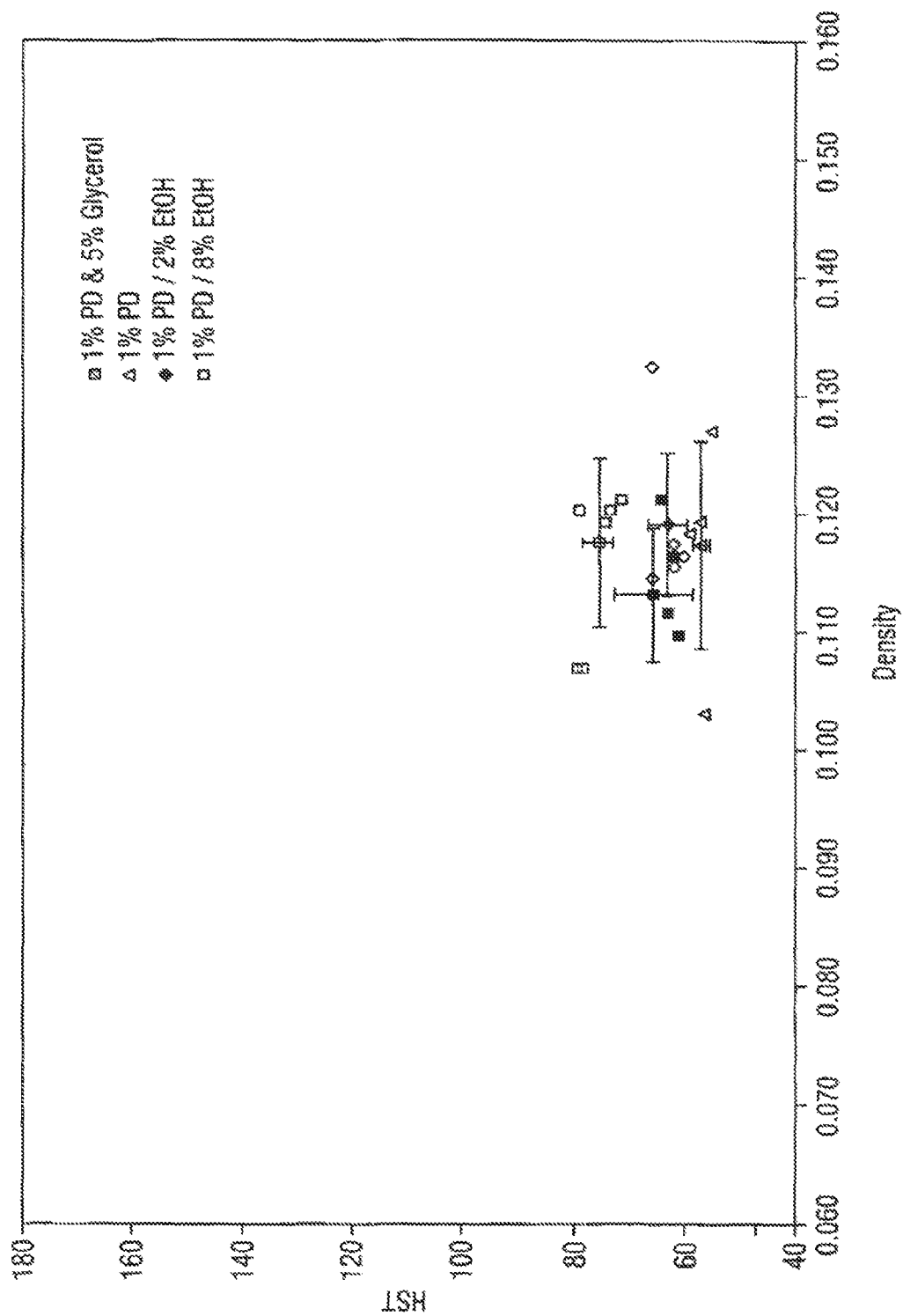

FIG. 23(a, b, and c) shows the effects of various viscosity enhancing agents on the density and half life of a Cabrera foam.

DETAILED DESCRIPTION

For the purpose of this application terms have the following definitions: A sclerosant liquid is a liquid that is capable of sclerosing blood vessels when injected into the vessel lumen. Scleropathy or sclerotherapy relates to the treatment of blood vessels to eliminate them. An aerosol is a dispersion of liquid in gas. A major proportion of a gas is over 50% volume/volume. A minor proportion of a gas is under 50% volume/volume A minor amount of one liquid in another liquid is under 50% of the total volume. Atmospheric pressure and bar are 1000 mbar gauge. Half-life of a foam is the time taken for half the liquid in the foam to revert to unfoamed liquid phase.

In one embodiment, the foam is such that 50% or more by number of its gas bubbles of 25 µm diameter and over are no more than 200 µm diameter.

Half-life is conveniently measured by filling vessel with a known volume and weight of foam and allowing liquid from this to drain into a graduated vessel, the amount drained in a given time allowing calculation of half-life i.e. of conversion of foam back into its component liquid and gas phases. This is preferably carried out at standard temperature and pressure, but in practice ambient clinic or laboratory conditions will suffice.

As used here, the viscosity is determined by Brookfield DVII+Pro made by Brookfield Engineering Labs at room temperature.

In one embodiment, the gas/liquid ratio in the mix is controlled such that the density of the foam is 0.09 g/mL to 0.16 g/mL, more preferably 0.11 g/mL to 0.14 g/mL.

In another embodiment, the foam has a half-life of at least 100 seconds, such as for example, 2 minutes, 2.5 minutes, and 3 minutes. The half-life may be as high as 1 or 2 hours or more, but is preferably less than 60 minutes, more preferably less than 15 minutes and most preferably less than 10 minutes.

In one embodiment, the mixture of gas and sclerosant liquid is in the form of an aerosol, a dispersion of bubbles in liquid or a macrofoam. By macrofoam is meant a foam that has gas bubbles that are measured in millimeters largest dimension, e.g. approximately 1 mm and over, and over such as can be produced by lightly agitating the two phases by shaking. In another embodiment, the gas and liquid are provided in the form of an aerosol where a source of pressurized gas and a means for mixing the two is provided to the point of use. It may be that a macrofoam is first produced where the liquid and gas are brought together only at the point of use.

The ratio of gas to liquid used in the mixture may be important in order to control the structure of the foam produced such that its stability is optimized for the procedure and the circumstances in which it is being carried out. For some foams, one may mix 1 gram sclerosant liquid with from approximately 6.25 to 14.3 volumes (STP), more preferably 7 to 12 volumes (STP), of gas.

In one embodiment, the physiologically acceptable blood dispersible gas comprises a major proportion of carbon dioxide and/or oxygen. In some embodiments, the foam may comprise a minor proportion of nitrogen. While a proportion of nitrogen may be present, as in air, the present invention provides for use of carbon dioxide and/or oxygen without presence of nitrogen.

In one form the gas used is a mixture of carbon dioxide and other physiological gases, particularly containing 3% vol/vol or more carbon dioxide, such as from 10 to 90% carbon dioxide, such as from 30 to 50% carbon dioxide. The other components of this gas may be oxygen.

Another form of gas comprises 50% vol/vol or more oxygen, the remainder being carbon dioxide, or carbon dioxide, nitrogen and trace gases in the proportion found in atmospheric air. One gas is 60 to 90% vol/vol oxygen and 40 to 10% vol/vol carbon dioxide, another is 70 to 80% vol/vol oxygen and 30 to 20% vol/vol carbon dioxide. One embodiment is 99% or more oxygen.

Preferably the sclerosing agent is a solution of polidocanol or sodium tetradecylsulfate in an aqueous carrier, e.g. water, particularly in saline. More preferably the solution is from 0.5 to 5% v/v polidocanol, preferably in sterile water or a physiologically acceptable saline, e.g. in 0.5 to 1.5% v/v saline. Concentration of sclerosant in the solution will be advantageously increased for certain abnormalities such as Klippel-Trenaunay syndrome.

Polidocanol is a mixture of monolauryl ethers of macrogols of formula $C_{12}C_{25}(OCH_2CH_2)_nOH$ with an average value of n of 9, it will be realized that mixtures with other alkyl chains, oxyalkyl repeat units and/or average values of n might also be used, e.g. 7 to 11, but that 9 is most conveniently obtainable, e.g. from Kreussler, Germany, e.g. as Aethoxysklerol™, a dilute buffered solution of polidocanol.

The concentration of sclerosant in the aqueous liquid is a 1-3% vol/vol solution, such as polidocanol, in water or saline, such as about 1% vol/vol. The water or saline also, in some cases at least, contain 2-4% vol/vol physiologically acceptable alcohol, e.g. ethanol. Saline may be buffered. Some buffered saline is phosphate buffered saline. The pH of the buffer may be adjusted to be physiological, e.g. from pH 6.0 to pH 8.0, more preferably about pH 7.0.

The sclerosant may also contain additional components, such as stabilizing agents, e.g. foam stabilizing agents, e.g. such as glycerol. Further components may include alcohols such as ethanol.

In one embodiment, ranges for the gaseous nitrogen volume at are 0.0001% to 0.75%, such as 0.7%, such as 0.6%, and such as 0.5%. Although from a theoretical viewpoint it may be desirable to eliminate as much nitrogen as possible, it is also understood that since we live in an atmosphere of 80% nitrogen there are difficulties in consistently making a foam with a very high degree of purity with regard to nitrogen gas. Accordingly, the lower end for the range of nitrogen impurity which is preferable (from the point of view of being easier and/or less expensive to manufacture) is 0.0005%, more preferably 0.001%, still more preferably 0.005%, 0.01%, 0.05%, 0.1%, 0.2%, 0.3% or 0.4%. As will be apparent from the examples below, each incremental increase in the lower end of the range may result in a purifying step being taken out of the manufacturing procedure, with resulting cost savings.

Also according to the invention is provided a canister system adapted to dispense a foam and whose contents consist of a liquid phase and a gas phase, wherein the liquid phase comprises a sclerosing agent and the gas phase consists of a minor proportion of nitrogen gas and a major proportion of other gas, preferably physiologically acceptable gas, such that the gas phase of a foam produced by the canister system consists of between 0.0001% and 0.8% nitrogen gas. The other possible ranges for the nitrogen gas component, as recited above, also apply.

It will be appreciated that the term "canister system" can mean either a single canister containing a liquid and a gas for dispensing to generate a foam, or a two canister arrangement as described above, where gas is stored in one canister and liquid, optionally together with gas, in another.

In one embodiment, said minor proportion of nitrogen gas in the canister is also 0.0001% to 0.8% by volume of the total gas volume in the canister, or optionally the other ranges recited above.

In another embodiment, the canister includes an element through which the liquid and gas contents pass in order to dispense foam. In one embodiment, this element has apertures of approximately 0.1 to 15 micron diameter, more preferably 1-7 micron, still more preferably about 5 micron.

Another aspect of the present invention is a method for producing a foam suitable for use in scleropathy of blood vessels, particularly veins, characterized in that it comprises passing a mixture of gas and an aqueous sclerosant liquid through one or more passages having at least one cross-sectional dimension of from 0.1 to 15 µm, the ratio of gas to liquid being controlled such that a foam is produced having a density of between 0.07 g/mL to 0.19 g/mL and a half-life of at least 100 seconds, such as 2 minutes, such as 2.5 minutes.

Preferably, the said one or more passages have at least one cross-sectional dimension of from 1-7 micron, more preferably about 5 micron.

In accordance with the original specification (as set out in WO0072821-A1) the foam is preferably such that 50% or more by number of its gas bubbles of 25 µm diameter and over are no more than 200 µm diameter. Again in accordance with the original specification in WO00/72821-A1, preferably the method provides a foam characterised in that at least 50% by number of its gas bubbles of 25 µm diameter and over are of no more than 150 µm diameter. More preferably at least 95% of these gas bubbles by number are of no more than 280 µm diameter. Still more preferably at least 50% by number of these gas bubbles are of no more than 130 µm diameter and still more preferably at least 95% of these gas bubbles by number are of no more than 250 µm diameter.

In one embodiment, the gas comprises from 1% to 50% carbon dioxide, preferably from 10% to 40%, more preferably from 20% to 30%. Surprisingly, it has been found that by using a smaller aperture size for the mesh, foams having the specification set out in WO00/72821-A1 can be made with gas mixtures having higher proportions of carbon dioxide and correspondingly lower proportions of insoluble gases such as nitrogen. Carbon dioxide may be a desirable component of the gas mixture due to its extreme solubility, greater than that of oxygen.

Also according to the invention a method for angiologic treatment comprises injecting an effective amount of a sclerosing foam whose gaseous component consists of between 0.001% and 0.8% by volume gaseous nitrogen, the balance being other gas, preferably physiologically acceptable gas. The other possible ranges recited above for the percentage of nitrogen apply and the options for the other gases recited above apply.

Preferably the method of treatment comprises the injection of 10 ml to 50 ml of foam In a single injection, preferably 15 ml to 50 ml, more preferably 20 ml to 50 ml, still more preferably 30 ml to 50 ml of foam.

According to the invention a method of treatment of the human greater saphenous vein comprises treating substantially the entire greater saphenous vein of one leg with a single injection of foam as described above.

According to the invention a method of treatment of a blood vessel of diameter 7 mm or greater so as to cause damage to the endothelium of the vessel comprises injecting foam as described above.

A further factor in the inventors' developing understanding of the behaviour in blood of bubbles comprising soluble gases is the phenomenon of nitrogen diffusing out of blood and adjacent tissues and into the bubbles due to a difference in the partial pressure of nitrogen in the bubbles as compared with that in the surrounding blood and tissues. This phenomenon will generally only occur when the partial pressure of nitrogen in the bubble is lower than that in the surrounding blood and tissues.

It appears that carbon dioxide, and to a lesser extent oxygen, will diffuse out of the bubble and go into solution in the surrounding blood relatively very quickly, so that the bubble will quite quickly reach a point where the partial pressure of nitrogen in the bubble will be higher than that in the surrounding blood and tissues and, ultimately, the bubble will become substantially pure nitrogen. As soon as the nitrogen partial pressure gradient is reversed, nitrogen will come out of the bubble and into solution in the blood, though this will happen relatively slowly because of the low solubility of nitrogen. This phenomenon will also be influenced by increasing saturation of the surrounding blood with nitrogen, if this occurs to a significant extent. This phenomenon potentially affects the partial pressure gradient of nitrogen in the blood and may also mean that a limit for dissolution of nitrogen is reached if the surrounding blood becomes fully saturated with nitrogen.

It is not at present understood to what extent localised saturation of blood with nitrogen is a factor in the dissolution of the bubbles in a dispersing foam. Since the bloodstream in constant motion, however, it is assumed that this effect will only ever be transient and will not unduly affect the overall picture of nitrogen dissolution.

It appears that the initial phase of rapid dissolution of carbon dioxide and/or oxygen is critical: the shorter this period, the smaller the volume of nitrogen which is able to diffuse into the bubble.

There are several possibilities for eliminating residual bubbles or reducing them in size and/or number (apart from reducing the initial quantity of nitrogen in the gas phase of the foam). One of these is to make the bubbles as small as is practical. The smaller the bubble, the faster the carbon dioxide and/or oxygen will dissolve out of the bubble and therefore the shorter the time available for nitrogen from the blood to diffuse into the bubble before the partial pressure gradient for nitrogen reverses in favour of nitrogen diffusing out of the bubble.

Another is that of the patient breathing oxygen or air enriched with oxygen, which has the effect of increasing the oxygen partial pressure in the blood at the expense of the nitrogen partial pressure. This technique is known in the fields of diving and space exploration, where it has been used to reduce the risk of the "bends", i.e. the tendency on depressurisation for nitrogen to come out of solution in body tissues (as opposed to the blood in blood vessels which is what we are concerned with here). As far as the inventors are aware, it has never previously been proposed to use this technique in connection with injecting gases into the vascular system.

According to an aspect of the invention a sclerosant foam is composed of bubbles of which, ignoring bubbles of 1 micron or less diameter, 95% or more are of 150 micron diameter or less and 50% or more are of 100 micron diameter or less. Preferably, 95% or more of the bubbles are of 100 micron diameter or less and 50% or more of the bubbles are of 50 micron diameter or less. More preferably, 95% or more of the bubbles are of 75 micron diameter or less and 50% or more of the bubbles are of 30 micron diameter or less. Still more preferably, 95% or more of the bubbles are of 60 micron diameter or less and 70% or more of the bubbles are of 30 micron diameter or less. Examples are presented below showing how foams with these sorts of bubble distributions have been made.

These very small bubble foams have only to date been obtained by the inventors by having a relatively dense formulation of the order of 0.3 to 0.5 g/ml, with a relatively high ratio of liquid to gas. Such a wet foam is still considerably less dense than blood and therefore will be buoyant when in a vein full of blood. It is speculated that this buoyant characteristic may to some extent be responsible for the advantageous behaviour of foam in the vascular system in terms of displacing blood. However, the dense foams produced to date by the inventors behave essentially as a liquid in terms of their rheological properties—they are not "stiff".

It is not impossible that these dense but somewhat fluid foams may have a sufficiently good therapeutic effect to be useful and may also eliminate or reduce the residual gas problem. However, it is probable that the rheological properties of the foam in blood are important, and that a "stiff" foam is desirable effectively to displace blood and thus allow consistent, uniform application of the active to the interior of the vessel wall. For this reason it may be desirable to add a further ingredient to the foam in order to increase its stiffness/viscosity, either by adding a viscosity-enhancing additive to the formulation or by adding an agent which increases the foaming capacity of the formulation.

Such ingredients could be, without limitation, Polysorbate 20, Polysorbate 80 or Polygeline. Alternatively, glycerol and PVP may be added.

A foam with a bubble size distribution falling within the definitions set out above may be created by passing gas and liquid repeatedly through a fine mesh, e.g. a 5 micron mesh. Repeated passages through the mesh reduce the bubble size, though there appears to be a limit on this.

It its envisaged that other known techniques for agitating a gas and liquid mixture at high energy could be applied to make even finer bubbles. For example sonic or ultrasonic agitation of a mixing stream of gas and liquid could be used, or alternatively a mixture of beating the gas and liquid by mechanical means, supplemented by the application of sonic or ultrasonic energy.

The inventors have also prepared a foam having an average bubble size in the range 50 micron to 80 micron by adapting a canister to alter the ratio of liquid and gas being passed through a mesh.

A further aspect of the invention is a pressurised canister product adapted to dispense a sterile gas and sclerosing liquid mixture in predetermined proportions into a syringe, as a solution to some of the issues with extemporaneous preparation of foam. Thus a pressurised canister is provided—which may be of any suitable material such as anodised aluminium or even glass—containing sterile gas and sclerosing liquid and arranged to dispense the correct volume of liquid and gas into syringe. It is envisaged that the canister would contain sterile gas with a very low nitrogen concentration etc. as defined above. The canister may have a pierceable septum for puncturing with a hypodermic needle, or it may have a break seal which is arranged to be broken by insertion of a syringe luer nozzle.

In the latter case, a syringe luer nozzle could be inserted into the canister in a sealing fashion, with the syringe nozzle pointing upwards. Liquid in the canister would be dispensed first under pressure, followed by equalisation of the pressure in the canister and syringe. The pressure and volume of gas in the canister could of course be arranged so that the correct proportions of gas and liquid are dispensed. Alternatively, the canister could be provided with an internal dip tube so that the same effect is achieved with the canister in an upright orientation.

Also according to the invention is provided a method of preparing a sclerosing foam which includes the step of cooling the ingredients of the foam to a sub-ambient temperature prior to generation of the foam. A suitable temperature range might be 0 to 15 degrees Celsius, preferably 0 to degrees, more preferably 3 to 7 degrees. Decreasing temperature increases liquid viscosity and, in this way, the inventors believe the half life of the foam could be extended. Since, during decay of a foam, the bubble size tends to increase, this methodology may help reduce the average size of bubbles over time in the body and thereby reduce residual bubbles.

Also according to the invention, and in line with the reasoning presented earlier, a method of angiologic treatment of a patient comprises causing the patient to breathe oxygen gas or oxygen-enriched air for a predefined period prior to injection of foam as described above. Preferably the predefined period is 1 to 60 minutes, more preferably 1-20 minutes, more preferably 5-10 minutes.

Another embodiment of the present invention provides a foam, that, for example, can be used in the elimination of blood vessels and vascular malformations, that are made available by the method and devices of the invention, comprising a physiologically acceptable gas that is readily dispersible in blood together with an aqueous sclerosant liquid wherein in that the foam has a density of from 0.07 to 0.19 g/ml.

In one embodiment, the foam is capable of being passed down a 21 gauge needle without reverting back to gas and liquid by more than 10%, based on liquid content reverting back to unfoamed liquid phase.

Half-life is conveniently measured by filling vessel with a known volume and weight of foam and allowing liquid from this to drain into a graduated vessel, the amount drained in a given time allowing calculation of half-life i.e. of conversion of microfoam back into its component liquid and gas phases. This is preferably carried out at a standard temperature and pressure, but in practice ambient clinic or laboratory conditions will suffice.

Most conveniently the funnel is pre-equilibrated in a water bath to ensure a temperature of 25° C. before drying and application of foam. Placing of a foam filed syringe upside down, without its plunger, above the funnel leading into a graduated receptacle allows convenient measurement of this parameter.

In one embodiment, the foam, on passage through said needle, does not revert back to unfoamed liquid by more than 5% based on liquid content, still more preferably by no more than 2%. This is measured by measuring the change in volume of the foam versus the liquid.

In one embodiment, the foam is capable of being passed down a needle while retaining at least 50% by number of its gas bubbles of at least 25 µm diameter at no more than 200 µm diameter. This is conveniently measured under ambient conditions, more preferably at STP.

In one embodiment, the gas includes less than 40% v/v nitrogen. Preferably the density of the foam is from 0.09 to 0.16 g/mL, more preferably 0.11 g/mL to 0.14 g/mL.

In one embodiment, the foam density, which is a measure of liquid/gas ratio, is from 0.13 to 0.14 g/ml and the half-life is at least 2.5 minutes. The foam more preferably does not move outside of its parameters of bubble size set out above in such time.

In one embodiment, the gas consists of at least 50% oxygen or carbon dioxide, more preferably 75% or more oxygen or carbon dioxide and most preferably at least 99% oxygen or carbon dioxide, e.g. substantially 100% oxygen or carbon dioxide. Preferably the oxygen or carbon dioxide is medical grade.

As discussed above, addition of glycerol to the aforesaid sclerosant imparts a longer half-life to the resultant foam. However, glycerol may increase density and also produces a tendency for the meshes to block up when using a mesh device as described above, so should be used carefully where the device it is produced from may be used multiple times or the bag-on-valve concept is used.

The invention also provides:

a method of treating a patient in need of sclerotherapy of a blood vessel comprising administering a foam as described above to that blood vessel; use of a foam described above for the manufacture of a medicament for sclerotherapy; and a foam as described above for use in therapy.

Accordingly the one aspect of the present invention provides a method for producing a foam suitable for use in scleropathy of blood vessels, particularly veins, characterized in that it comprises passing a mixture of a physiologically acceptable blood dispersible gas and an aqueous sclerosant liquid through one or more passages having at least one cross-sectional dimension of from 0.1 to 15 µm, the ratio of gas to liquid being controlled such that a foam is produced having a density of between 0.07 g/mL to 0.19 g/mL and a half-life of at least 100 seconds.

Apparatuses for Generating Foam

There are a number of issues with the current practice of extemporaneous preparation of foam, the use of air as the gas being only one of these. Other issues are the consistency of the product, which is by nature highly variable because it depends on the physician selecting the gas to liquid ratio and then pumping the gas and air mixture a given number of times and/or at a given speed to obtain the right product. Foams are highly variable and different bubble sizes and densities will have different safety and efficacy profiles.

Very recently, a machine has been made available which is designed to receive two syringes and apply a given number of pumps at a given rate to achieve a roughly consistent product. The machine is called "Turbofoam"® but the inventors are not at present aware who is marketing the machine. Two syringes are loaded into it (one of which is loaded with sclerosant solution). When activated, the machine automatically draws a predetermined quantity of atmospheric gas into the syringes and cycles the syringes until a foam of the desired properties is made.

Clearly, the arrangement described above addresses at least the issues of reproducibility of the foam as regards the gas/liquid ratio (provided the correct amount of liquid is loaded initially by the user) and also the number and speed of cycles. However, it is obviously also quite inconvenient in many respects and sterility may also be compromised by build up of bacteria in the gas channels of the machine, for example.

The solution proposed by the inventors is to provide a sterile pack containing one or two syringes, optionally together with any connectors etc. The syringe or syringes is/are pre-loaded with the correct volumes of gas and sclerosing liquid. Most syringes are made from plastics material such as polypropylene which allows gas to permeate through it over time. Therefore, the packaging is preferably substantially gas-impermeable and the atmosphere in the pack is preferably substantially the same composition as the gas pre-loaded into the syringe. This sort of packaging is well known in itself and examples include metallised plastic sheeting e.g. an aluminium and polyethylene laminate.

According to one aspect of the invention, there is provided a substantially sterile pack comprising:

a syringe charged with a liquid sclerosing agent and a gas mixture comprising physiologically acceptable gas, such as, for example, between 0.0001% and 0.8% gaseous nitrogen with the balance being other gas, such physiologically acceptable gas; and a gas atmosphere inside the pack having substantially the same composition as the said gas mixture in the syringe.

In one embodiment, the gas mixture consists of 0.001% to 0.8% gaseous nitrogen, preferably 0.01% to 0.8%, more preferably 0.01% to 0.7%, still more preferably 0.01% to 0.6%.

In one embodiment, the said other gas is oxygen, carbon dioxide or a mixture thereof. Optionally, a small percentage (e.g. 0.1 to 5%) of a tracer gas, which is not found in significant amounts in the atmosphere, is added to allow leaks to be detected. Such a gas might be e.g. helium, neon, argon, xenon or any other gas which is found in trace concentrations (0.01%) in atmospheric air.

To avoid contamination, the pack contents may be at slightly above atmospheric pressure. This may be achieved by manufacturing the pack at an ambient temperature below standard room temperature. Once the pack enters normal ambient surroundings, the temperature increase of the atmosphere inside the pack will ensure a slight overpressure.

Manufacture of the packaged product would be carried out in aseptic conditions, using techniques standard in that field.

This pre-packaged product may include one syringe of the type comprising a barrel, a first plunger and a second plunger, the second plunger having an apertured plunger head which is adapted to be movable within the barrel independently of the first plunger.

Alternatively the syringe may be a conventional one, containing an appropriate amount of gas as described above. A further syringe containing sclerosing agent could be provided in the same or a different pack, together with the connectors, three way valves, etc necessary to perform any of the known techniques for extemporaneous foam preparation.

In use, the pack is opened and the usual technique followed for generating foam, without the need to measure out liquid or gas. In the case of a two syringe technique, the syringes can be supplied ready connected, to increase convenience and remove a potential source of contamination.

Optionally, the pack may include a syringe connector which incorporates a fine mesh with apertures of 1-200 micron, preferably 2 to 50, more preferably 3 to 20 micron maximum dimensions. Alternatively, if a single syringe device is used, the apertures in the plunger may be provided by a mesh with pores of these proportions.

Optionally, the package could constitute a cartridge for a foam generating machine similar to the "Turbofoam"® described above.

A further solution to the issues with extemporaneous foam preparation has been proposed by the inventors. This is to provide a pressurised canister—which may be of any suitable material such as anodised aluminium or even glass—containing sterile gas and sclerosing liquid and arranged to dispense the correct volume of liquid and gas into a syringe. It is envisaged that the canister would contain sterile gas as defined above. The canister may have a pierceable septum for puncturing with a hypodermic needle, or it may have a break seal which is arranged to be broken by a syringe luer nozzle.

In the latter case, a syringe luer nozzle could be inserted into the canister in a sealing fashion, with the syringe nozzle pointing upwards. Liquid in the canister would be dispensed first under pressure, followed by equalisation of the pressure in the canister and syringe. The pressure and volume of gas in the canister could of course be arranged so that the correct proportions of gas and liquid are dispensed. Alternatively, the canister could be provided with an internal dip tube so that the same effect is achieved with the canister in an upright orientation.

It is found that passing a stream of the sclerosant liquid and the gas under pressure through one or more passages of 0.1 μm to 15 μm as described provides a stable blood dispersible gas based sclerosant injectable foam that was previously thought to be only producible by supply of high amounts of energy using high speed brushes and blenders.

The aerosol, dispersion or macrofoam is preferably produced by mixing the gas and liquid from respective flows under pressure. The mixing conveniently is carried out in a gas liquid interface element such as may be found in aerosol canisters. The interface device may however be very simple, such as a single chamber or passage of millimeter dimensions, i.e. from 0.5 to 20 mm diameter, preferably 1 to 15 mm diameter, into which separate inlets allow entry of gas and liquid. Conveniently the interface is of design which is commonly found in aerosol canisters but which is selected to allow the correct ratio of gas to liquid to allow formation of a foam of the presently defined density. Suitable inserts are available from Precision Valves (Peterborough UK) under the name Ecosol and are selected to produce the ratio specified by the method above.

However, the mixing of gas and liquid may also be brought about within a dip-tube leading from the sclerosant solution located in the bottom of a pressurized container where holes in the dip-tube allow gas to enter into a liquid stream entering from the bottom of the tube. In this case the holes may be of similar diameter to the Ecosol holes. Such holes may be conveniently produced by laser drilling of the dip-tube.

The one or more passages through which the aerosol or macrofoam so produced are passed to produce the stable foam preferably have diameter of from 4 μm to 22 μm, more preferably from 5 μm to 11 μm where simple passages are provided, such as provided by openings in a mesh or screen, e.g. of metal or plastics, placed perpendicular to the flow of gas/liquid mixture. The passage is conveniently of circular or elliptical cross section, but is not necessarily so limited. A number of such meshes or screens may be employed along the direction of flow.

Most preferably the passages are provided as multiple openings in one or more elements placed across the flow. Preferably the elements are from 2 to 30 mm diameter, more preferably 6 to 15 mm diameter, face on to the flow, with 5 to 65% open area, e.g. 2% to 20% open area for woven meshes and 20% to 70% open area for micro porous membranes. Openings in a porous material, such as provided in a perforated body, preferably provide several hundreds or more of such passages, more preferably tens or hundred of thousands of such passages, e.g. 10,000 to 500,000, presented to the gas liquid mixture as it flows. Such material may be a perforated sheet or membrane, a mesh, screen or sinter. Still more preferably a number of sets of porous material are provided arranged sequentially such that the gas and liquid pass through the passages of each set. This leads to production of a more uniform foam.

Where several elements are used in series these are preferably spaced 1 to 5 mm apart, more preferably 2 to 4 mm apart e.g. 3 to 3.5 mm apart. For some embodiments of the present invention it is found that the passage may take the form of a gap between fibres in a fibrous sheet placed across the path of the gas/liquid flow, and the dimension described in not necessarily the largest diameter, but is the width of the gap through which the gas/liquid aerosol or macrofoam must flow.

Alternatively the method provides for passing the mixture of gas and liquid through the same set of passages, e.g. as provided by one or more such porous bodies, a number of times, e.g. from 2 to 2,000, more preferably 4 to 200 times, or as many times as conveniently results in a foam of the required bubble size distribution set out above. It will be realized that the more times the foam passes through the meshes, the more uniform it becomes. Where multiple passes through the meshes are possible, a large mesh size may be desirable, e.g, 20 to 300 μm, such as 40 to 200 μm, such as 60 to 150 μm.

The pressure of the gas used as it is passed through the passages will depend upon the nature of the mechanism used to produce the foam. Where the gas is contained in a pressurized chamber and passes only once through the mesh, such as in an aerosol canister, in contact with the liquid, suitable pressures are typically in the range 0.01 to 9 bar over atmosphere. For use of meshes, e.g. 1 to 8 meshes arranged in series, having apertures of 10-20 μm diameter, 0.1 to 5 atmospheres over bar will, inter alia, be suitable. For use of 3-5 meshes of 20 μm aperture it is found that 1.5-1.7 bar over atmospheric is sufficient to produce a good foam. For a 0.1 μm pore size membrane, a pressure of 5 bar or more over atmospheric pressure is preferred.

In one preferred form of the Invention the passages are in the form of a membrane, e.g. of polymer such as polytetrafluoroethylene, wherein the membrane is formed of randomly connected fibres and has a rated effective pore size which may be many times smaller than its apparent pore size. A particularly suitable form of this is a biaxially oriented PTFE film provided by Tetratec™ USA under the trademark Tetratex™, standard ratings being 0.1 to 10 μm porosity. Preferred pore sizes for the present method and devices are 3 to 7 μm. This material may be laminated with a porous backing material to give it strength and has the advantage that one pass through may be sufficient to produce a foam that meets the use requirements set out above with regard to stability. However, it will evident to those skilled in the art that use of more than one such membrane in series will give a still more uniform foam for given set of conditions.

It is believed that the combination of provision of a stream of solution and gas under pressure through an aerosol valve and then flow through the passages, e.g. pores in a mesh, screen, membrane or sinter provides energy sufficient to produce a stable aqueous liquid soluble gas, e.g. carbon dioxide and/or oxygen, based sclerosant foam that was previously thought to be only producible by supply of high amounts of energy using high speed brushes and blenders as described in the prior art.

A most preferred method of the invention provides a housing in which is situated a pressurisable chamber. For sterile supply purposes this will at least partly filled with a sterile and pyrogen free solution of the sclerosing agent in a physiologically acceptable aqueous solvent but otherwise may be charged with such at the point of use. This convenient method provides a pathway by which the solution may pass from the pressurisable chamber to exterior of the housing through an outlet and more preferably a mechanism by which the pathway from the chamber to the exterior can be opened or closed such that, when the container is pressurized, fluid will be forced along the pathway and through one or more outlet orifices.

The method is particularly characterized in that the housing incorporates one or more of (a) a pressurized source of the physiologically acceptable gas that is readily dispersible in blood, and (b) an inlet for the admission of a source of said gas; the gas being contacted with the solution on activation of the mechanism.

The gas and solution are caused to pass along the pathway to the exterior of the housing through the one or more, preferably multiple, passages of defined dimension above, through which the solution and gas must pass to reach the exterior, whereby on contact with, e.g. flow through, the passages the solution and gas form a foam.

Preferably the gas and liquid pass through a gas liquid interface mechanism, typically being a junction between a passage and one or more adjoining passages, and are converted to an aerosol, dispersion of bubbles or macrofoam before passing through the passages, but as explained they may be converted first to a macrofoam, e.g. by shaking of the device, e.g., by hand, or mechanical shaking device.

In another aspect of the present invention there is provided a device for producing a foam suitable for use in scleropathy of blood vessels, particularly veins, comprising a housing in which is situated a pressurisable chamber containing a solution of the sclerosing agent in a physiologically acceptable solvent referred to in the first aspect; a pathway with one or more outlet orifices by which the solution may pass from the pressurisable chamber to exterior of the device through said one or more outlet orifices and a mechanism by which the pathway from the chamber to the exterior can be opened or closed such that, when the container is pressurized and the pathway is open, fluid will be forced along the pathway and through the one or more outlet orifices said housing incorporating one or more of (a) a pressurized source of physiologically acceptable gas that is dispersible in blood and (b) an inlet for the admission of said gas; the gas being in contacted with the solution on activation of the mechanism such as to produce a gas solution mixture said pathway to the exterior of the housing including one or more elements defining one or more passages of cross sectional dimension, preferably diameter, 0.1 µm to 15 µm, through which the solution and gas mixture is passed to reach the exterior of the device, said passing of said mixture through the passages forming a foam of from 0.07 to 0.19 g/mL density and of half-life at least 2 minutes.

Preferably the apparatus includes a chamber, e.g. such as in a sealed canister, charged with the blood dispersible gas and the sclerosant liquid, e.g. in a single chamber, the device pathway including a dip tube with an inlet opening under the level of the liquid in this chamber when the device is positioned upright. Preferably the dip-tube has an outlet opening at a gas liquid interface junction where the gas, which resides in the chamber above the liquid, has access to the pathway to the device outlet. The pathway is opened or closed by a valve element which is depressed or tilted to open up a pathway to the exterior of the device, whereby the liquid rises up the dip tube under gas pressure and is mixed in the interface junction with that gas to produce an aerosol, dispersion of bubbles in liquid or macrofoam.

Either inside the pressurisable chamber disposed in the pathway to the valve, or on the downstream side of the valve, is provided an element having the one or more passages described in the first aspect mounted such that the gas liquid mixture, i.e. dispersion of bubbles in liquid, aerosol or macrofoam, passes through the passage or passages and is caused to foam. This element may conveniently be located in a cap on the canister in between the valve mounting and an outlet nozzle. Conveniently depression of the cap operates the valve. Alternatively the element is within the canister mounted above the gas liquid interface.

In an alternate embodiment of this device the gas liquid interface may comprise holes in the dip tube above the level of the liquid in the canister inner chamber.

The gas pressure employed will be dependent upon materials being used and their configuration, but conveniently will be 0.01 to 9 bar over atmospheric, more preferably 0.1-3 bar over atmospheric, and still more preferably 1.5-1.7 bar over atmospheric pressure.

A preferred device of this aspect of the invention is of the 'bag-on-valve' type. Such device includes a flexible gas and liquid tight container, forming a second inner chamber within the pressurisable chamber, which is sealed around the dip-tube and filled with the liquid. More preferably the dip-tube has a one-way valve located at a position between its end located in the sclerosant liquid and the gas liquid interface junction, which when the passage to the exterior is closed, remains closed such as to separate the liquid from the physiologically acceptable blood dispersible gas around it in the chamber. On opening the pathway to the exterior, the one way valve also opens and releases liquid up the dip-tube to the gas liquid interface where an aerosol is produced which is in turn then passed through the passages to be converted to foam. A suitable one-way valve is a duck-bill type valve, e.g. such as available from Vernay Labs Inc, Yellow Springs, Ohio, USA. Suitable bag-on-valve can constructions are available from Coster Aerosols, Stevenage, UK and comprise an aluminium foil/plastics laminate.

Conveniently the one way valve is located at the top of the dip-tube between that and the gas liquid interface junction, i.e. an Ecosol device. This allows filling of the bag before application of the one way valve, followed by sterilization of the contents, whether in the canister or otherwise.

Such a preferred device has several potential advantages. Where oxygen is the gas, this is kept separate from the liquid before use and thus reduces possibility of oxygen radicals reacting with organic components in the liquid, e.g. during sterilization processes such as irradiation. Where carbon dioxide is the gas, storage can lead to high volumes of gas dissolving in the liquid, which on release to the atmosphere or lower pressure, could out-gas and start to destroy the foam too quickly. Such separation also prevents the deposition of solidified sclerosing agent components in the dimension sensitive orifices of the device in an unused can in storage or transit, particularly should that be oriented other than upright.

It is preferred that the gas liquid interface is provided as a defined orifice size device such as the Ecosol device provided by Precision Valve Peterborough UK. For a device where the passages of defined dimension are outside of the pressurized chamber, i.e. mounted on the valve stem, the ratio of area of the gas holes to the liquid holes should be of the order of 3 to 5, preferably about 4. Where the passages are inside the pressurized chamber this is preferably higher.

Another aspect of the invention provides a device for producing a foam suitable for use in sclerotherapy of blood vessels, particularly veins, comprising a housing in which is situated a pressurisable chamber, at least part filled or tillable with a solution of a sclerosing agent in a physiologically acceptable solvent and/or a physiologically acceptable blood dispersible gas; a pathway by which the contents of the chamber may be passed to exterior of the housing through one or more outlet orifices and a mechanism by which the chamber can be pressurized such that its contents pass to the exterior along the pathway and through one or more outlet orifices said pathway to the exterior of the housing or the chamber including one or more elements defining one or more passages of cross sectional dimension, preferably diameter, 0.1 µm to 15 µm through which the contents of the chamber may be passed, whereby on passing through the passages the solution and gas form a foam of from 0.07 to 0.19 g/mL density and having a half-life of at least 2 minutes.

The elements defining the passages in the pathway or chamber may be static or may be moveable by manipulation of the device from outside of its interior chamber.

Preferably the housing is a container defining a chamber in which is situated the solution and gas under pressure and the pathway is a conduit leading from the chamber in the interior of the container to a valve closing an opening in the container wall.

Preferred forms of the one or more elements defining the multiple passages for use in the device of the present invention are meshes, screens or sinters. Thus one or more meshes or perforated screens or sinters will be provided, with some preferred forms employing a series of such elements arranged in parallel with their major surfaces perpendicular to the path of solution/gas expulsion.

It is preferred that all elements of any of the devices according to the invention having a critical dimension are made of a material that does not change dimension when exposed to aqueous material. Thus elements with such function such as the air liquid interface and the element defining the passages of 0.1 µm-15 µm dimension preferably should not be of a water swellable material such as Nylon 66 where they are likely to be exposed to the solution for more than a few minutes. Where such exposure is likely these parts are more preferably being fashioned from a polyolefin such as polypropylene or polyethylene.

Preferably the canister is sized such that it contains sufficient gas and solution to form up to 500 mL of foam, more preferably from 1 mL up to 200 mL and most preferably from 10 to 60 mL of foam. Particularly the amount of gas under pressure in such canisters should be sufficient to produce enough foam to treat, i.e. fill, at least one varicosed human saphenous vein. Thus preferred canisters of the invention may be smaller than those currently used for supply of domestic used mousse type foams. The most preferred canister device is disposable after use, or cannot be reused once opened such as to avoid problems of maintaining sterility.

It may be preferred to incorporate a device which maintains gas pressure in the canister as foam is expelled. Suitable devices are such as described under trademarked devices PECAP and Atmosol. However, where a significant headspace or pressure of gas is provided this will not be necessary.

The canister system has some drawbacks, however. It is relatively complex and thus expensive. Furthermore, the initial quantity of foam generated using a canister system can be of unpredictable quality and thus tends to be diverted off to waste prior dispensing foam for use. It is not easy to deliver foam direct from a pressurized canister into a cannula in a patient's vein; although this is theoretically possible, it would require special valve/control arrangements on the canister output to allow for the delivery rate to be highly controllable by the clinician administering the treatment. A further issue is that, whenever dispensing of foam is stopped or slowed significantly, it is necessary on re-starting to divert a quantity of foam to waste again before dispensing usable foam.

For all these reasons, the canister product mentioned above, though a well designed and highly effective system, is designed to deliver foam product into a syringe for subsequent administration to a patient. A special foam transfer unit is used for this purpose. The syringe nozzle is inserted into a port on this transfer device and the device is then used to divert the first portion of foam before charging the syringe with usable foam.

A further issue is that the foam, once made, immediately starts to change—liquid drains out and bubbles coalesce. A period of time is required time for the clinician to divert an initial quantity of foam from a canister, charge a syringe with good foam, connect it to a line to a patient's vein and administer the foam. This time will vary with different clinicians and even the same clinician will not always take the same length of time. Furthermore, each treatment is different and the foam will be injected over a different period; sometimes the clinician will stop dispensing foam for a short period and then recommence. All this time, the properties of the foam will be changing.

There are other techniques for generating foam for use in sclerotherapy, including the so called "Tessari" and "DSS" techniques, each of which involves pumping liquid sclerosant and gas between two syringes. These two techniques are widely used for generating sclerosing foams made with air, and there are also a number of other less widely used techniques. Although these techniques are simpler than a canister system, they offer no solutions to the problems mentioned above and they also have their own problems such as unpredictability of the product and the difficulty in using any gas other than ambient air.

The inventors realized that it would be desirable to have a device which could be connected directly to the patient and would generate foam as it was needed, so that the foam had the minimum possible time to degrade before entering a patient's vein. Ideally the device would also not have the problem of producing an initial quantity of poor foam. The device should be suitable for containing a gas other than air for incorporation into the foam.

The inventors also realized that, particularly for a highly soluble gas, the device should ideally not store the gas together with the liquid under a pressure substantially greater than atmospheric. With a soluble gas, especially a highly soluble gas such as carbon dioxide, storing the gas and liquid under pressure can contribute to the speed of decay of the foam. This is because the pressurised gas tends to go into solution in the sclerosant liquid. On exit of the foam, the gas comes out of solution into the bubbles thereby accelerating degradation of the foam. Pressurising the gas also, of course, adds to the complexity and expense of the system.

According to a first aspect of the invention, a device for generating and dispensing foam for therapeutic use comprises:
(a) a housing;
(b) the housing having a first chamber of adjustable volume containing gas at substantially atmospheric pressure;
(c) the housing further having a second chamber of adjustable volume containing sclerosant solution;
(d) an outlet for dispensing the liquid and sclerosant solution in the form of a foam and a flow path communicating between the outlet and the said first and second chambers;
(e) the flow path including a region in which mixing of the gas and solution takes place;
(f) a foaming unit located downstream of the mixing region, the foaming unit having holes with a dimension transverse to the flow direction of between 0.1 and 100 micron.

It is preferred that the hole dimension be from 1 to 50 micron, more preferably 2 to 20 micron, still more preferably 3 to 10 micron. These holes may be provided by a mesh, perforated screen, sinter or fabric, for example. Although the shape and orientation of the holes may not be regular, the unit should have a major proportion (greater than 50%, preferably greater than 80%) of holes where at least one dimension in a direction approximately transverse to the flow should be in the ranges specified above.

In use, the volumes of the first and second chamber are adjusted in order to drive the gas and solution out of the chambers and through the mixing region and foaming unit. A mixture of gas and solution is formed as the gas and liquid pass through the mixing region and then a foam is formed as the mixture passes through the foaming unit.

It is preferable for the liquid and gas to be driven through the mixing region and foaming unit at a flow rate which falls within a predetermined range, the desired flow rate range depending on the characteristics of the liquid and of the gas, the characteristics of the mixing region and foaming unit, and possibly other characteristics of the system. The volume of the chambers may be varied manually to create the foam, but it is preferred that the adjustment of the chambers be carried out using some other source of motive power, e.g. an electric, clockwork, pneumatic or hydraulic motor or by the direct action of pressurized gas or even a simple spring. An on/off control is preferably provided for the user to commence and to stop delivery of foam.

The source of motive power may be provided as part of the device. Alternatively, the device may be designed as a cartridge for insertion into a delivery device which may for example be similar to known devices for automatically delivering medication from a syringe over an extended period of time.

The device may be configured with a flexible housing in form of e.g. a bag with dual chambers, or two separate bags, connected to a mixing region and foaming unit. The bag or bags may then be rolled up in a delivery device or the contents squeezed out by some other mechanical means. Desirably, the chambers are of a size and shape which allow them to be squeezed out at the same rate, in terms of velocity, to achieve a desired foam density. This allows the mechanical means for squeezing the chambers to be of a more simple design.

Alternatively the device may be configured as a syringe, with the first and second chambers having respective plungers which may be depressed in order to expel the contents. Preferably size and shape of the chambers, most notably their cross sectional areas, are selected so that the plungers may be driven at the same speed to achieve a desired ratio of gas to liquid in the foam.

As discussed above, the device may be suitable for connection to a cannula needle, optionally via a line, for delivery of foam into the body, e.g. into a vessel such as a blood vessel, especially a varicose vein or other venous malformation. Since the foam is generated by the same action which expels the foam from the outlet, it may be possible to connect the cannula to the outlet of the device and administer foam to a patient at the same time as generating it. This is clearly a much simpler procedure than generating the foam, drawing it up into a syringe, connecting the syringe to a line/cannula and then administering the foam.

According to the invention, a method for administering a foam to the human body, e.g. into a vessel such as a blood vessel, especially a varicose vein or other venous malformation, comprises the steps of: (a) sclerosant foam generating device to a cannula needle inserted into a patient; and (b) operating the device to generate and dispense foam to the patient. Specifically, the steps may include:
(a) connecting a device as described above to a cannula needle inserted into a patient;
(b) adjusting the volume of the said first and second chambers so as to generate and deliver foam to the patient.

A further advantage of the generation and delivery of the foam in a single step is that the foam has very little time to degrade prior to entering the body to perform its function, e.g. the sclerosis of a varicose vein. The device is therefore particularly suitable for generating foams with very soluble gases, such as carbon dioxide or nitrous oxide, which tend to revert to their gaseous and liquid phases relatively quickly.

Since the gas and liquid are stored in separate chambers until formation of the foam, there is very little possibility for the gas to become dissolved in the liquid, which tends to happen with the pressurized canister systems described in the prior art.

According to the invention, a foam is provided which is made with a sclerosant solution, e.g. polidocanol solution, and a gas, wherein, on creation of the foam, the dissolved level of the gas in the solution is not substantially higher than that of the solution when exposed to atmosphere at s.t.p., and wherein the gas is at least 70% by volume carbon dioxide, more preferably at least 90% carbon dioxide, still more preferably substantially 100% carbon dioxide. The gas may also include 0.1 to 50% oxygen. Alternatively the gas may be substantially 100% nitrous oxide or a mixture of nitrous oxide and carbon dioxide.

Also according to the invention, a device is provided for generating foam from a sclerosant liquid, e.g. polidocanol solution, and a soluble gas as described above, wherein the device incorporates a chamber in which the gas is stored at substantially atmospheric pressure. Preferably, the device further comprises a chamber in which sclerosant liquid is stored. Preferably, the device further includes a foaming unit for creating a foam from the gas and sclerosant liquid, the foaming unit having holes with a dimension transverse to the flow direction of between 0.1 and 100 micron, such as 1 to 50, 2 to 20, 3 to 11, and especially about 5.

Further features and advantages of the invention will be apparent from the following description of various specific embodiments, which is made with reference to the accompanying drawings.

Figure 1:
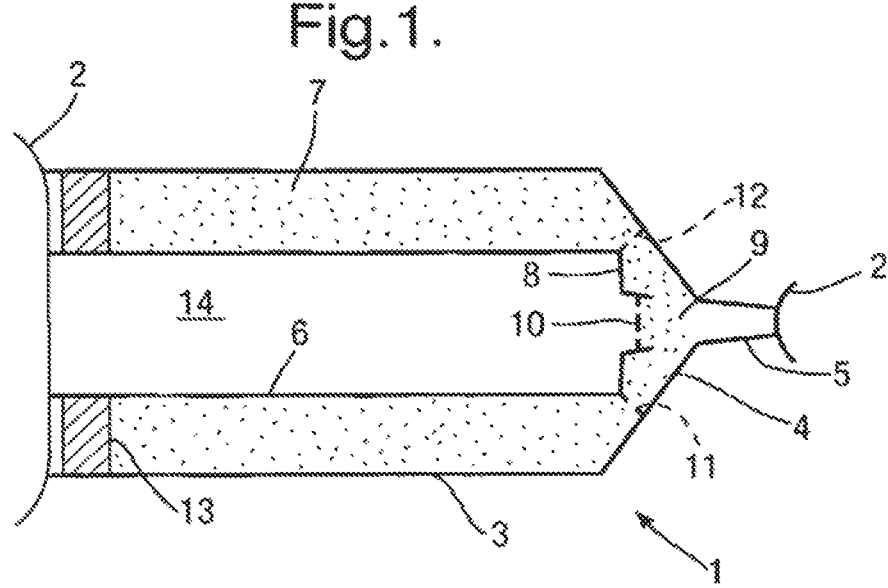
FIG. 1 is a schematic representation of a syringe barrel part of a first embodiment of device in accordance with the first aspect of the invention, showing it in a sealed state for storage.

One embodiment of a device according to the invention comprises a syringe type device comprising a syringe barrel having an annular chamber containing gas and a central chamber for receiving a cartridge of sclerosant solution, e.g. 1% polidocanol solution. FIG. 1 shows a syringe barrel 1 in a storage condition with its open ends closed with seals 2 of metal/plastic laminate material. The barrel 1 comprises an outer cylindrical wall 3 having a conical tapered end portion 4 at the front, from which extends a standard luer nozzle 5. Disposed within the outer cylindrical wall is an inner cylindrical wall 6 defining an inner chamber 14. The front of the inner wall 6 is partly closed by and end face 8, in which is formed an orifice 9 with a frangible seal 10. The inner wall is supported at the front end by a web 11, in which apertures 12 are formed.

The outer and inner walls 3, 6 define between them an annular space 7 which is filled with substantially 100% pure carton dioxide gas. The annular space 7 communicates with the interior space of the luer nozzle 5 via the apertures 12 in the web 11. Located at the rear of the barrel, in the annular space 7, is an annular plunger seal 13 of resilient plastics material which seals against the outer and inner cylindrical walls 3, 6.

Figure 2:
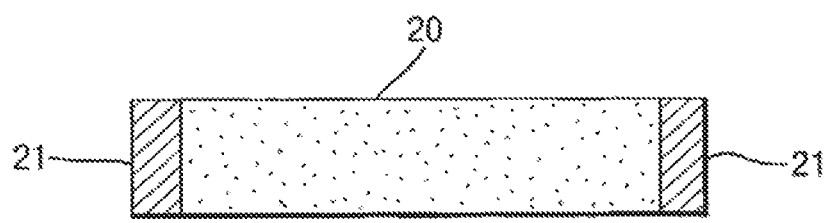
FIG. 2 is a schematic representation of a cartridge for use with the syringe barrel of FIG. 1.

FIG. 2 shows a cartridge comprising a glass tube 20 filled with 1% polidocanol and sealed at each and by a resilient plastics bung 21. One or both of the bungs may function as a plunger seal, that is to say it may be movable down the length of the tube whilst retaining a sealing contain with the interior wall of the tube. The cartridge of FIG. 2 is not suitable for use with the syringe barrel described above, but could be used with a modified version of the barrel as discussed below.

Figure 3:
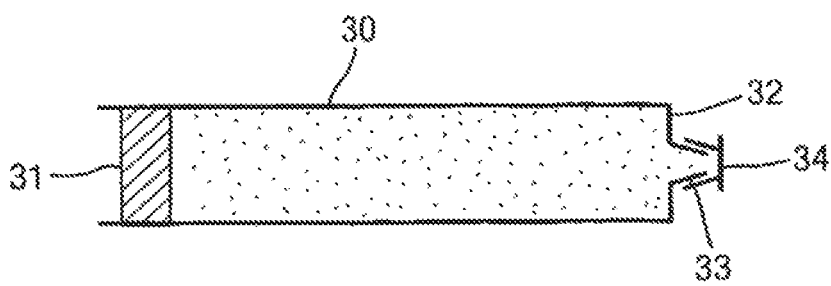
FIG. 3 is a schematic representation of a modified cartridge for use with the syringe barrel of FIG. 1.

FIG. 3 shows a cartridge suitable for use with the syringe barrel described above with reference to FIG. 1. The cartridge comprises a glass tube 30 which is filled with 1% polidocanol solution. At the rear end of the tube 30 is a resilient bung 31 which is capable of functioning as a plunger seal as described above. At the front end of the tube is an end face 32 in which is located a nozzle 33, sealed with an end cap 34. The size and shape of the tube 30 complements the shape of the inner wall 6 of the syringe barrel of FIG. 1. In particular, the diameter of the tube 30 is such that the tube is a close fit in the interior space 14 defined within the inner wall 6 of the barrel 1, and the nozzle 33 of the cartridge is sized so that, when fully inserted into the interior chamber 14 of the barrel, it protrudes through the orifice 9 in the front of the chamber 14 (the end cap 34 having first been removed).

Cartridges of the type shown in FIGS. 2 and 3 are well known for liquid drugs. The cartridges are fitted to specially designed injection devices to administer the drug, and the empty cartridge then removed from the device and disposed of.

Figure 4:
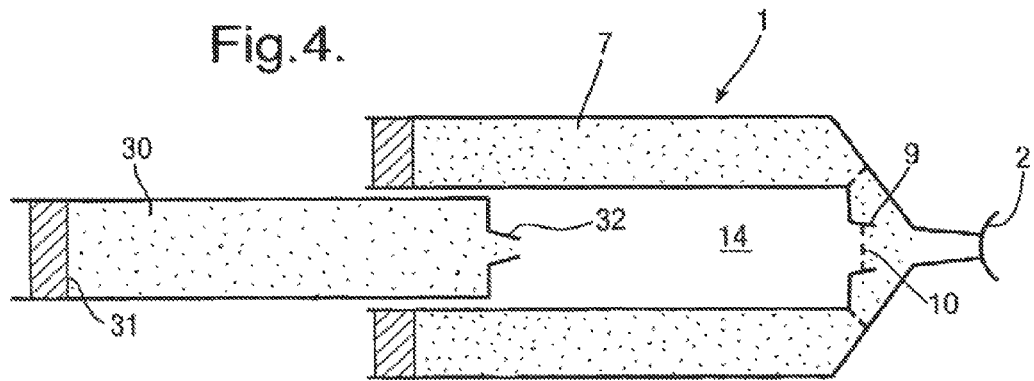
FIG. 4 is a further schematic representation of the syringe barrel of FIG. 1 with a cartridge of the type shown in FIG. 3 being installed.

FIG. 4 shows a cartridge 30 as shown in FIG. 3 being inserted into the barrel of FIG. 1. Note that the end cap 34 of the cartridge has been removed.

Figure 5:
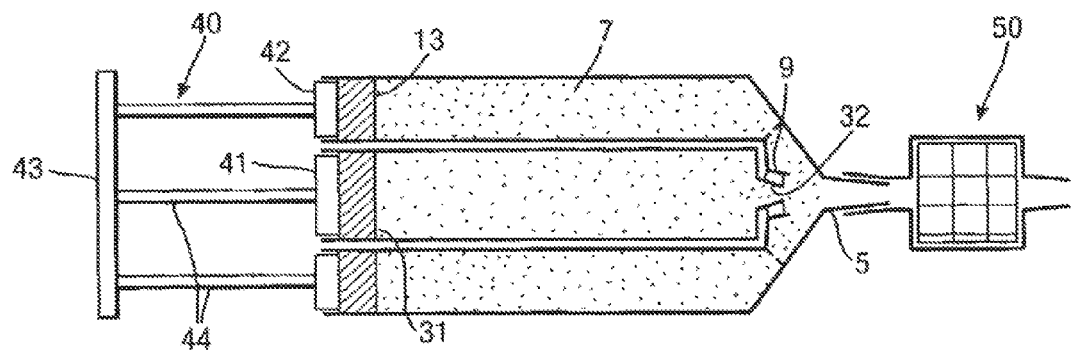
FIG. 5 is a further schematic representation of the syringe barrel of FIG. 1 with a foaming unit and plunger stem fitted.

FIG. 5 shows the cartridge 30 fully inserted into the barrel 1 such that the nozzle 32 seals in the orifice 9 of the interior chamber 14 of the barrel. A syringe plunger stem 40 is fitted to the rear of the syringe barrel 1. The plunger stem 40 comprises a disc 43 for applying manual pressure, connected via shafts 44 to a central disc shaped pressure pad 41 and an annular pressure pad 42. The pressure pads 41, 42 are engaged with bungs/plunger seats 31, 13, respectively, of the annular barrel chamber 7 and of the cartridge 30.

At the front of the barrel 1, a foaming unit 50 is fitted to the luer nozzle 5. The foaming unit comprises a stack of mesh elements with microscopic perforations. The foaming unit will be described in more detail below in relation to FIGS. 11, 12 and 13.

Figure 6:
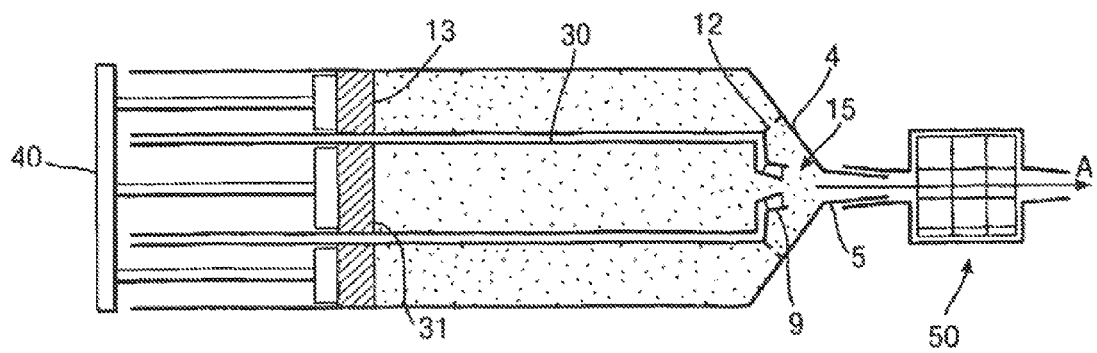
FIG. 6 is a schematic representation of the syringe, cartridge and foaming device of FIG. 5, with the plunger stem of the syringe partially depressed.
Figure 8:
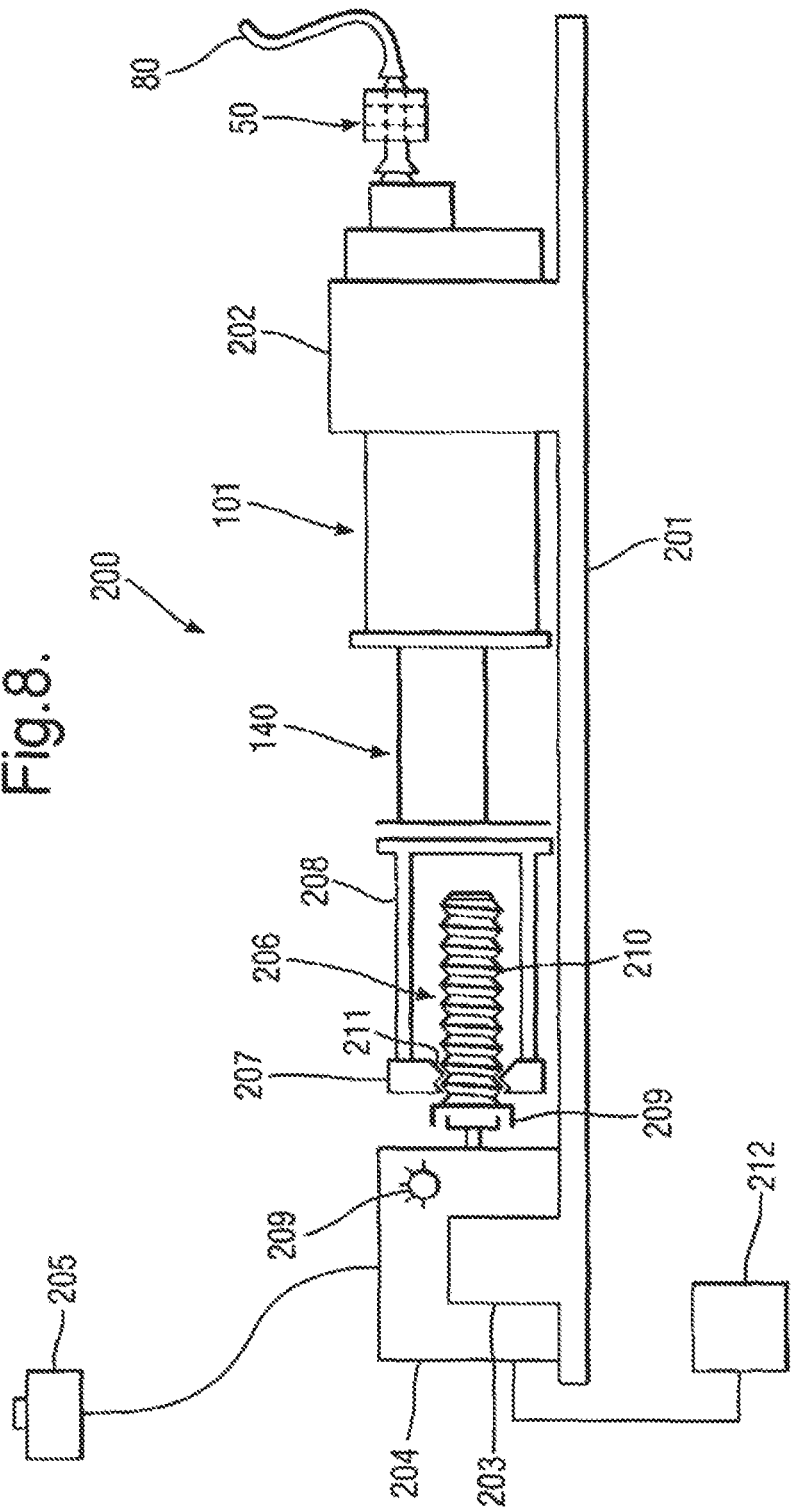
FIG. 8 is a schematic representation of the device of FIG. 7 installed in a syringe driver for generation and delivery of foam at a controlled rate.

In use, the plunger stem 40 is depressed either manually or in a syringe driver such as the one shown schematically in FIG. 8 and discussed below. The syringe with partly depressed plunger stern and foaming unit fitted is shown in FIG. 6. The plunger seals 13, 31 in the annular carbon dioxide chamber and in the chamber defined within the cartridge are advanced as the plunger stem is depressed, thereby driving carbon dioxide and polidocanol solution through the apertures 12 and the orifice 9. Mixing of the gas and liquid takes place in the region 15 in front of the orifice 9 where the annular gas flow interacts with the liquid flow. The mixture then proceeds as indicated by arrow A in FIG. 6 through the syringe nozzle 5 into the foaming unit 50 where the gas and liquid are passed through microscopic perforations of average dimension 5 micron to create a fine foam or foam with an average bubble size of around 100 micron.

Figure 7:
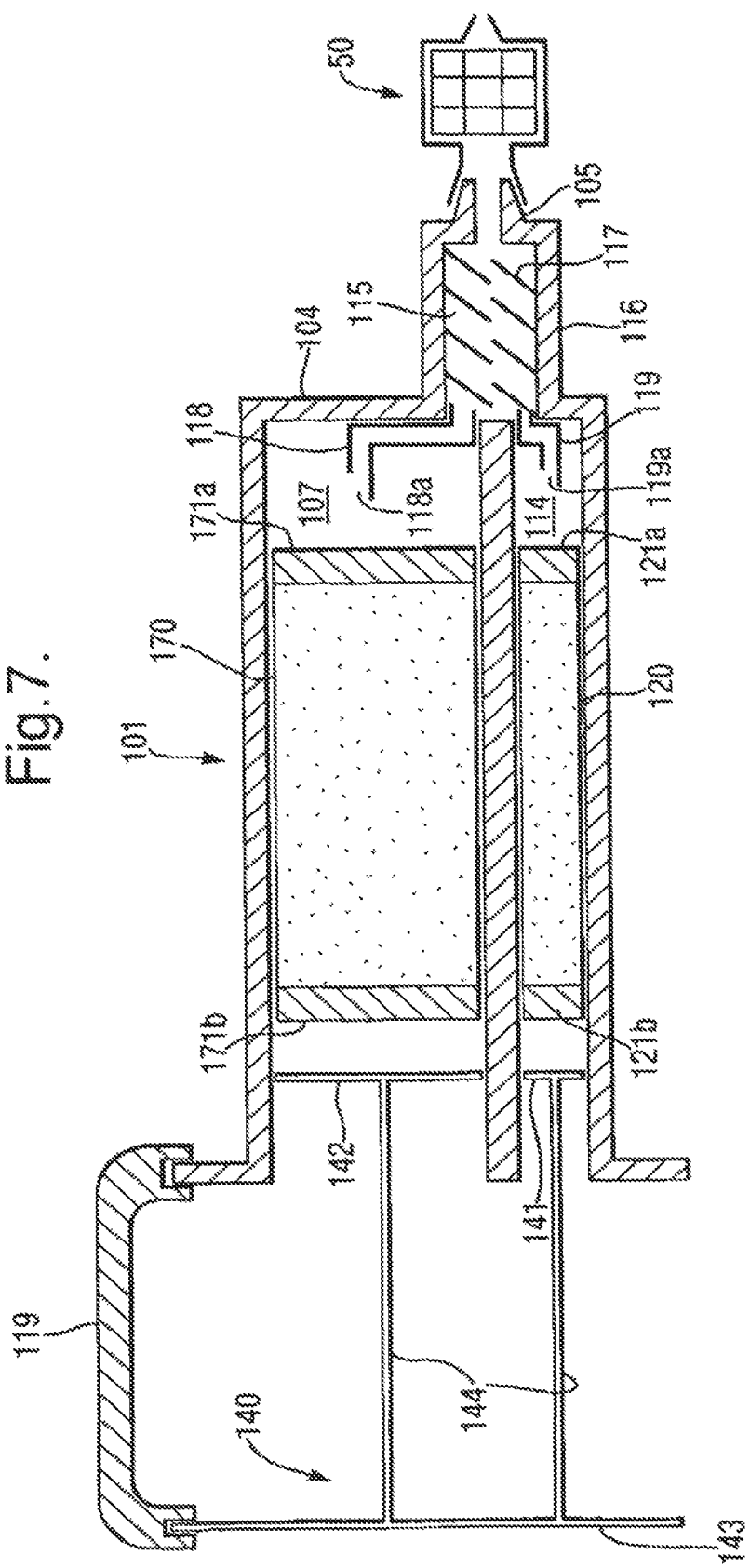
FIG. 7 is a schematic representation of a second embodiment of device in accordance with the first aspect of the invention, comprising charged syringe with foaming unit fitted.

FIG. 7 shows an alternative syringe-based design. A syringe barrel 101 houses twin parallel gas and liquid chambers 107, 114 which receive respective cartridges 170, 120 of the type shown in FIG. 2 with resilient bungs 171a, 171b, 121a, 121b at each end. The gas chamber 107 contains cartridge 170 which is filled with substantially 100% pure carbon dioxide at substantially atmospheric pressure. The liquid chamber 114 contains cartridge 120 which is filled with 1% polidocanol solution.

At the rear end of the barrel 101 a plunger stem is fitted, comprising a disc 143 for applying manual pressure, connected via shafts 144 to two disc shaped pressure pads 41, 42 received within the gas and liquid chambers 107, 114 respectively.

At the front end of the syringe barrel is an end wall 104 from which projects a cylindrical hub 116 with a nozzle 105 at the end. Within the hub 116 is a mixing chamber or mixing region 115. In this region are located static mixing fins 117. Located at the front of the chambers 107, 114 are hollow needle-like members 118, 119 respectively, each with a point 118a, 119a facing into the respective chamber. Each needle-like member is contoured to lie along the front face of its respective chamber and to extend into the mixing chamber 115.

Fitted to the nozzle 105 of the syringe is a foaming unit 50 of similar design to that used in the device of FIGS. 1 to 6. The foaming unit will be described more fully below with reference to FIGS. 11-13.

The syringe is supplied with cartridges 120, 170 pre-fitted. A clip 119 prevents depression of the plunger stem 140 until the clip is removed immediately prior to use. When it is desired to use the syringe, the clip 119 is removed and the plunger manually depressed so that the cartridges 120, 170, which are a snug fit in their respective chambers 114, 107, are advanced into contact with the needle elements 119, 118 respectively. Further depression of the plunger stem 140 causes the needle points 119a, 118a to penetrate the resilient bungs 121a, 171a at the front of the cartridges, thereby opening a communication channel between the interior of the cartridges and the mixing chamber 115.

Further depression of the plunger stem 140 causes carbon dioxide and polidocanol solution to flow together into the mixing chamber, in a ratio predetermined by the cross-sectional areas of the cartridges. Fins 117 in the mixing chamber ensure that the gas and liquid are thoroughly mixed prior to entering the foaming unit 50 where the liquid and gas is converted into a foam.

When treating a patient, the clinician would go through the above steps and ensure that consistent foam is being discharged from the foaming unit 50. Pressure is then released from the plunger stem 140 and a line from a cannula, which has previously been inserted into a vein to be treated, is connected by a standard luer fitting to the exit of the foaming unit. Pressure would then be applied again to the plunger stem 140 to produce foam and at the same time inject it through the line and cannula and into the patient's vein.

The exact properties of the foam will depend to some extent on the speed at which the plunger stem 140 is depressed. For this reason it is preferable that a syringe driver is used to administer the foam. A syringe driver is shown schematically in FIG. 8, with the syringe of FIG. 7 fitted in it. The driver 200 comprises a base 201, syringe clamp 202 and motor 204 fitted in a motor mounting 203. The motor 204 is coupled via a coupling 209 to a drive shaft 206 having an external thread 210. Received on the drive shaft is annular member 207 having an internal thread 211 engaged with the external thread 210 of the drive shaft. From the annular member 207 extends a driving member which bears on the plunger stem 140 of the syringe which is clamped in the syringe clamp 202.

The motor is connected to a DC power supply 212, has a speed calibration control 209 for setting the correct drive speed, and also an on/off control 205.

In use, the clinician would remove the clip 119 from the syringe of FIG. 7, depress the plunger stem 140 to the point where consistent foam is being produced, then insert the syringe into the driver and connect up to a line 80 previously installed in a patient's vein. The speed of the motor 204 would previously have been calibrated to a speed appropriate for the syringe being used. The clinician then has control of the delivery of foam to the patient by means of the on/off switch.

As short a line as possible is used, so that a very small quantity of foam resides in the line when the motor is switched off. In this way, it is ensured that almost all the foam delivered to the patient has been generated only a few moments previously and has had very little opportunity to degrade.

Figure 9:
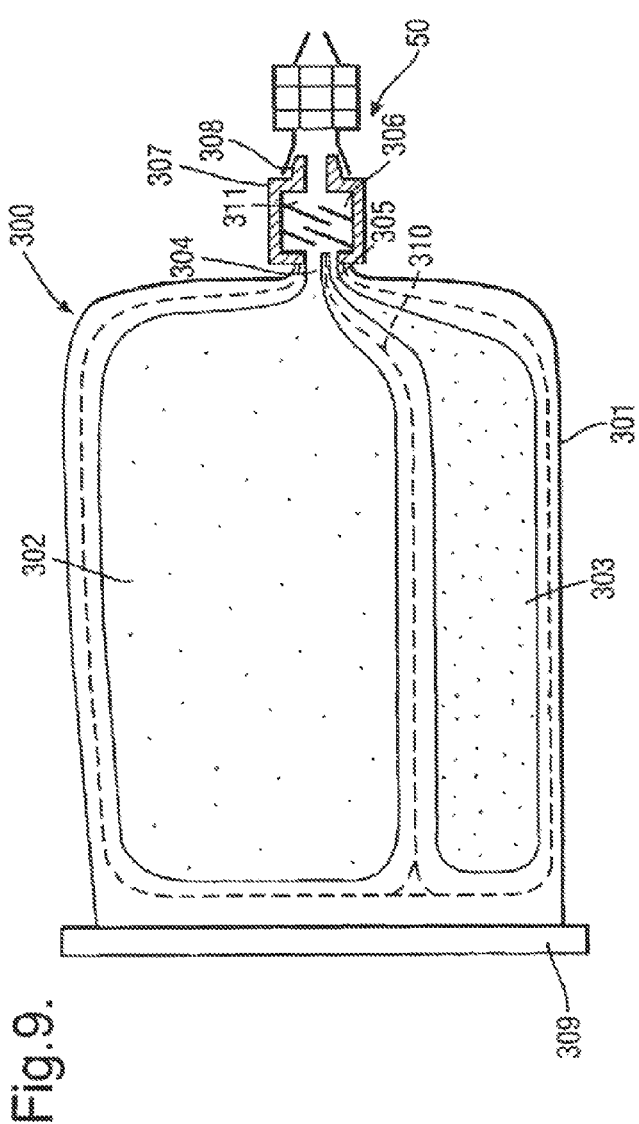
FIG. 9 is a schematic representation of a third embodiment of device according to the invention.
Figure 10:
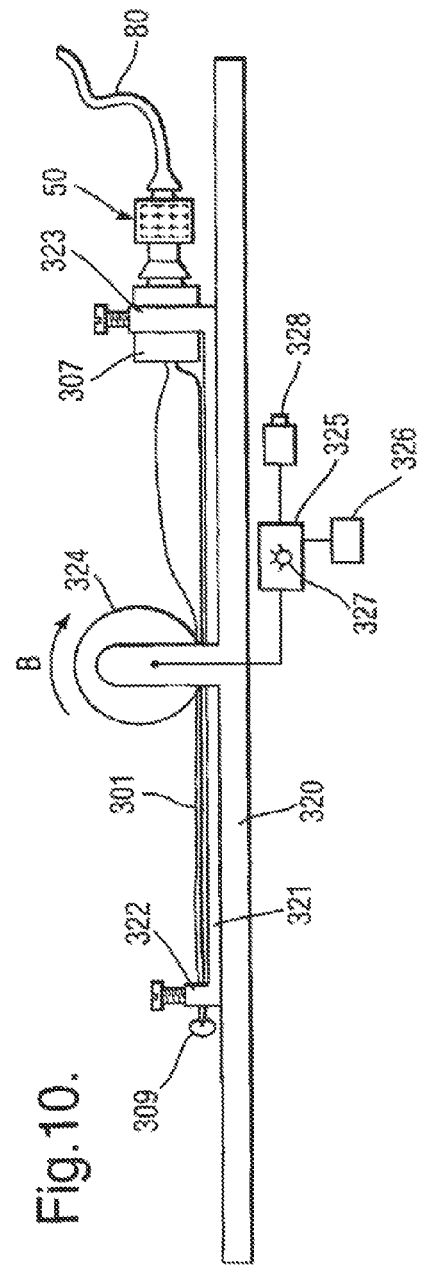
FIG. 10 is a schematic representation of the device of FIG. 9 fitted to a motorized driver.

FIGS. 9 and 10 show an alternative embodiment 300 of foam generating and dispensing device. This embodiment is based on a bag 301 of metal/plastics laminate material. In the bag are located chambers 302, 303 separated by ultrasonically welded seams 310. The chambers 302, 303 contain carbon dioxide and 1% polidocanol solution respectively. The chambers are disposed in parallel along substantially the whole length of the bag, and the cross sections of the chambers, when filled, is selected so as to ensure a correct gas/air mix as with the syringe embodiments. Each chamber 302, 303 has a channel 304, 305 leading to a mixing region or mixing chamber 306 defined within a housing 307. On the front of the housing 307 is a luer nozzle 308, to which is fitted a foaming unit 50 as with previous embodiments. Within the mixing chamber 306 are located mixing fins 311.

At the rear of the bag 301 is a relatively stiff rod 309. In use, the bag 301 is rolled around the rod 309 to expel gas and liquid from the chambers 302, 303 respectively. As with previous embodiments, the gas and liquid enter the mixing chamber where they are well mixed before entering the foaming unit 50 and being converted to foam of preset density.

As with the other embodiments, the bag is preferably used with a driver device such as is shown schematically in FIG. 10. In FIG. 10 the bag 301 can be seen in side view, held in place on a movable carriage 321, slidably mounted on a base plate 320. The rear of the bag 301 is clamped by a bag clamp 322 at the rear of the carriage 321; the rod 309 in this situation serves to help prevent the bag slipping through the clamp. The mixing chamber housing 307 at the front of the bag is clamped in a mixing chamber clamp 323 at the front of the carriage 321.

To set up the driver, the carriage, complete with bag, is slid sideways under a roller 324 mounted on the base plate 320. In order to do this, the bag is manually depressed at the rear end, adjacent the rod 309 to allow it to fit under the roller 324.

The roller 324 is driven by an electric motor 325 supplied from a DC power supply 326. The speed of the motor may be calibrated using speed control 327 and stopped and started using on/off switch 328.

On starting the motor, the roller rotates in the sense indicated by arrow B, causing the carriage, complete with bag, to slide under the roller. Gas and liquid contained in the bag is thereby forced through the mixing chamber 306 and foaming unit 50, and out of an exit of the foaming unit.

As with the previous embodiments, the clinician would ensure that consistent foam is being produced before connecting up a line 80 to a cannula installed in a patient's vein.

Figure 11:
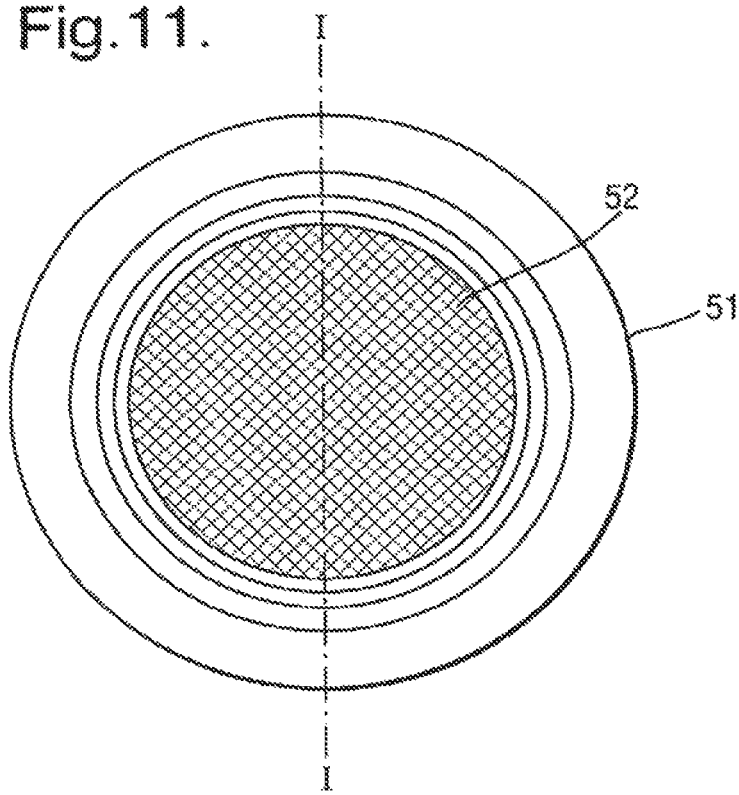
FIG. 11 is a plan view of a mesh element of an embodiment of a foaming unit forming part of the invention.
Figure 12:
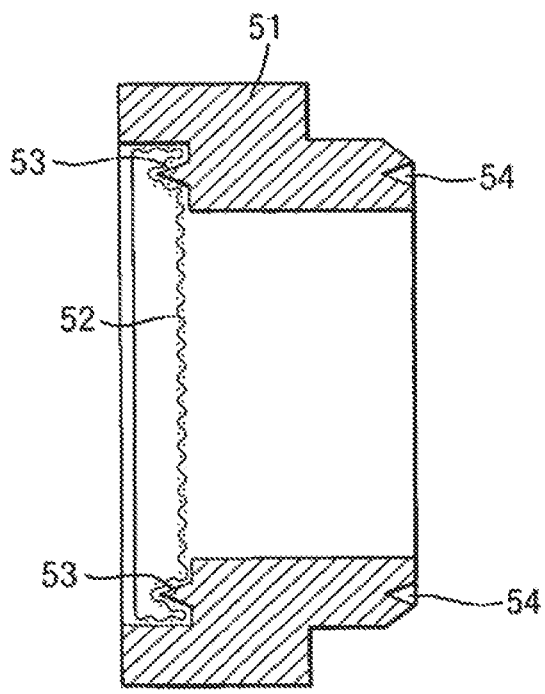
FIG. 12 is a side sectional view along the line I-I in FIG. 11.
Figure 13:
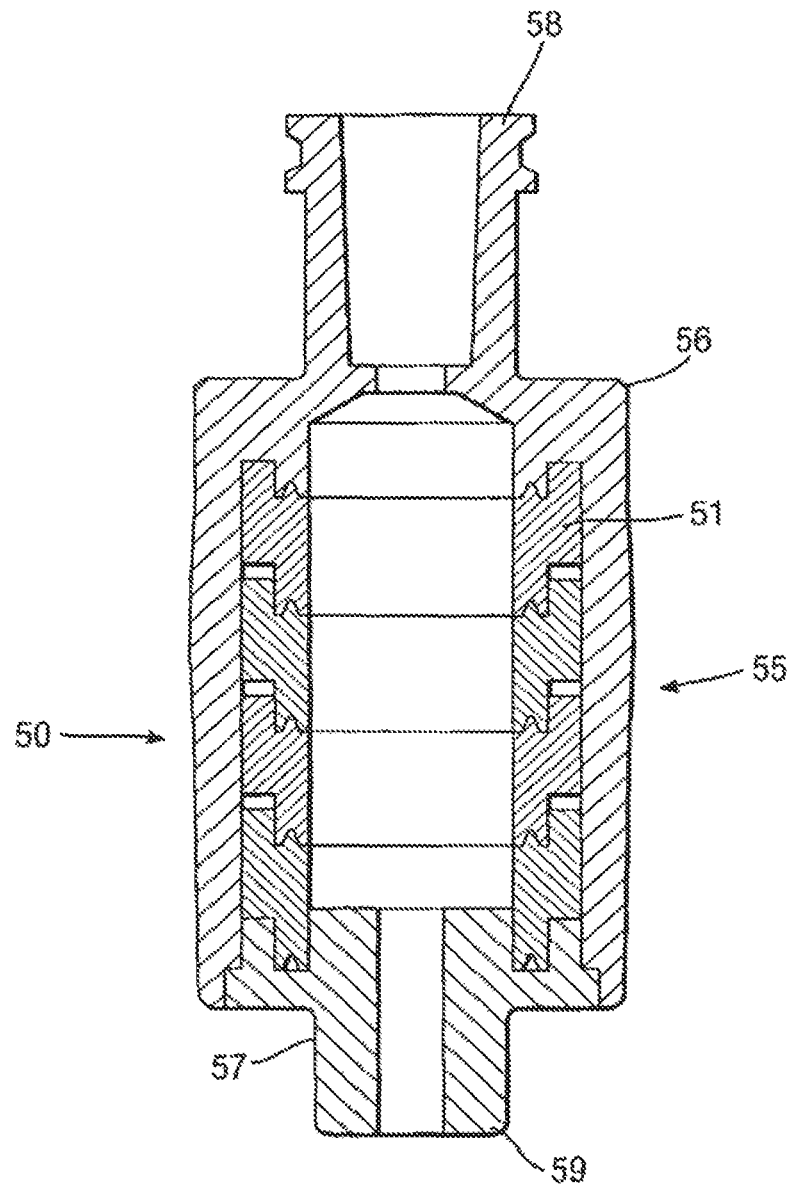
FIG. 13 is a side sectional view of an embodiment of foaming unit forming part of the invention.

Referring now to FIGS. 11 to 13, the foaming unit comprises four mesh elements, each comprising a ring 51 having a mesh 52 secured across it. The mesh has perforations of diameter approximately 5 micron. Each mesh element has male and female sealing surfaces 53, 54 respectively—these are best seen in FIG. 12.

FIG. 13 shows four mesh elements stacked together such that the male sealing surface of one element engages the female surface of the element next to it. The elements are retained in housing 55 having a socket half 56 and a nozzle half 57. Between these halves of the housing, the mesh elements are retained under pressure, with the sealing surfaces 53, 54 engaging with each other and with the interior of the housing 55 at each end. In this way a good seal is created between the mesh elements, so that all flow through the foaming unit must pass through the mesh.

The socket end 56 of the housing is formed with a standard luer socket 58 which, in use, fits over the luer nozzle output of the various devices described above. The nozzle end 57 of the housing incorporates a standard luer nozzle 59 onto which a medical line having a standard luer socket may be fitted.

Alternatives to the mesh elements described are contemplated: anything which provides pores, perforations, interstices, etc with a dimension in a direction approximately transverse to the direction of flow of between 0.1 micron and 100 micron may be suitable. Examples might include a fabric, perforated screen or sinter.

The following examples are provided in support of the inventive concepts described herein.

The present invention will now be described further by way of illustration only by reference to the following Figures and Examples. Further embodiments falling within the scope of the invention will occur to those skilled in the art in the light of these.

Example 1

10 patients were treated for varicose veins by injection of foam made with 1% polidocanol solution and a gas mix consisting essentially of 7-8% nitrogen and the remainder carbon dioxide (about 22%) and oxygen (about 70%).

The procedure involved the injection of up to 30 ml of foam (25.5 ml gas) into the thigh section of the greater saphenous vein. 4-chamber cardiac ultrasound examinations were conducted on all the patients to test for bubbles reaching the heart. Bubbles were observed in the right atria and ventricles of all 10 patients examined. In general, bubbles appeared several minutes following injection of the foam and continued until the ultrasound recording was stopped about 40 minutes after injection.

In one patient, microbubbles were observed in the left atrium and ventricle. This patient was subsequently confirmed to have a patent foramen ovate.

Example 2

The objective of this experiment was to investigate the nature of the residual bubbles that pass into the heart following injection into the saphenous vein of polidocanol foam made with different gas mixtures.

An anaesthetised female hound dog weighing 26 kg was injected with foam containing polidocanol formulated with varying gas mixes. Residual bubbles were monitored in the pulmonary artery using transoesophageal echocardiogram (TEE). Residual bubbles visualised on TEE were sampled from the pulmonary artery through a wide-bore catheter. These blood samples were analysed for the presence of residual bubbles using light microscopy and ultrasound.

Three different compositions of foam were used, as follows:

1% polidocanol and air

1% polidocanol and a gas mix consisting of 7-8% nitrogen and the remainder carbon dioxide and oxygen 1% polidocanol solution and a gas mix comprising less than 1% nitrogen and the remainder carbon dioxide and oxygen.

The TEE output was videotaped and subsequently analysed. For all three compositions, bubbles reached the pulmonary artery in sufficient quantity to cause a substantially opaque image. It is believed that the threshold bubble density required to produce such an image as quite low, and therefore this image in itself did not provide useful data. The time taken for the occluded image to revert to a steady state background image was believed to be approximately indicative of the length of time taken for all or most the bubbles to have dissolved into the bloodstream. The TEE was very sensitive (showing activity even when saline was injected as a control); for this reason exact end points were difficult to determine. However, the following estimates have been made of the time period from opacification of the image to decay down to a background level, 4 minutes 2 minutes 20 seconds.

In addition to the TEE analysis, observations were made of samples of blood drawn from the pulmonary artery for each foam during the period when the TEE image was substantially opaque. The results of these observations were as follows.

As soon as the sample was taken, a considerable volume of bubbles was observed in the syringe. When the syringe was held with its longitudinal axis horizontal, a continuous strip of bubbles was observed extending substantially the full length of the 20 ml syringe.

Initially on taking the sample no bubbles were observed in the syringe, but after a few seconds, with the syringe in the horizontal position, a line of bubbles appeared which was thinner than the line observed for foam A.

After taking the sample and holding the syringe in the horizontal position, no bubbles were observed for a period of a minute or more. Gradually, a thin line of bubbles began to appear along the top of the syringe.

It was not possible to measure the bubbles, but they appeared to be smaller for composition C than for composition B, with the bubbles from composition B in turn smaller than those from composition A.

Example 3

In vitro experiments were conducted to determine the absorption of foam made with different gases in fresh human venous blood.

A 20 ml polypropylene syringe barrel was prepared by puncturing its side wall with a relatively large hypodermic needle to make a hole approximately 1 mm in diameter. This hole was then covered by securing a piece of clear flexible vinyl sheet over it with clear adhesive tape. A small magnetic stirrer element was introduced into the syringe barrel and the plunger then replaced. 20 ml of human venous blood was then with drawn in the usual manner from a human subject using the specially prepared syringe fitted with a hypodermic needle.

The hypodermic needle was removed and the syringe then placed on a magnetic stirrer unit so that the magnetic element in the syringe thoroughly agitated the blood. The Luer nozzle of the syringe was then connected to a 50 cm piece of manometer tubing which was arranged horizontally and left open at one end. The manometer tubing was secured against a scale.

A 0.5 ml measuring syringe with a fine pre-fitted needle was then filled with foam made from 1% polidocanol solution and air. The density of the foam was 0.13 g/ml (±0.03 g/ml), the liquid component making up approximately 13% of the total volume of foam (±3%).

The needle of the 0.5 ml syringe was then introduced through the vinyl sheet on the side wall of the 20 ml syringe. A small volume of blood was found to have entered the manometer tubing and the position of the distal end of this column of blood was noted against the scale. The 0.5 ml aliquot of foam was then injected quickly and simultaneously a timer started (t0). As the foam displaced blood in the 20 ml syringe, the column of blood from the 20 ml syringe was displaced into the manometer tubing and the distance along the tubing reached by the distal end of the blood column was noted against the scale. The scale itself comprised spaced marker lines equally spaced at about 1 cm intervals. It was determined that a distance of 45 intervals on this scale corresponded to an internal volume of in the manometer tubing of approximately 0.5 ml.

As the gas in the foam started to be absorbed by the blood, the blood in the manometer tubing started to recede back towards the syringe. After the column appeared to have stopped moving, the timer was stopped (tF). The position of the distal end was again noted.

This experiment was then repeated for a foam of the same density but made with oxygen gas ("medical grade" purity—99.5% minimum).

The experiment was repeated again but this time oxygen gas from a cylinder of medical grade oxygen was introduced directly into the 0.5 ml syringe instead of foam.

The results of these three tests are presented below in Table 1

TABLE 1

| Test | Foam/gas | Start position of blood ("x") | Position of blood at $t_0$ ("y") | $t_F$ (seconds) | Position of blood at $t_F$ ("z") | Absorbed volume at $t_F$ (ml) $0.5(y-z)$ $(y-x)$ | Liquid Volume in foam (ml) | Unabsorbed gas ml | % |
|---|---|---|---|---|---|---|---|---|---|
| 1 | Air foam | 2 | 47 | 80* | 40 | 0.08 | 0.13 × 0.5 = 0.07 | 0.35 | 81% |
| 2 | Oxygen foam | 4 | 48 | 140 | 11 | 0.42 | 0.13 × 0.5 = 0.07 | 0.01 | 2% |
| 3 | Oxygen gas | 2 | 47 | 140 | 5.5 | 0.46 | nil | 0.04 | 8% |

*No further movement of the blood column was observed after 80 seconds.

The experimental error in this example is unfortunately too great to conclude whether there is or is not a residual volume of gas for the oxygen gas or oxygen foam, although clearly the great majority at least of the gas is absorbed. There will have been a small percentage of nitrogen in the gas, from the oxygen cylinder which is only 99.5% pure, and possibly also introduced during the experiment. Diffusion of nitrogen into the bubbles from the blood is also a possibility, as discussed above, and some nitrogen may have been introduced inadvertently during the procedure.

In this experiment, the air foam test was only observed for a few minutes after tF. However, further experiments have been conducted by the inventors, the results of which are not formally recorded here, involving foam with a percentage of nitrogen. A 20 ml syringe of fresh human venous blood, as in the above experiments, was injected with a 0.5 ml aliquot of a foam containing a percentage of nitrogen. The contents of the syringe were agitated as above and a period of 24 hours allowed to elapse. An easily visible volume of bubbles remained in the syringe.

Example 4

Preparation of Ultra-Low Nitrogen Canister

An anodised aluminium canister with an open top was filled with water. The canister was then immersed in a bath of water and inverted. A line from a pressurised cylinder of oxygen gas was then introduced into the water bath and the supply of oxygen turned on, thereby flushing the line of any air. A canister head assembly comprising a valve, dip tube and mesh stack unit was then immersed in the water bath and connected to the oxygen line for a few seconds to purge air from the assembly.

The oxygen line was then introduced into the inverted canister until all water had been displaced from the canister. The line was then removed from the canister and the previously purged head assembly quickly clamped over the top of the canister thereby sealing the canister. The canister was then removed from the water bath with the head assembly still clamped against it; the head assembly was then secured to the canister using a standard crimping technique.

The canister was then pressurised to about 8 bar absolute pressure by connecting the canister valve to a regulated oxygen line for 1 minute. The pressure as then relieved by opening the valve until the pressure in the canister was just above 1 bar absolute; a pressure gauge was applied to the valve intermittently during the pressure release operation to ensure that the canister pressure did not drop all the way down to 1 bar absolute. This was done to avoid the possibility of atmospheric air seeping into the canister.

The canister was then pressurised again up to about 8 bar absolute and the pressure release operation repeated. This process was then repeated a third time, with the final canister pressure being from 1.1 to 1.2 bar absolute.

18 ml 1% polidocanol solution was then introduced through the canister valve using a syringe with all air pockets, including any air in the luer nozzle, removed. The canister valve was then connected to a carbon dioxide cylinder and pressurised to 2.2 bar absolute. Then the oxygen line was again connected to the valve and the pressure increased to 3.6 bar absolute.

Table 2 below shows the expected result from the oxygen pressurising and depressurising cycles, assuming 100% pure oxygen in the cylinder and assuming that despite the precautions taken 1% of the gas in the canister after the initial oxygen filling procedure is nitrogen. The worst case is assumed for the canister pressure values, namely 1.2 bar absolute ("bara") and 7.6 bara.

TABLE 2

| | N2 partial pressure (bara) | Canister pressure (bara) | % N2 |
|---|---|---|---|
| Start | 0.012 | 1.2 | 1% |
| $1^{st}$ cycle | 0.012 | 7.6 | 0.16% |
| | 0.00189 | 1.2 | 0.16% |
| $2^{nd}$ cycle | 0.00189 | 7.6 | 0.02% |
| | 0.000299 | 1.2 | 0.02% |
| $3^{rd}$ cycle | 0.000299 | 7.6 | 0.00% |
| | 0.0000472 | 1.2 | 0.00% |

As can be seen the percentage of nitrogen drops down to zero, calculated to two decimal places, after the three oxygen pressure/release cycles.

The oxygen cylinder used in the above process was a standard medical grade oxygen cylinder supplied by B.O.C. and specified at 99.5% or greater purity. The carbon dioxide cylinder used was so called "CP Grade" from B.O.C. which has a purity level of 99.995%.

Working to two decimal places, the impurity (which will be mainly nitrogen) arising from the initial filling procedure should be reduced to zero after three pressure/release cycles. Similarly the impurity level in the canister from the carbon dioxide cylinder can be considered zero to two decimal places, since the purity of the source was 99.995% and only approximately one third of the gas in the finished canister was carbon dioxide.

The inventors will perform further experiments along the above lines using oxygen and carbon dioxide sources of higher purity. The following cylinder oxygen is readily available from B.O.C.:

"Medical grade" 99.5% purity (as used in the above procedure)
"Zero grade" 99.6% purity
"N5.0 grade" 99.999% purity
"N5.5 grade" 99.9995% purity
"N6.0 grade" 99.9999% purity
In each case the impurity IS mainly nitrogen.

The following cylinder carbon dioxide products are readily available from B.O.C. They have the following specifications:

"CP grade N4.5" 99.995% purity (as used in the above procedure)
"Research grade N5.0" 99.999% purity.

It will be appreciated that repeating the procedure described above using "Zero grade" oxygen would result in a finished canister having maximum impurity (which will be mainly nitrogen) of 0.4%.

Of course the number of pressure/release cycles may be increased in order further to reduce the theoretical maximum impurity if the oxygen and carbon dioxide sources were 100% pure. It is a simple calculation to show the number of cycles necessary to reduce the maximum percentage impurity level to zero, calculated to 3, 4 or 5 decimal places. Provided the canister pressure never drops to or below 1 bar absolute and provided the lines from the oxygen and carbon dioxide cylinders are flushed through with gas prior to attachment to the canister valve, there is no reason to assume that any significant impurity will enter the canister during the pressure/release cycles.

A refinement of the procedure to reduce further any opportunity for impurity to enter would be to introduce the polidocanol solution immediately after initial flushing, in this way, any air/nitrogen introduced with the polidocanol will be eliminated during the subsequent pressure/release cycles.

A further refinement of the technique might be to maintain the water bath in an agitated state using a magnetic stirrer, under a continuously refreshed oxygen atmosphere for 24 hours. In this way, any dissolved nitrogen in the water bath should be eliminated and replaced with dissolved oxygen. Filling the canister from this oxygenated water bath should, it is postulated, remove the water bath as a possible source of nitrogen impurity.

It is envisaged that five, ten, twenty or even 100 pressure/release cycles could be performed.

In this manner, using appropriate sources of oxygen and carbon dioxide as detailed above, it will be possible to make a canister charged with polidocanol and an oxygen and carbon dioxide mix having a percentage impurity of 0.005% or less (mainly nitrogen) using CP grade carbon dioxide or 0.001% or less using research grade carbon dioxide. It should also be possible to make a polidocanol and oxygen canister with a percentage impurity of nitrogen gas of 0.0001% or less using N6.0 grade oxygen.

It will of course be appreciated that the production of canisters in this way having a somewhat higher minimum nitrogen level is not difficult and may be achieved, for example, by reducing the number of pressure/release cycles.

It will also of course be appreciated that substitution of polidocanol by an alternative liquid component would be a trivial matter.

Example 5

Preparation of Ultra-Low Nitrogen Canister

The inventors are at present developing a procedure for large scale manufacture of ultra-low nitrogen canisters, using a similar methodology. In this procedure, two canisters are manufactured, one containing oxygen at 5.8 bar absolute and the other carbon dioxide and polidocanol solution at about 1.2 bar absolute. In use, the CO2/polidocanol canister is pressurised immediately prior to use by connecting it to the oxygen canister. This is described in WO 02/41872-A1[CDE10].

There is therefore a separate manufacturing procedure for the oxygen and carbon dioxide/polidocanol canisters. However, it will be apparent that either procedure is applicable to production of a single canister product containing polidocanol and oxygen, carbon dioxide or a mix of the two.

The procedure will be described first for an oxygen canister, which is simply an anodised aluminium canister with a standard valve assembly in the top. Prior to fitting the valve assembly, the canister is first flushed with oxygen gas by inserting an oxygen line into the open top of an upright cylinder for 10 seconds. The line is then withdrawn. At this stage not all the air will have been eliminated and it is believed that the nitrogen impurity level is around 5% or 6%; this has not been measured specifically, but has been deduced from the measured impurity level at a later stage in the procedure (see below). It is not believed that flushing the canister for a longer period would substantially change this value for nitrogen gas impurity.

The valve assembly is then loosely fitted and a filling head brought into engagement around the top of the canister and valve assembly so as to make a gas-tight seal against the canister wall. Connected to the filling head is a line for oxygen. The canister is then brought up to a pressure of approximately 5.5 bar absolute (bara). Nitrogen gas impurity at this stage has been measured by standard gas chromatography techniques to be about 1%.

At one stage it was thought to be acceptable to have the nitrogen impurity level at around 1%, but following the results of the clinical trial (Example 1), it has been determined that a lower nitrogen content is desirable. For this reason, further steps have been added to the procedure, as follows.

Maintaining the seal between the canister and filling head, the contents of the canister are exhausted via the filling head until the pressure in the canister is just over 1 bara. As with Example 4 above, this is to prevent any potential ingress of atmospheric air through the seal.

Maintaining the seal between the canister and filling head, the pressure is then increased again to about 5.5 bara and again this pressure is released down to just over 1 bara. The canister is then brought up to its final pressure of 5.5 bara±0.4 bara. At this stage, the nitrogen gas impurity measured by gas chromatography is about 0.2%.

It will be appreciated that each of the pressure/release cycles should reduce the impurity due to residual air/nitrogen by a factor of about 5 assuming no leakage. It is reasonable to assume no leakage since a positive pressure is always maintained in the canister. Assuming a 100% pure source of oxygen, the theoretical nitrogen impurity after these three pressure/release cycles should be around 0.05%. Since the measured nitrogen level is around 0.2%, there is apparently either impurity in the line or nitrogen is entering the sample during the measuring process. It can at least be concluded that the impurity level is 0.2% or better.

It will be appreciated that polidocanol solution, or any other liquid sclerosing agent, could be added into the canister during the above procedure and the standard valve and dip tube could be replaced with a unit including foam generating means such as a small aperture mesh. In the final step, the pressure in the canister may be brought up to whatever is required, e.g. around 3.5 bara. In this way, a final pressurised canister product containing sclerosant and substantially pure oxygen could be made.

At present, the effects, including possible oxidising effect, of storing polidocanol solution under pressurised oxygen are not fully understood. Therefore, it is preferred at present to have a two canister system in which the polidocanol solution is stored under carbon dioxide and/or nitrogen.

In previous versions of the product (as used in Example 1), the gas mix in the polidocanol canister was 25% nitrogen and 75% carbon dioxide. The nitrogen was present in order to reduce the deleterious effect of the highly soluble carbon dioxide on the stability of the foam. In order to minimise both the carbon dioxide and the nitrogen content of the foam, this canister was maintained at 0.5 bara. This meant that, when the canister was connected to the oxygen canister and the final pressure raised to about 35 bara, the nitrogen content reduced to around 7%.

It was then realised by the inventors that (1) the canister needed to be maintained at above atmospheric pressure to avoid the risk of contamination and (2) the percentage of nitrogen was too high. A new design of can was produced in which the foam generating mesh has smaller apertures—5 micron instead of 20 micron. Although it was previously thought that differences in size at this level would not have a significant effect on the foam, it was in fact surprisingly found that this reduction in mesh pore size was just sufficient to compensate for the increased percentage of carbon dioxide which resulted from having substantially pure carbon dioxide in the canister and also from maintaining it at just over 1 bara instead of 0.5 bara.

Using a polidocanol canister of this design, and an oxygen canister as described above which is pressurised only once, the resulting foam had a nitrogen impurity of around 1-2%.

The current procedure is to insert a carbon dioxide line into the open top of a metal anodised canister for 10 seconds. The line is then withdrawn. At this stage not all the air will have been eliminated and it is believed that the nitrogen impurity level is around 5% or 6%. It is not believed that flushing the canister for a longer period would substantially change this value for nitrogen gas impurity.

18 ml of 1% polidocanol solution is then introduced into the canister, a carbon dioxide line reintroduced and the canister flushed again for a few seconds.

The head assembly, including dip tube, valve and foam generating mesh unit, is then loosely fitted and a filling head brought into engagement around the top of the canister and valve assembly so as to make a gas-tight seal against the canister wall. Connected to the filling head is a line for carbon dioxide. The canister is then brought up to its pressure of approximately 1.2 bar. Nitrogen gas impurity at this stage has not yet been measured but is expected to be in the region of 0.8%.

The final nitrogen impurity of a foam generated from the charged polidocanol canister after it has been connected to the oxygen canister to bring it up to about 3.5 bars, is given by:

$$(0.8 \times 1.2 + 0.2 \times 2.3)/3.5 = 0.4\%$$

Example 6

A unit was prepared comprising a housing with ports at each end formed as standard luer connections. Within the housing was an internal pathway between the ports in which pathway four mesh elements were installed such that flow between the ports was required to flow through the meshes. The meshes had 5 micron apertures.

8 ml of 1% polidocanol solution was drawn up into a standard 20 ml syringe and this syringe then fitted to one port of the mesh stack unit described above. A second 20 ml syringe was then taken and 12 ml of air drawn up into it before fitting it to the other of the two ports on the mesh stack unit. The internal volume of the mesh stack unit was measured and determined to be essentially negligible for these purposes, being 0.5 ml or less.

The air and polidocanol solution was then shuttled back and forth between the syringes as fast as possible by hand for one minute. The number of passes achieved was 15.

The resulting product was a white liquid of homogeneous appearance with no visible bubbles. A sample of this liquid was analysed for bubble size (see Example 9 below) and the results tabulated below (Table 2).

TABLE 2

| Bubble diameter ($\mu$) | Number of bubbles | Cumulative freq. (%) | Frequency (%) |
|---|---|---|---|
| 0-15 | 1420 | 28.4 | 28.4 |
| 15-30 | 1293 | 54.3 | 25.9 |
| 30-45 | 1230 | 78.9 | 24.6 |
| 45-60 | 819 | 95.3 | 16.4 |
| 60-75 | 219 | 99.7 | 4.4 |
| 75-90 | 15 | 100.0 | 0.3 |
| 90-105 | 0 | 100.0 | 0.0 |
| 105-120 | 0 | 100.0 | 0.0 |
| 120-135 | 0 | 100.0 | 0.0 |
| Totals: | 4996 | | 100.0 |

Example 7

A similar experiment to Example 6 above was performed with a housing containing 4 mesh units each comprising a 5 micron mesh. This time, 10 ml of 1% polidocanol solution was drawn up in one 20 ml syringe and 10 ml of air drawn up in the other. The air and polidocanol were shuttled back and forth as fast as possible by hand for 2 minutes; 27 passes were achieved.

The resulting product was a white liquid of homogeneous appearance with no visible bubbles. A sample of this liquid was analysed for bubble size (see Example 9 below) and the results shown in Table 3 below.

TABLE 3

| Bubble diameter ($\mu$) | Number of bubbles | Cumulative freq. (%) | Frequency (%) |
|---|---|---|---|
| 0-15 | 2387 | 47.8 | 47.8 |
| 15-30 | 1293 | 73.7 | 25.9 |
| 30-45 | 969 | 93.1 | 19.4 |
| 45-60 | 309 | 99.2 | 6.2 |
| 60-75 | 32 | 99.9 | 0.6 |
| 75-90 | 5 | 100.0 | 0.1 |
| 90-105 | 2 | 100.0 | 0.0 |
| 105-120 | 0 | 100.0 | 0.0 |
| 120-135 | 0 | 100.0 | 0.0 |
| Totals: | 4996 | | 100.0 |

Example 8

A similar experiment to Examples 6 and 7 above was performed with a housing containing 4 mesh units each comprising an 11 micron mesh. 8 ml of 1% polidocanol solution was drawn up in one 20 ml syringe and 12 ml of air drawn up in the other. The air and polidocanol were shuttled back and forth as fast as possible by hand for 1 minute; 25 passes were achieved.

The resulting product was a white liquid of homogeneous appearance with no visible bubbles. A sample of this liquid was analysed for bubble size (see example 9 below) and the results shown in Table 4 below.

TABLE 4

| Bubble diameter (µ) | Number of bubbles | Cumulative freq. (%) | Frequency (%) |
|---|---|---|---|
| 0-15 | 620 | 12.4 | 12.4 |
| 15-30 | 753 | 27.5 | 15.1 |
| 30-45 | 1138 | 50.3 | 22.8 |
| 45-60 | 1279 | 75.9 | 25.6 |
| 60-75 | 774 | 91.4 | 15.5 |
| 75-90 | 331 | 98.0 | 6.6 |
| 90-105 | 85 | 99.7 | 1.7 |
| 105-120 | 15 | 100.0 | 0.3 |
| 120-135 | 1 | 100.0 | 0.0 |
| Totals: | 4996 | | 100.0 |

Example 9

Bubble Sizing Technique

The bubble sizing technique used to measure the bubble size distribution of the foams from Examples 6 to 8 above comprises computer analysis of the image of the bubbles though a microscope. A small sample of the foam is deposited on a specially prepared slide which has spacers 37 microns high mounted on each side. A further slide is then carefully positioned on top of the sample and spacers, thereby spreading the sample into a layer of 37 micron thickness. A digital image of part of the 37 micron layer of bubbles is then recorded and processed; the bubbles appear as rings in the image, the ring representing the outermost diameter of the bubble. Each bubble is individually identified and numbered, and its diameter calculated. For bubbles over 37 microns in diameter it is assumed that the bubble has been flattened to some degree causing the diameter of the ring in the image to be larger than the diameter of the undeformed bubble. An algorithm for calculating the original diameter of the undeformed bubble is applied. For bubbles 37 microns and under, it is assumed that the bubble has floated up against the underside of the upper slide and is undeformed. From visual inspection of the digital image, this does not appear to be an unreasonable assumption since overlapping bubble images are either absent completely or are very rare. Nevertheless it is intended to repeat the experiments using a set of slides with a 10 micron gap and suitably amended software, once these things have been developed, so that substantially all the bubbles will be flattened between the slides.

Example 10

Examples 6, 7 and 8 above are repeated using the following method.

Polidocanol solution is drawn up into a 20 ml syringe as described in Examples 6, 7 and 8, ensuring that excess solution is drawn up and then solution dispensed with the nozzle pointed upwards, until the appropriate volume of polidocanol solution is left. In this way any air voids in the syringe, particularly in the nozzle, are removed.

The polidocanol-filled syringe is then connected to the mesh unit, the assembly oriented with syringe pointing upwards, and the mesh unit filled with solution, eliminating all air bubbles.

A line from a cylinder of medical grade oxygen (99.5% purity) is connected to the luer connector of a 20 ml syringe with the plunger removed. The oxygen line and syringe barrel and luer connector are then flushed for 10 seconds with oxygen from the cylinder. The oxygen line is then removed, keeping the supply of oxygen turned on, and the syringe plunger inserted into the barrel and the plunger depressed. The oxygen line is then re-attached to the syringe luer and the pressure of the oxygen allowed to push the syringe plunger back to fill the syringe with oxygen.

The oxygen syringe is then immediately connected to the mesh unit and the foam generating procedure described in Examples 6, 7 or 8 carried out.

Example 11

A syringe and mesh unit filled with polidocanol solution as described in Example 10 above are placed in a collapsible "glove box" (a sealable container with integral gloves incorporated into the container wall to allow manipulation by a user of the contents of the container). A further, empty syringe is also placed in the glove box. The box is then sealingly connected to vacuum source and thereby collapsed such that substantially all air is removed. The vacuum source is then replaced by a source of 99.995% pure oxygen and the glove box filled with oxygen from this source; the oxygen supply is maintained and a small vent is opened in the wall of the glove box opposite the point of entry of oxygen. The procedure described in Example 10 above for filling the empty syringe with oxygen is then followed, using the 99.995% pure oxygen supply line within the glove box. The procedure described in Examples 6, 7 and 8 is then carried out to generate foam.

Example 12

A polidocanol syringe and mesh unit are prepared as in Example 10 above. A syringe is immersed in a tank of water and the plunger removed. Once the syringe barrel is completely full of water with no air pockets, a stopper is secured over the luer nozzle. The syringe barrel is held with the nozzle pointing upwards and a line from a 99.9999% pure oxygen cylinder is first purged, then introduced into the syringe barrel. When all water is replaced by oxygen (taking care that the water in the nozzle is displaced), the plunger is inserted and the syringe removed from the water tank. The procedure of Example 10 is then followed to connect the syringe to the mesh unit and make foam.

As with Example 4 above, this procedure could be refined by storing the water tank under a continually refreshed atmosphere of 99.9999% pure oxygen for 24 hours prior to filling the syringe.

Example 13

In a modification of Examples 10-12, the mesh unit can be replaced with a simple connector or three way valve and in all other respects the technique can remain the same, with the possible exception of requiring more passes to make acceptable foam. The aperture in a standard connector or three way valve, through which the gas and liquid are passed, would be about 0.5 mm to 3 mm in its largest dimension. By repeatedly passing the liquid and gas through this aperture it is still possible to obtain a useful foam, though with bubble sizes considerably larger than those obtained by the methods of Examples 6 to 12. This technique is commonly known as the "Tessari" technique. The inventors have experimented with the Tessari technique and found that the size and distribution of bubbles varies widely according to the ratio of gas to air and also the speed and number of passes of the gas and liquid through the aperture. The average bubble size for a Tessari foam has been reported in the literature to be around 300 micron. The best that the inventors have managed to achieve using the Tessari technique is a foam with an average bubble size of around 70 micron, though to do this the ratio of liquid to gas had to be increased to about 40% liquid, 60% gas.

In this example, the Tessari technique can be adapted to make a foam of whatever density and bubble size is desired, within the limitations described above, but using gas with a very low percentage of nitrogen impurity.

Example 14

A canister was prepared of the type described in WO00/72821-A1 having a dip tube and a standard valve assembly provided with a pair of small air inlet apertures, together with a mesh stack unit having a 5 micron aperture size. The size of the apertures in the valve was enlarged slightly compared with the valve arrangement described in WO0/72821-A1 (which is designed to produce a foam of density between 1.1 g/ml and 1.6 g/m). The purpose of this modification was to increase the proportion of liquid to gas in the mixture passing through the mash stack.

The canister was filled with 18 ml of 1% polidocanol solution and pressurised with a mixture of oxygen, carbon dioxide and nitrogen. A foam was then dispensed.

This procedure was repeated for different sizes of valve aperture and a number of foams produced, all having the appearance of a white liquid and densities in the range 0.3 to 0.5 g/ml. Bubble size analysis was performed for each of these foams, which showed the average bubble size in the region of 50 to 80 micron diameter.

Example 15

The above experiment was repeated but with the length and diameter of the dip tube adjusted rather than the size of the apertures in the valve unit. It was necessary to increase the volume of liquid in the canister to ensure that the shortened dip tube reached the liquid level in the canister. It was possible to produce the same type of foam as described in Example 6above.

Example 16

The inventors envisage reproducing the above experiments using a pure oxygen or oxygen and carbon dioxide formulation having nitrogen impurity levels as described above. The same techniques as those described in Examples 4 and 5 may be followed for producing very low levels of nitrogen impurity.

Example 17

Pre-Pressurised Container

Figure 14:
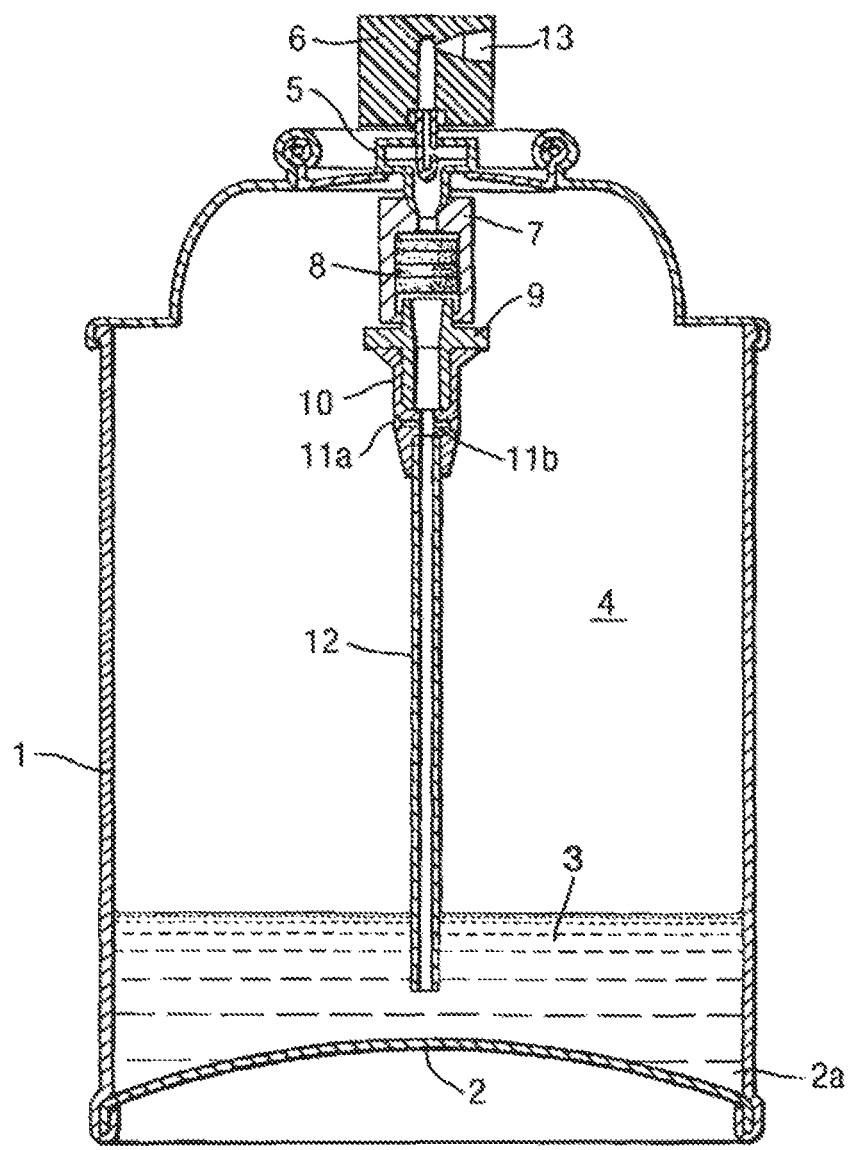
FIG. 14 shows a cross-sectional view of a pre-pressurised container for the generation of therapeutic foam according to the invention, as disclosed in WO 00/72821-A1 and further described below.

A typical apparatus for the generation of therapeutic foam according to the invention, as disclosed in WO 00/72821-A1, is shown in FIG. 14.

The canister has an aluminium wall (1), the inside surface of which is coated with an epoxy resin. The bottom of the canister (2) is domed inward. The canister inner chamber (4) is pre-purged with 100% oxygen for 1minute, containing 15 nm of a 1% vol/vol polidocanol/20 mmol phosphate buffered saline solution/4% ethanol, then filled with the required gas mixture.

A standard 1 inch diameter Ecosol™ aerosol valve (5) (Precision Valve, Peterborough, UK) is crimped into the top of the canister after sterile part filling with the solution and may be activated by depressing an actuator cap (6) to release content via an outlet nozzle (13) sized to engage a Luer fitting of a syringe or multi-way connector (not shown). A further connector (7) locates on the bottom of the standard valve and mounts four Nylon 66 meshes held in high density polyethylene (HDPE) rings (8), all within an open-ended polypropylene casing. These meshes have diameter of 6 mm and have a 14% open area made up of 20 µm pores, with the meshes spaced 3.5 mm apart.

A further connector (9) locates on the bottom of the connector holding the meshes and receives a housing (10) which mounts the dip tube (12) and includes gas receiving holes (11a, 11b) which admit gas from chamber (4) into the flow of liquid which rises up the dip-tube on operation of the actuator (6). These are conveniently defined by an Ecosol™ device provided by Precision Valve, Peterborough, UK, provided with an insert. Holes (11a, 11b) have cross-sectional area such that the sum total ratio of this to the cross-sectional area of the liquid control orifice at the base of the valve housing (at the top of the dip-tube) is controlled to provide the required gas/liquid ratio.

Example 18

Container with Engaging Means and Mesh Stack Shuttle

Figure 15:
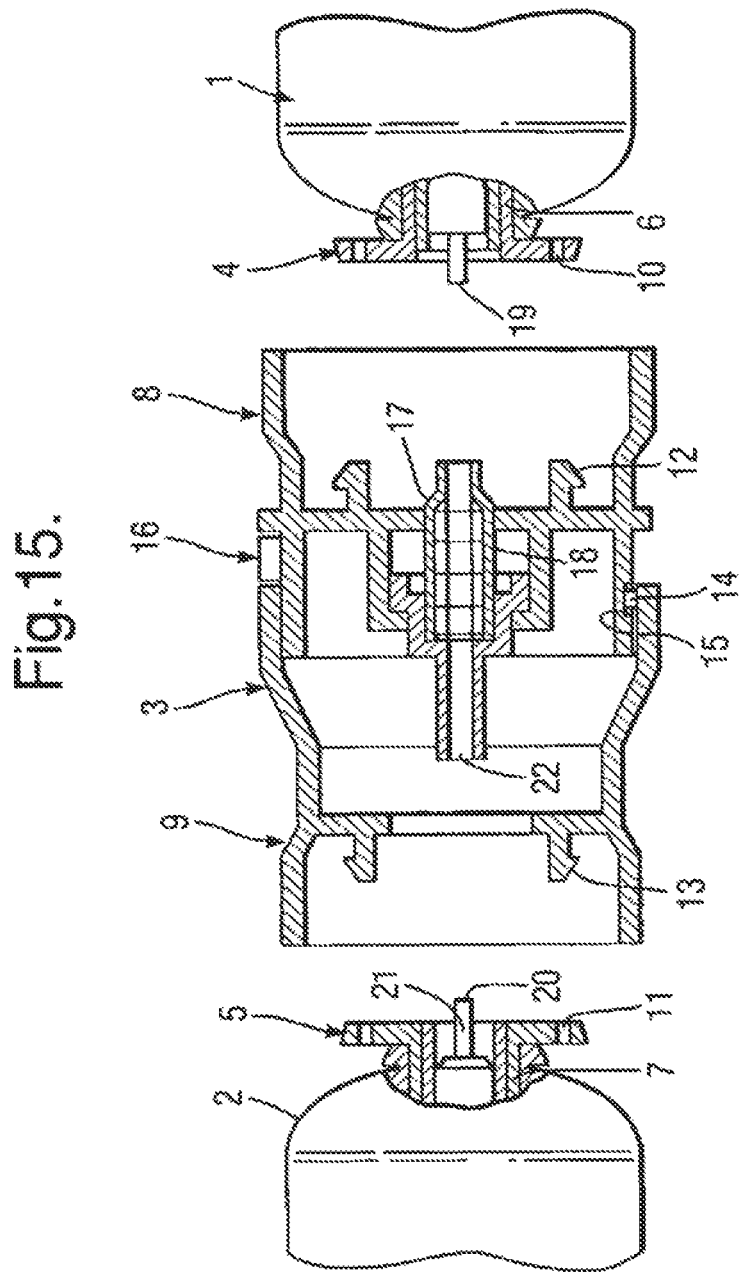
FIG. 15 shows a cross-sectional view of a device comprising a container provided with engaging means and a mesh stack shuttle according to the invention, as disclosed in WO 02/41872-A1 and further described in below.

A device comprising a container provided with engaging means and a mesh stack shuttle according to the invention, as disclosed in WO 02/41872-A1, is shown in FIG. 15. The device comprises a low pressure container (1) for an aqueous sclerosant liquid and an unreactive gas atmosphere, a container (2) for a physiologically acceptable blood-dispersible gas and an engaging means comprising a connector (3).

The container (2) for a physiologically acceptable blood-dispersible gas is charged at 5.8 bar absolute pressure with the required gas mixture, whereas the container (1) is charged with an inert gas. Container (2) is used to pressurise container (1) at the point of use to approx 3.5 bar absolute and is then discarded, just before the foam is required. The two containers will thus be referred to hereinafter as the PD [polidocanol] can (1) and the O2 can (2), and term "bi-can" will be used to refer to the concept of two containers.

Each of the cans (1, 2) is provided with a snap-fit mounting (4, 5). These may be made as identical mouldings. The snap-fit parts (4, 5) engage the crimped-on mounting cup (6, 7) of each can (1, 2) with high frictional force. The connector is made in two halves (8, 9), and the high frictional force allows the user to grip the two connected cans (1, 2) and rotate the connector halves (8, 9) relative to each other without slippage between connector (3) and cans. Each of these can mountings (6, 7) has snap-fit holes (10, 11) for engaging mating prongs (12, 13) which are on the appropriate surfaces of the two halves (8, 9) of the connector.

The connector (3) is an assembly comprising a number of injection mouldings. The two halves (8, 9) of the connector are in the form of cam track sleeves which fit together as two concentric tubes. These tubes are linked by proud pins (14) on one half that engage sunken cam tracks (15) on the other half.

The cam tracks have three detented stop positions. The first of these detents is the stop position for storage. An extra security on this detent is given by placing a removable collar (16) in a gap between the end of one sleeve and the other. Until this collar (16) is removed it is not possible to rotate the sleeves past the first detent position. This ensures against accidental actuation of the connector.

The cam track sleeves (8, 9) are injection moulded from ABS as separate items, and are later assembled so that they engage one another on the first stop of the detented cam track. The assembled sleeves are snap-fitted as a unit onto the O2 can (2) mounting plate (5) via four locating prongs. The security collar is added at this point to make an O2 can subassembly.

The connector (3) includes in its interior a series of foaming elements comprising a mesh stack shuttle (17) on the connector half (8) adjacent to the PD can (1). The mesh stack shuttle (17) is comprised of four injection moulded disk filters with mesh hole size of 20 μm and an open area of approx. 14%, and two end fittings, suitable for leak-free connection to the two canisters. These elements are pre-assembled and used as an insert in a further injection moulding operation that encases them in an overmoulding (18) that provides a gas-tight seal around the meshes, and defines the outer surfaces of the mesh stack shuttle. The end fittings of the stack (17) are designed to give gas-tight face and/or rim seals against the stem valves (19, 20) of the two cans (1, 2) to ensure sterility of gas transfer between the two cans.

The mesh stack shuttle (17) is assembled onto the PD can valve (19) by push-fitting the components together in a aseptic environment.

The PD can (1) and attached shuttle (17) are offered up to the connector (3) and the attached O2 can (2), and a sliding fit made to allow snap-fitting of the four locating prongs (12) on the PD can side of the connector (3) into the mating holes (10) in the mounting plate (4) on the PD can (1). This completes the assembly of the system. In this state, there is around 2 mm of clearance between the stem valve (20) of the O2 can (2) and the point at which it will form a seal against a female Luer outlet from the stack.

When the security collar (16) is removed, it is possible to grasp the two cans (1, 2) and rotate one half of the connector (3) against the other half to engage and open the O2 can valve (20).

As the rotation of the connector (3) continues to its second detent position, the PD can valve (19) opens fully. The gas flow from the O2can (2) is restricted by a small outlet hole (21) in the stem valve (20). It takes about 45 seconds at the second detent position for the gas pressure to (almost) equilibrate between the two cans to a level of 3.45 bar±0.15 bar.

After the 45 second wait at the second detent position, the connector (3) is rotated further to the third detent position by the user. At this position, the two cans (1, 2) can be separated, leaving the PD can (1) with half (8) of the connector and the shuttle assembly (17) captive between the connector and the PD can. The O2 can (2) is discarded at this point.

A standard 1 inch diameter aerosol valve (19) (Precision Valve, Peterborough, UK) is crimped into the top of the PD can (1) before or after sterile filling with the solution and may be activated by depressing the mesh stack shuttle (17), which functions as an aerosol valve actuator mechanism, to release the contents via an outlet nozzle (22) sized to engage a Luer fitting of a syringe or multi-way connector (not shown).

Example 19

Study to Assess the Effect on Physical Properties of Foam From Changes to the Mesh Material in the Mesh Stack This study outlines the effect on foam properties of changing the shuttle mesh pore size from 20 microns to 5 microns, in combination with changes to the gas pressure and gas composition in the canister. The study dates from before the inventors' realisation that a nitrogen concentration of 0.8 or below was desirable. Its main purpose was to test whether use of a 5 micron instead of a 20 micron mesh will compensate for eliminating the 25% nitrogen which was previously deliberately incorporated into the polidocanol canister. The "100%" carbon dioxide and "100%" oxygen referred to in this and the following examples will in fact incorporate levels of nitrogen impurity and the final dual canister product discussed in these examples will probably produce as foam of about 1-2% nitrogen impurity.

Two different gas compositions were used, in one, the canister containing the 1% polidocanol solution and a 75%/25% atmosphere of $CO_2/N_2$ is evacuated to 0.5 bar absolute pressure, whilst the other canister is pressurised to 5.9 bar absolute with oxygen. In the other, the canister containing the 1% polidocanol solution is pressurised to 1.2±0.1 bar absolute with 100% $CO_2$, whilst the other canister is pressurised to 5.8±0.1 bar absolute with oxygen.

The objective of the study is to examine and compare results obtained using 5 micron and 20 micron shuttle meshes, for PD canister pressures of 0.5 bar absolute with the current gas atmosphere and for 1.2 bar absolute PD canister pressures with a 100% 002 as the filling gas.

Materials and Methods:

All sample preparation was performed in a laminar flow booth keeping exposure times to atmosphere to a minimum.

Shuttle units containing a stack of 4 nylon 6/6 woven meshes of 6 mm diameter in a class 100K cleanroom moulding facility were used. They differ in the following aspects shown in Table 3 below.

TABLE 5

Physical characteristics of the 20 μm and 5 μm meshes

| Mesh Type | Thickness (μm) | Pore size (μm) | Open Area (% area of pores) | Thread diameter (μm) |
|---|---|---|---|---|
| 5 μm | 100 | 5 | 1 | 37 |
| 20 μm | 55 | 20 | 14 | 34 |

Bioreliance Ltd, Stirling, Scotland, U.K., made the 1% polidocanol solution for the study under controlled conditions to the formula in Table 4.

TABLE 6

| | Quantities | |
|---|---|---|
| Material | % w/w | per 1000 g |
| Polidocanol | 1.000 | 10.00 g |
| Ethanol 96% EP | 4.200 | 42.00 g |
| Disodium Hydrogen Phosphate Dihydrate. EP | 0.240 | 2.40 g |
| Potassium Di-hydrogen Phosphate. EP | 0.085 | 0.85 g |
| 0.1 M Sodium Hydroxide Solution [used for adjustment of pH: 7.2-7.5] | q.s. | q.s. |

TABLE 6-continued

| Material | Quantities | |
|---|---|---|
| | % w/w | per 1000 g |
| 0.1 M Hydrochloric Acid | q.s. | q.s. |
| Water for injection. EP [used to adjust to final weight] | approx. 94.475 q.s. to 100.00% | approx. 944.75 g q.s to 1000.00 g |
| TOTAL: | 100.00% | 1000.00 g |

The polidocanol solution was sterile filtered using a 0.2-micron filter before filling into clean glass screw top bottles.

Bi-can assemblies were prepared for testing to the specifications of gas mix and pressure in the polidocanol canister detailed in Table 5.

TABLE 7

Summary of PD canister preparation for each treatment

| Canister Label | Sample Type | Gas Composition | Gas Pressure (bar absolute) | Mesh Pore Size (μm) |
|---|---|---|---|---|
| C | Control 1 | 75% $CO_2$/25% $N_2$ | 0.5 | 20 |
| D | Test 1 | 75% $CO_2$/25% $N_2$ | 0.5 | 5 |
| A | Control 2 | 100% $CO_2$ | 1.2 | 20 |
| B | Test 2 | 100% $CO_2$ | 1.2 | 5 |

The order of testing of the experimental series was important, in that changes in ambient laboratory temperature affect the half separation time results. Experiments progressed cyclically through the sample types rather than test all of one sample type, followed by all of another sample type. This minimised the effect of any drift in laboratory temperature throughout the experiments. The laboratory temperature was maintained as close to 20° C. as possible.

It was also essential that the temperature of the half separation time apparatus be allowed to fully equilibrate to ambient room temperature following cleaning and drying steps between successive experimental measurements.

Summary of Tests:

The tests and specifications performed on the bi-can units in this study are summarised in Table 6.

TABLE 8

Summary of tests and specifications

| | TEST | SPECIFICATION |
|---|---|---|
| 1 | Appearance of Device | No corrosion of canisters or valves. Free from signs of leakage and external damage |
| 2 | Gas Pressure Polidocanol Canister Oxygen Canister | 1.10 to 1.30 bar absolute for Type 2 samples 0.4 to 0.6 bar absolute for Type 1 samples 4.90 to 5.9 bar absolute |
| 3. | Appearance of Foam | Upon actuation, a white foam is produced. After the foam has settled, a clear and colourless liquid is observed. |
| 4. | pH of Solution (collapsed foam) | 6.6 to 7.5 |
| 5 | Foam density | 0.10 to 0.16 g/ml. |
| 6 | Foam Half Separation Time | 150 to 240 seconds |

TABLE 8-continued

Summary of tests and specifications

| | TEST | SPECIFICATION |
|---|---|---|
| 7 | Bubble Size (Diameter Distribution) | |
| | <30 μm | ≤20.0% |
| | 30 μm to 280 μm | ≥75.0% |
| | 281 μm 500 μm | ≤5.0% |
| | >500 μm | None |
| 8 | Particulates (Visible) and Sub-Visible) | Complies with Ph. Eur. |
| 9 | Particulates (Sub-Visible) | The collapsed foam contains not more than 1000 particles per ml ≥10 μm and not more than 100 particles ≥25 μm per ml. |
| 10 | Polidocanol identification by GC method | GC pattern and retention times to be equivalent to reference preparation |
| 11 | Polidocanol Assay | 0.90 to 1.10% w/w |
| 12 | Related Substances | No single identified impurity >0.20% area. No single unidentified impurity >0.10% area. Total impurities ≤4.0% area |

Results:

Results of the tests described in Table 6 on hi-cans prepared as described in Table 5 are summarised in the following paragraphs.

Appear of Device and Foam

In all cases the appearance of the devices conformed to specification in that the device showed no corrosion of canisters or valves and were free from signs of leakage and external damage. Upon actuation of the charged PD canister a white foam was produced. After the foam had settled, a clear and colourless liquid was observed.

Density, Half Separation Time and pH

Foam from all devices conformed to density and half separation time specification. However, one unexpectedly low result was obtained (C1canister 1) but an additional two devices were tested which behaved as expected. In spite of the low result, the average conformed to specification. In general, foam generated via the 5 micron shuttles had longer half separation times. Results are summarised in Table 7.

The average pH of the foam generated conformed to specification. However, foam produced from the 100% CO2 canister were close to the lower limit of detection of the specification and in one instance (C2 canister 4) it was just below specification. Results summarised in Table 7.

The gas pressure in the oxygen cans and the polidocanol cans conformed to specification in all cases. In one instance (C1 canister 6) a slightly lower oxygen canister pressure than expected was recorded. Results are summarised here in Table 7.

TABLE 9

Table summarising the foam density, half separation time, pH and canister gas pressures

| Test Condition Specification | density (g/cm³) 0.10-0.16 | half (sec) 150-240 | life pH 6.6-7.5 | Gas pressure (bars abs) Oxygen 4.9-5.9 | PD 0.4-0.6 |
|---|---|---|---|---|---|
| 100% CO₂, 1.2 Bar, 20 μm mesh | | | | | |
| Canister A1 | 0.12 | 164 | 6.7 | 5.6 | 1.1 |
| Canister A2 | 0.13 | 150 | 6.7 | 5.5 | 1.1 |
| Canister A3 | 0.13 | 153 | 6.6 | 5.8 | 1.1 |
| Canister A4 | 0.15 | 154 | 6.5 | 5.5 | 1.1 |
| Canister A5 | 0.13 | 154 | 6.7 | 5.6 | 1.1 |
| Canister A6 | 0.15 | 154 | 6.5 | 5.6 | 1.1 |
| Average | 0.13 | 155 | 6.6 | 5.6 | 1.1 |
| 100% CO₂, 1.2 Bar, 5 μm mesh | | | | | |
| Canister B1 | 0.12 | 182 | 6.6 | 5.4 | 1.1 |
| Canister B2 | 0.12 | 169 | 6.7 | 5.6 | 1.1 |
| Canister B3 | 0.14 | 162 | 6.6 | 5.4 | 1.1 |
| Canister B4 | 0.1 | 173 | 6.7 | 5.7 | 1.1 |
| Canister B5 | 0.12 | 168 | 6.6 | 5.6 | 1.1 |
| Canister B6 | 0.15 | 161 | 6.5 | 5.4 | 1.1 |
| Average | 0.13 | 169 | 6.6 | 5.5 | 1.1 |
| 75% CO₂/25% N₂, 0.5 Bar, 20 μm mesh | | | | | |
| Canister C1 | 0.14 | 157# | 6.9 | 5.4 | 0.6 |
| Canister C2 | 0.15 | 182 | 6.9 | 5.5 | 0.6 |
| Canister C3 | 0.13 | 193 | 6.9 | 5.4 | 0.6 |
| Canister C4 | 0.15 | 183 | 6.9 | 5.7 | 0.6 |
| Canister C5 | 0.15 | 192 | 6.8 | 5.6 | 0.5 |
| Canister C6 | 0.15 | 191 | 6.9 | 5.0 | 0.6 |
| Canister C11 | 0.14 | 189 | 7.0 | 5.7 | 0.6 |
| Canister C12 | 0.13 | 179 | 7.0 | 5.4 | 0.6 |
| Average | 0.14 | 183 | 6.9 | 5.5 | 0.6 |
| 75% CO₂/25% N₂, 0.5 Bar, 5 μm mesh | | | | | |
| Canister D1 | 0.15 | 203 | 6.9 | 5.4 | 0.6 |
| Canister D2 | 0.12 | 209 | 7.0 | 5.6 | 0.6 |
| Canister D3 | 0.6 | 198 | 6.8 | 5.6 | 0.6 |
| Canister D4 | 0.12 | 205 | 6.9 | 5.7 | 0.6 |
| Canister D5 | 0.12 | 208 | 6.9 | 5.4 | 0.6 |
| Canister D6 | 0.15 | 205 | 6.9 | 5.6 | 0.6 |
| Average | 0.14 | 205 | 6.9 | 5.6 | 0.6 |

Bubble Size Distribution:

The average bubble size for all conditions was within specification with the exception of control 1 (C) where the >500 micron which averaged at one oversized bubble. Results are summarised here in Table 8.

TABLE 10

Table to summarise the bubble size distribution of foam generated

| | Bubble Diameters (μm) | | | |
|---|---|---|---|---|
| Specification | <30 <=20% | 30-280 >=80% | 281-500 <=5% | >500 None |
| 100% CO₂, 1.2 Bar, 20 μm mesh | | | | |
| Canister A1 | 8.2% | 89.5% | 2.3% | 0 |
| Canister A2 | 8.1% | 89.7% | 2.2% | 0 |
| Canister A3 | 7.9% | 85.3% | 6.8% | 0 |
| Canister A4 | 9.0% | 88.3% | 2.6% | 1 |
| Canister A5 | 7.9% | 90.7% | 1.5% | 0 |
| Canister A6 | 11.0% | 88.1% | 0.9% | 0 |
| Average | 8.7% | 88.6% | 2.7% | 0 |
| 100% CO₂, 1.2 Bar, 5 μm mesh | | | | |
| Canister B1 | 7.8% | 91.8% | 0.4% | 0 |
| Canister B2 | 5.5% | 94.2% | 0.3% | 0 |
| Canister B3 | 8.6% | 90.7% | 0.7% | 0 |
| Canister B4 | 8.8% | 91.1% | 0.2% | 0 |
| Canister B5 | 7.7% | 92.2% | 0.0% | 0 |
| Canister B6 | 8.2% | 91.3% | 0.5% | 0 |
| Average | 7.8% | 91.9% | 0.4% | 0 |
| 75% CO₂/25% N₂, 0.5 Bar, 20 μm mesh | | | | |
| Canister C1 | 8.9% | 87.2% | 3.9% | 0 |
| Canister C2 | 10.0% | 89.3% | 0.6% | 0 |
| Canister C3 | 8.9% | 86.5% | 4.5% | 1 |
| Canister C4 | 9.7% | 87.7% | 2.5% | 4 |
| Canister C5 | 10.7% | 87.9% | 1.5% | 0 |
| Canister C6 | 10.1% | 88.0% | 1.9% | 0 |
| Canister C11 | 9.6% | 89.5% | 1.0% | 0 |
| Canister C12 | 11.0% | 87.6% | 1.4% | 0 |
| Average | 9.7% | 88.1% | 2.5% | 1.0 |
| 75% CO₂/25% N₂, 0.5 Bar, 5 μm mesh | | | | |
| Canister D1 | 7.8% | 92.0% | 0.2% | 0 |
| Canister D2 | 8.1% | 91.4% | 0.6% | 0 |
| Canister D3 | 10.9% | 89.0% | 0.1% | 0 |
| Canister D4 | 8.5% | 91.2% | 0.2% | 0 |

TABLE 10-continued

Table to summarise the bubble size distribution of foam generated

| Specification | Bubble Diameters (μm) | | | |
|---|---|---|---|---|
| | <30 <= 20% | 30-280 >= 80% | 281-500 <= 5% | >500 None |
| Canister D5 | 8.8% | 91.1% | 0.1% | 0 |
| Canister D6 | 10.2% | 89.8% | 0.0% | 0 |
| Average | 9.0% | 90.7% | 0.2% | 0 |

Value from Control 1, canister 1 are not included in the average

Particulates (Sub Visible)

The collapsed foam from all canisters complied to specification for particulates, in so far as there were no more than 1,000 particles/ml≥10 μm and no more than 100 particles/ml≥25 μm. Those which had 100% CO2 gas mixture gave the lowest numbers of particles overall. There were no visible particles seen in the collapsed foam. The results are summarised here in Table 7.

The appearance of foam from each device conformed to specification. The appearance of all canisters conformed to specification.

TABLE 11

Sub-visible particulates as per in house method MS14

| Device No | Counts per ml | | | Counts per container (18 ml) | | | Result |
|---|---|---|---|---|---|---|---|
| | ≥10 μm | ≥ 10-25 μm | ≥ 25 μm | ≥10 μm | ≥ 10-25 μm | ≥ 25 μm | |
| Ref A Can 7 | 281.6 | 271.4 | 10.2 | 5,069 | 4,885 | 184 | Complies |
| Ref A Can 8 | 235.3 | 227.9 | 7.4 | 4,235 | 4,102 | 133 | Complies |
| Ref B Can 7 | 112.8 | 109.8 | 3 | 2,030 | 1,976 | 54 | Complies |
| Ref B Can 8 | 123.1 | 116.3 | 6.8 | 2,216 | 2,093 | 122 | Complies |
| Ref C Can 7 | 386.1 | 370.2 | 15.9 | 6,950 | 6,664 | 286 | Complies |
| Ref C Can 8 | 369.5 | 350.6 | 18.9 | 6,651 | 6,311 | 340 | Complies |
| Ref D Can 7 | 130.2 | 123.5 | 6.7 | 2,344 | 2,223 | 121 | Complies |
| Ref D Can 8 | 152.1 | 141.4 | 10.7 | 2,738 | 2,545 | 193 | Complies |

Polidocanol Identification, Assay and Related Substances

No significant differences were observed between the results of the Control and Test preparations. All samples met all specifications for related substances, assay value and identity.

Analysis of the samples using the 25 m column was undertaken, but no significant peaks were observed relating to Nylon 6,6 interactions in these samples.

Example 20

Further Study to Assess the Effect of Physical Properties of Foam from Changes to the Mesh Material in the Mesh Stack The study of Example 9 was repeated using a device in which the shuttle mesh pore size was 20 microns, 11 microns and 5 microns, in combination with changes to the gas pressure and gas composition in the canister. Bi-can assemblies were prepared for testing to the specifications of gas mix and pressure in the polidocanol canister detailed in Table 9.

TABLE 12

Summary of PD canister preparation for each treatment group

| Sample Type | Gas Composition | Gas Pressure (bar absolute) | Mesh Pore Size μm |
|---|---|---|---|
| Control 1 | 75% $CO_2$/25% $N_2$ | 0.5 | 20 |
| Control 2 | 100% $CO_2$ | 1.2 | 20 |
| Test 2 | 100% $CO_2$ | 1.2 | 5 |
| Test 3 | 100% $CO_2$ | 1.2 | 11 |

Various batches of the foam resulting from the test in which the shuttle mesh pore size was 11 microns had the following characteristics:

TABLE 13 a

| Bubble Diameter (micrometers) | | | |
|---|---|---|---|
| <= 30 | > 30 - 280 | > 280 - 500 | > 500 |
| 9.2% | 90.2% | 0.6% | 0.0% |
| 11.8% | 88.2% | 0.0% | 0.0% |
| 10.6% | 89.4% | 0.0% | 0.0% |
| 10.2% | 89.8% | 0.0% | 0.0% |

TABLE 13 a-continued

| Bubble Diameter (micrometers) | | | |
|---|---|---|---|
| <= 30 | > 30 - 280 | > 280 - 500 | > 500 |
| 10.6% | 89.1% | 0.3% | 0.0% |
| 10.5% | 89.4% | 0.1% | 0.0% |

TABLE 13 b

| Bubble Diameter (micrometers) excluding below 30 μm | | | |
|---|---|---|---|
| < 30 - 130 | > 30 - 280 | > 280 - 500 | > 500 |
| 59.1% | 99.4% | 0.6% | 0.0% |
| 71.2% | 100.0% | 0.0% | 0.0% |
| 75.3% | 100.0% | 0.0% | 0.0% |
| 67.3% | 100.0% | 0.0% | 0.0% |
| 66.4% | 99.7% | 0.3% | 0.0% |
| 73.6% | 99.9% | 0.1% | 0.0% |

TABLE 14

Density and Half Life

| Density (g/cm3) | Half Life (Min) |
|---|---|
| 0.12 | 180 sec |
| 0.14 | 171 sec |
| 0.14 | 175 sec |
| 0.12 | 175 sec |
| 0.13 | 177 sec |
| 0.15 | 177 sec |

Example 21

Experiments were conducted to compare the physical properties of sclerosing foam made by the methods of Cabrera, using a range of CO2/O2 gas mixtures as the ambient atmosphere in which a small brush is rotated at high speed to whip polidocanol (PD) solution into a foam, as disclosed in EP 0656203.

All sample preparation was performed under controlled laboratory conditions at temperatures within the range 18-22 degrees C., using polidocanol solution obtained from Kreussler 1% Aethoxysclerol. The container was a 100 ml beaker. The beaker and the 10 ml of solution was placed in a small glass aquarium tank which was modified to allow the internal space to be sealed from atmosphere, then flushed and flooded with the test gas mix.

During the experiments, a small ingress of the test gas mix was present to ensure that atmospheric nitrogen and oxygen cannot enter the glass tank and change the known gas mix. A flexible drive shaft was attached to the micromotor to allow the micromotor to stay outside of the glass tank, whilst driving the brush inside the glass tank at the required speed. Where the flexible drive shaft entered the glass tank, it was sealed to avoid teaks from atmosphere The flushing of the glass tank was performed for 30 seconds with the gas mix supplied at 0.2 bar above atmospheric pressure to the glass tank. After the 30 second flush, the regulator was turned down to allow a trickle of ingressing gas for the rest of the experiment. The speed of rotation and duration of whipping was fixed at 11500 rpm and 90 seconds.

The results in Table 15 show the density and half life of foams made with 100% CO2, 100% O2, 75% CO2/25% O2 and air. For each gas, foams were made with plain polidocanol, polidocanol and 5% glycerol, polidocanol and 25% glycerol and polidocanol and 40% glycerol. Two runs are reported (1 and 2) for each foam. The results show that higher percentages of glycerol enable one to make a CO2 foam with adequate density and half life.

TABLE 15

(a) Air

Density and Half Separation Time

| | Density (g/ml) | Half Life (Sec) |
|---|---|---|
| Plain PD air 1 | 0.16 | 173 |
| Plain PD air 2 | 0.17 | 170 |
| 5% glycerol 1 | 0.20 | 188 |
| 5% glycerol 2 | 0.20 | 195 |
| 25% glycerol 1 | 0.30 | 539 |
| 25% glycerol 2 | 0.27 | 535 |
| 40% glycerol 1 | 0.44 | 459 |
| 40% glycerol 2 | 0.45 | 575 |

(b) 100% O2

Density and Half Separation Time

| | Density (g/ml) | Half Life (Sec) |
|---|---|---|
| Plain PD O2 1 | 0.18 | 122 |
| Plain PD O2 2 | 0.17 | 120 |
| O25GA | 0.18 | 144 |
| O25GB | 0.18 | 140 |
| O225ga | 0.30 | 343 |
| O225gb | 0.34 | 429 |
| O240ga | 0.47 | 432 |
| O240gb | 0.44 | 525 |

(c) 75% CO2/25% O2

Density and Half Separation Time

| | Density (g/ml) | Half Life (Sec) |
|---|---|---|
| 2575 plain PD 1 | 0.20 | 72 |
| 2575 plain PD 2 | 0.18 | 78 |
| 2575 5% G A | 0.16 | 81 |
| 2576 5% G B | 0.19 | 82 |
| 2575 25% G A | 0.33 | 216 |
| 2576 25% G B | 0.29 | 229 |
| 2575 40% G A | 0.46 | 399 |
| 2576 40% G B | 0.47 | 410 |

(d) 100 & CO2

Density and Half Separation Time

| | Density (g/ml) | Half Life (Min) |
|---|---|---|
| Plain PD CO2 1 | 0.19 | 55 |
| Plain PD CO2 2 | 0.19 | 71 |
| CO25GA | 0.24 | 57 |
| CO25GB | 0.20 | 66 |
| CO225ga | 0.29 | 187 |
| CO225gb | 0.33 | 239 |
| co240ga | 0.48 | 227 |
| co240gb | 0.51 | 273 |

Example 22

Polidocanol, Glycerol and CO2 Foams

Foams were made with polidocanol, glycerol and CO2 using various techniques. The technique used to make the foam plays an important role in the half life and density of the resulting foam.

Double Syringe Technique 500 ml of a buffered solution of 1% polidocanol and 30% glycerol was made up using the following procedure.

100% polidocanol (pd)—a waxy solid—was melted by placing in a bath of warm water 100 ml distilled water was weighed out in a 1000 ml beaker 0.425 g potassium dihydrogen phosphate was added as a stabiliser 5 g of the liquefied pd was weighed out 21 g of 96% ethanol was weighed out The ethanol and pd were mixed, then added to distilled water 150 g glycerol was added Water was added to the 425 ml mark pH was adjusted by adding 0.1 M sodium hydroxide to between 7.34 and 7.38 pH.

Distilled water was added to make up to 500 g on scale

The solution was filtered through a 0.25 micron filter.

The same procedure was followed, with an increased amount of glycerol, to make the 40% glycerol solution.

Into a 50 ml glass syringe was drawn 10 ml of the pd/glycerol solution. The nozzle of another 50 ml glass syringe was connected to a line from a cylinder of carbon dioxide (B.O.C. "CP grade" having a purity level of 99.995%). The syringe was filled with carbon dioxide and then removed from the line, the plunger depressed and the syringe then re-filled to the 50 ml graduation on the syringe barrel and then detached from the line. A connector having a female luer at each end and a through bore of diameter approximately 1 mm was then connected to the line and flushed through. The two syringes were then each connected to the connector device.

The carbon dioxide and pd/glycerol solution were then manually pumped back and forth between the two syringes as fast as possible for in excess of 30 cycles. A foam formed in the syringes during this process. After the final cycle, the foam was quickly transferred to half-life and density measuring apparatus and the half life and density of the foam determined.

The procedure was carried out for a buffered solution of 1% polidocanol and 30% glycerol and for a buffered solution of 1% polidocanol and 40% glycerol.

In each case the resulting foam was observed to be somewhat runny, though not like a liquid. It would form very flat, gently rounded "blob" on a surface which decayed and ran away as liquid within five seconds.

Double Syringe and Mesh Technique

The procedure outline above for the double syringe technique was followed, with the following variations.

Instead of using a connector with a 1 mm bore, a so called "mesh stack" device was prepared having a flow path which incorporated a series of four mesh elements. Each mesh element measured about 2-3 mm in diameter and had pores with diameter 5 micron. At each end of the device was a luer connection.

The syringes were again cycled as fast as possible but this was considerably slower than was possible with the simple connector having a 1 mm bore. After 10 cycles the pumping of the syringes was stopped since no further changes in the foam could be observed. Two operators were necessary to perform this cycling, each operator depressing the plunger on a respective syringe.

The procedure was carried out for a buffered solution of 1% polidocanol and 30% glycerol and for a buffered solution of 1% polidocanol and 40% glycerol.

The appearance of the foams made with the double syringe and mesh stack technique was quite similar to those produced with the double syringe style technique: however the "blobs" were less flat and took somewhat longer to decay.

Canister Technique

Pressurised canisters with a capacity of approximately 100 ml were made up with about 20 ml of buffered polidocanol/glycerol solution. The canisters were then pressurised with substantially pure carbon dioxide to a pressure of 3.5 bar absolute.

The canisters are each fitted with a valve, with a dip tube extending from the valve to the base of the canister. On each side of the valve are apertures which draw in gas as liquid passes up the dup tube under pressure. Above the valve, each canister is fitted with a mesh stack unit as described above.

To dispense foam, the canister valve is opened. The first portion of foam is discarded and then foam is dispensed directly into the half life and density measurement apparatus.

The procedure was carried out with canisters containing a buffered solution of 1% polidocanol and 30% glycerol and with canisters t0 containing a buffered solution of 1% polidocanol and 40% glycerol.

The foam produced by the 30% glycerol solution was relatively stiff and formed a compact, rounded blob on a surface. The blob could be seen to start decaying within a few seconds, but remained as a blob rather than a liquid puddle for much longer. Observations were not recorded for the 40% glycerol.

Results
Double Syringe Foam
1) (100% CO2, 1% polidocanol, 30% glycerol)
Density=0.231; Half life=99 secs
2) (100% CO2, 1% polidocanol, 40% glycerol)
Unable to make sufficient amount of foam
Double Syringe and Mesh Technique
1) (100% CO2, 1% polidocanol, 30% glycerol)
Density=0.174; Half life=155 secs
2) (100% CO2, 1% polidocanol 40% glycerol)
Density=0.186; Half life=166 secs
Canister
1) (100% CO2, 1% polidocanol, 30% glycerol)
Density=0.094; Half life=121 secs
2) (100% CO2, 1% polidocanol, 30% glycerol)
Density=0.124; Half life=166 secs
3) (100% CO2, 1% polidocanol, 30% glycerol)
Density=0.124; Half life=108 secs Example 23

Polidocanol, Glycerol and CO2 Foams

The effects of different viscosity enhancing agents (glycerol, PVP and ethanol) on the viscosity of the liquid phase before producing a foam were examined. Viscosity was determined at 23° C. using the Brookfield device described above.

The effects of additional components on the density and half life of CO2 foams made using the methods of Cabrera was also studied. Foams were prepared using the polidocanol (PD) and different percentages of viscosity enhancing agents (wt/wt) and the Cabrera method described above. The halt life and density of the resulting foam was determined as described above. Similar experiments can be used to determine if a particular combination of viscosity enhancing agent, sclerosing agent, and gas provide a foam with a suitable half-life and density. Foams were also produced using a canister as described above and the results are presented in Table 16.

TABLE 16

Canister CO2/glycerol results

| Composition (all compositions are 100% CO2 & 1% polidocanol) | Density (g/ml) | Half life (seconds) | Average Density (g/ml) | Average Half life (seconds) | Viscosity of Liquid Component (cP) |
|---|---|---|---|---|---|
| 5% glycerol | 0.105 | 76 | 0.112 | 63 | 1.5 |
| 5% glycerol | 0.109 | 58 | | | |

TABLE 16-continued

Canister CO2/glycerol results

| Composition (all compositions are 100% CO2 & 1% polidocanol) | Density (g/ml) | Half life (seconds) | Average Density (g/ml) | Average Half life (seconds) | Viscosity of Liquid Component (cP) |
|---|---|---|---|---|---|
| 5% glycerol | 0.111 | 60 | | | |
| 5% glycerol | 0.117 | 59 | | | |
| 5% glycerol | 0.121 | 61 | | | |
| 10% glycerol | 0.112 | 78 | 0.117 | 76 | 1.6 |
| 10% glycerol | 0.115 | 75 | | | |
| 10% glycerol | 0.118 | 78 | | | |
| 10% glycerol | 0.124 | 73 | | | |
| 20% glycerol | 0.113 | 92 | 0.115 | 96 | 2.2 |
| 20% glycerol | 0.113 | 99 | | | |
| 20% glycerol | 0.113 | 104 | | | |
| 20% glycerol | 0.120 | 95 | | | |
| 20% glycerol | 0.114 | 90 | | | |
| 25% glycerol | 0.105 | 111 | 0.109 | 111 | 2.6 |
| 25% glycerol | 0.106 | 109 | | | |
| 25% glycerol | 0.108 | 109 | | | |
| 25% glycerol | 0.109 | 118 | | | |
| 25% glycerol | 0.115 | 106 | | | |
| 30% glycerol | 0.094 | 121 | 0.114 | 132 | — |
| 30% glycerol | 0.124 | 166 | | | |
| 30% glycerol | 0.124 | 108 | | | |
| 40% glycerol | 0.083 | 172 | 0.118 | 173 | — |
| 40% glycerol | 0.133 | 174 | | | |
| 40% glycerol | 0.137 | 174 | | | |
| 1% PVP C30 | 0.091 | 73 | 0.107 | 67 | 1.6 |
| 1% PVP C30 | 0.107 | 62 | | | |
| 1% PVP C30 | 0.111 | 69 | | | |
| 1% PVP C30 | 0.119 | 64 | | | |
| 2% PVP C30 | 0.102 | 70 | 0.107 | 68 | 2.0 |
| 2% PVP C30 | 0.105 | 69 | | | |
| 2% PVP C30 | 0.106 | 69 | | | |
| 2% PVP C30 | 0.114 | 63 | | | |
| 1% PVP K90 | 0.068 | 142 | 0.073 | 135 | 5.0 |
| 1% PVP K90 | 0.071 | 118 | | | |
| 1% PVP K90 | 0.072 | 129 | | | |
| 1% PVP K90 | 0.074 | 159 | | | |
| 1% PVP K90 | 0.078 | 129 | | | |

The invention claimed is:

1. A foam comprising a liquid phase and a gas phase wherein
   the liquid phase comprises at least one sclerosing agent and
   the gas phase consists essentially of 0.01% to 0.8% vol/vol nitrogen, 10% to 99.99% vol/vol carbon dioxide, and the remaining gas, if any, consisting essentially of oxygen.

2. The foam of claim 1, wherein the nitrogen is present in an amount ranging from 0.01% to 0.7%.

3. The foam of claim 1, wherein the nitrogen is present in an amount ranging from 0.01% to 0.6%.

4. The foam of claim 1, wherein the foam has a density of less than 0.25 g/ml and a half life of greater than 100 secs.

5. The foam of claim 1, wherein the foam has a half of at least 120 seconds.

6. The foam of claim 1, wherein the foam has a half life of at least 150 seconds.

7. The foam of claim 1, wherein the foam has a half life of at least 180 seconds.

8. The foam of claim 1, wherein the foam has a density ranging from 0.07 to 0.22 g/ml.

9. The foam of claim 1, wherein the foam has a density ranging from 0.07 to 0.19 g/ml.

10. The foam of claim 1, wherein the foam has a density ranging from 0.07 to 0.16 g/ml.

11. The foam of claim 1, wherein the foam has a density ranging from 0.08 to 0.14 g/ml.

12. The foam of claim 1, wherein the at least one sclerosing agent is chosen from polidocanol, glycerol and sodium tetradecyl sulphate.

13. The foam of claim 1, wherein the at least one sclerosing agent is polidocanol.

14. The foam of claim 13, wherein the polidocanol is present in a concentration ranging from 0.5% to 4% vol/vol in the liquid phase.

15. A foam comprising:
   a liquid phase and a gas phase, wherein
   the liquid phase comprises at least one sclerosing agent; and
   the gas phase consists essentially of 0.01% to 0.8% vol/vol nitrogen, about 10% to about 99.99% vol/vol carbon dioxide, and the remaining gas, if any, consisting essentially of oxygen.

16. The foam of claim 15, wherein the nitrogen is present in an amount ranging from 0.01% to 0.7%.

17. The foam of claim 15, wherein the nitrogen is present in an amount ranging from 0.01% to 0.6%.

18. The foam of claim 15, wherein the foam has a density of less than 0.25 g/ml and a half life of greater than 100 secs.

19. The foam of claim 15, wherein the foam has a half life of at least 120 seconds.

20. The foam of claim 15, wherein the foam has a half life of at least 150 seconds.

21. The foam of claim 15, wherein the foam has a half life of at least 180 seconds.

22. The foam of claim 15, wherein the foam has a density ranging from 0.07 to 0.22 g/ml.

23. The foam of claim 15, wherein the foam has a density ranging from 0.07 to 0.19 g/ml.

24. The foam of claim 15, wherein the foam has a density ranging from 0.07 to 0.16 g/ml.

25. The foam of claim 15, wherein the foam has a density ranging from 0.08 to 0.14 g/ml.

26. The foam of claim 15, wherein the at least one sclerosing agent is chosen from polidocanol, glycerol and sodium tetradecyl sulphate.

27. The foam of claim 15, wherein the at least one sclerosing agent is polidocanol.

28. The foam of claim 27, wherein the polidocanol is present in a concentration ranging from 0.5% to 4% vol/vol in the liquid phase.

29. A foam comprising:
a liquid phase and a gas phase, wherein
the liquid phase comprises at least one sclerosing agent; and
the gas phase consists essentially of 0.01% to 0.8% vol/vol nitrogen, at least 50% vol/vol carbon dioxide, and the remaining gas, if any, consisting essentially of oxygen.

30. The foam of claim 29, wherein the nitrogen is present in an amount ranging from 0.01% to 0.7%.

31. The foam of claim 29, wherein the nitrogen is present in an amount ranging from 0.01% to 0.6%.

32. The foam of claim 29, wherein the foam has a density of less than 0.25 g/ml and a half life of greater than 100 secs.

33. The foam of claim 29, wherein the foam has a half life of at least 120 seconds.

34. The foam of claim 29, wherein the foam has a half life of at east 150 seconds.

35. The foam of claim 29, wherein the foam has a half life of at least 180 seconds.

36. The foam of claim 29, wherein the foam has a density ranging from 0.07 to 0.22 g/ml.

37. The foam of claim 29, wherein the foam has a density ranging from 0.07 to 0.19 g/ml.

38. The foam of claim 29, wherein the foam has a density ranging from 0.07 to 0.16 g/ml.

39. The foam of claim 29, wherein the foam has a density ranging from 0.08 to 0.14 g/ml.

40. The foam of claim 29, wherein the at least one sclerosing agent is chosen from polidocanol, glycerol and sodium tetradecyl sulphate.

41. The foam of claim 29, wherein the at least one sclerosing agent is polidocanol.

42. The foam of claim 41, wherein the polidocanol is present in a concentration ranging from 0.5% to 4% vol/vol in the liquid phase.

* * * * *